United States Patent
Masui et al.

(10) Patent No.: US 9,018,219 B2
(45) Date of Patent: Apr. 28, 2015

(54) FUSED AMINODIHYDROPYRIMIDINE DERIVATIVE

(75) Inventors: Moriyasu Masui, Toyonaka (JP); Genta Tadano, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/881,112

(22) PCT Filed: Oct. 27, 2011

(86) PCT No.: PCT/JP2011/074762
§ 371 (c)(1),
(2), (4) Date: Apr. 23, 2013

(87) PCT Pub. No.: WO2012/057247
PCT Pub. Date: May 3, 2012

(65) Prior Publication Data
US 2013/0210839 A1    Aug. 15, 2013

(30) Foreign Application Priority Data

Oct. 29, 2010  (JP) .................... 2010-244115

(51) Int. Cl.
| | | |
|---|---|---|
| A01N 43/90 | (2006.01) | |
| A61K 31/519 | (2006.01) | |
| C07D 239/70 | (2006.01) | |
| C07D 487/04 | (2006.01) | |

(52) U.S. Cl.
CPC .............. C07D 487/04 (2013.01); A61K 31/519 (2013.01)

(58) Field of Classification Search
None
See application file for complete search history.

(56) References Cited

U.S. PATENT DOCUMENTS

| | | |
|---|---|---|
| 2,899,426 A | 8/1959 | Bloom |
| 3,115,494 A | 12/1963 | Joseph et al. |
| 3,227,713 A | 1/1966 | Behner |
| 3,235,551 A | 2/1966 | Werner |
| 3,577,428 A | 5/1971 | Suh et al. |
| 3,636,116 A | 1/1972 | Trepanier |
| 3,719,674 A | 3/1973 | Trepanier |
| 3,775,409 A | 11/1973 | Harsanyi et al. |
| 4,049,807 A | 9/1977 | Paulus et al. |
| 4,311,840 A | 1/1982 | Condon |
| 4,895,841 A | 1/1990 | Sugimoto et al. |
| 4,906,626 A | 3/1990 | Amrein et al. |
| 5,100,901 A | 3/1992 | Sugimoto et al. |
| 5,236,942 A | 8/1993 | Miller |
| 5,328,915 A | 7/1994 | Long et al. |
| 5,880,147 A | 3/1999 | Yoshida et al. |
| 5,952,374 A | 9/1999 | Clarkson, Jr. et al. |
| 6,096,753 A | 8/2000 | Spohr et al. |
| 6,590,123 B2 | 7/2003 | Bekesi et al. |
| 6,713,276 B2 | 3/2004 | Cordell et al. |
| 7,183,070 B2 | 2/2007 | Cordell et al. |

(Continued)

FOREIGN PATENT DOCUMENTS

| | | |
|---|---|---|
| CA | 2163724 | 5/1996 |
| CA | 2165386 | 6/1996 |

(Continued)

OTHER PUBLICATIONS

Emilio Testa et al.: "Auf das Zentralnervensystem wirkende Substanzen, XXXVI. Weitere Untersuchungen über die 2-substituierten Azetidine; Justus Liebigs Annalen Der Chemie", vol. 673, No. 1., May 4, 1964, pp. 60-70 XP055091964.

Portnyagin et al.: Russian Journal of Organic Chemistry, Consultants Bureau, US, vol. 10, Jan. 1, 1974, pp. 95-98, XP009174887.

Database CAPLUS [Online]; Chemical Abstracts Service, Columbus, OH, US; 2006, Bathich, Yaser: "Synthesis of Branched Amino Polyoly and Aminohydroxy Acids: Stereoselective Additiom of C-Nucleophiles ti Isoxazolines and Isoxazolinium Salts and Assignment of Configurations", XP002717806.

(Continued)

*Primary Examiner* — Jeffrey H Murray
(74) *Attorney, Agent, or Firm* — Hamre, Schumann, Mueller & Larson, P.C.

(57) ABSTRACT

The present invention provides, for example, the following compound:

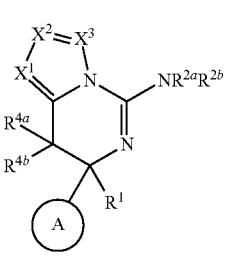

(I)

wherein ring A is a substituted or unsubstituted carbocycle or a substituted or unsubstituted heterocycle, $X^1$—$X^2$=$X^3$ is $CR^5$—$CR^6$=$CR^7$, N—$CR^6$=$CR^7$, $CR^5$—N=$CR^7$ or $CR^5$—$CR^6$=N, $R^1$ is substituted or unsubstituted alkyl, substituted or unsubstituted alkenyl or the like, $R^{2a}$ and $R^{2b}$ are each independently hydrogen, substituted or unsubstituted alkyl or the like, $R^{4a}$, $R^{4b}$, $R^5$, $R^6$ and $R^7$ are each independently hydrogen, halogen, hydroxy, substituted or unsubstituted alkyl or the like, its pharmaceutically acceptable salt or a solvate thereof having an effect of inhibiting amyloid β production, especially a BACE1 inhibitory activity, and useful as a medicament for treating diseases induced by production, secretion or deposition of amyloid β proteins.

16 Claims, No Drawings

(56) References Cited

U.S. PATENT DOCUMENTS

| | | |
|---|---|---|
| 7,309,706 B2 | 12/2007 | Rupp et al. |
| 7,326,792 B2 | 2/2008 | Shum et al. |
| 7,414,050 B2 | 8/2008 | Illig et al. |
| 7,763,609 B2 | 7/2010 | Zhu et al. |
| 7,902,238 B2 | 3/2011 | Galley et al. |
| 8,173,642 B2 | 5/2012 | Kobayashi et al. |
| 2002/0019427 A1 | 2/2002 | Carry et al. |
| 2005/0165080 A1 | 7/2005 | Rupp et al. |
| 2006/0173006 A1 | 8/2006 | Sun et al. |
| 2006/0183790 A1 | 8/2006 | Cole et al. |
| 2006/0183792 A1 | 8/2006 | Fobare et al. |
| 2006/0183943 A1 | 8/2006 | Hu et al. |
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0224656 A1 | 9/2007 | Cordell et al. |
| 2008/0200445 A1 | 8/2008 | Zhu et al. |
| 2009/0023729 A1 | 1/2009 | Nakamuta et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0125087 A1 | 5/2010 | Holenz et al. |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2012/0202828 A1 | 8/2012 | Castro Pineiro et al. |
| 2012/0238548 A1 | 9/2012 | Gabellieri et al. |
| 2012/0238557 A1 | 9/2012 | Masui et al. |
| 2012/0245154 A1 | 9/2012 | Anan et al. |
| 2012/0245155 A1 | 9/2012 | Yoshida et al. |
| 2012/0245157 A1 | 9/2012 | Masui et al. |
| 2012/0253035 A1 | 10/2012 | Narquizian et al. |
| 2012/0258961 A1 | 10/2012 | Suzuki et al. |
| 2012/0258962 A1 | 10/2012 | Hilpert et al. |
| 2012/0295900 A1 | 11/2012 | Hilpert et al. |
| 2013/0158260 A1 | 6/2013 | Kobayashi et al. |
| 2013/0217705 A1 | 8/2013 | Mitsuoka et al. |
| 2013/0303755 A1 | 11/2013 | Kobayashi et al. |

FOREIGN PATENT DOCUMENTS

| | | |
|---|---|---|
| DE | 140144 | 2/1980 |
| EP | 0 798 292 | 10/1995 |
| EP | 0 713 704 | 5/1996 |
| EP | 0 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1942105 | 7/2008 |
| EP | 2147914 | 1/2010 |
| EP | 2151435 | 2/2010 |
| EP | 2233474 | 9/2010 |
| EP | 2305672 | 4/2011 |
| EP | 2332943 | 6/2011 |
| EP | 2 360 155 | 8/2011 |
| EP | 2415756 | 2/2012 |
| GB | 1001093 | 8/1965 |
| JP | 62-120374 | 6/1987 |
| JP | 8-231521 | 9/1996 |
| JP | 9-067355 | 3/1997 |
| JP | 10-505862 | 6/1998 |
| JP | 11-349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| WO | WO 94/12165 | 6/1994 |
| WO | WO 95/09619 | 4/1995 |
| WO | WO 96/09286 | 3/1996 |
| WO | WO 96/14842 | 5/1996 |
| WO | WO 96/18608 | 6/1996 |
| WO | WO 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | WO 01/19788 | 3/2001 |
| WO | WO 01/78709 | 10/2001 |
| WO | WO 01/87293 | 11/2001 |
| WO | 2002/062766 | 8/2002 |
| WO | 02/088101 | 11/2002 |
| WO | WO 02/096897 | 12/2002 |
| WO | 03/040096 | 5/2003 |
| WO | WO 03/039446 | 5/2003 |
| WO | WO 03/040115 | 5/2003 |
| WO | WO 03/040142 | 5/2003 |
| WO | WO 03/082191 | 10/2003 |
| WO | 2004/009549 | 1/2004 |
| WO | WO 2004/014843 | 2/2004 |
| WO | 2004/031154 | 4/2004 |
| WO | 2004/039404 | 5/2004 |
| WO | WO 2004/043916 | 5/2004 |
| WO | WO 2004/096795 | 11/2004 |
| WO | WO 2005/014555 | 2/2005 |
| WO | WO 2005/032493 | 4/2005 |
| WO | 2005/058311 | 6/2005 |
| WO | 2005/065277 | 7/2005 |
| WO | WO 2005/097767 | 10/2005 |
| WO | WO 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | WO 2006/041404 | 4/2006 |
| WO | WO 2006/041405 | 4/2006 |
| WO | WO 2006/065204 | 6/2006 |
| WO | 2006/076284 | 7/2006 |
| WO | 2006/099379 | 9/2006 |
| WO | 2006/138192 | 12/2006 |
| WO | 2006/138265 | 12/2006 |
| WO | WO 2006/138217 | 12/2006 |
| WO | WO 2006/138304 | 12/2006 |
| WO | 2007/002220 | 1/2007 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | 2007/049532 | 5/2007 |
| WO | 2007/058583 | 5/2007 |
| WO | WO 2007/058580 | 5/2007 |
| WO | WO 2007/058582 | 5/2007 |
| WO | WO 2007/058601 | 5/2007 |
| WO | WO 2007/058602 | 5/2007 |
| WO | WO 2007/073284 | 6/2007 |
| WO | WO 2007/078813 | 7/2007 |
| WO | 2007/092846 | 8/2007 |
| WO | 2007/092854 | 8/2007 |
| WO | WO 2007/114771 | 10/2007 |
| WO | WO 2007/120096 | 10/2007 |
| WO | WO 2007/146225 | 12/2007 |
| WO | WO 2008/011560 | 1/2008 |
| WO | 2008/022024 | 2/2008 |
| WO | 2008/073365 | 6/2008 |
| WO | WO 2008/073370 | 6/2008 |
| WO | 2008/103351 | 8/2008 |
| WO | 2008/133273 | 11/2008 |
| WO | 2008/133274 | 11/2008 |
| WO | WO 2009/010454 | 1/2009 |
| WO | 2009/064418 | 5/2009 |

(56) References Cited

FOREIGN PATENT DOCUMENTS

| | | |
|---|---|---|
| WO | 2009/091016 | 7/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | 2009/134617 | 11/2009 |
| WO | 2009/151098 | 12/2009 |
| WO | 2010/019392 | 2/2010 |
| WO | 2010/019393 | 2/2010 |
| WO | WO 2010/013302 | 2/2010 |
| WO | WO 2010/013794 | 2/2010 |
| WO | 2010/038686 | 4/2010 |
| WO | 2010/047372 | 4/2010 |
| WO | 2010/056194 | 5/2010 |
| WO | 2010/056195 | 5/2010 |
| WO | 2010/056196 | 5/2010 |
| WO | 2010/113848 | 10/2010 |
| WO | 2010/129864 | 11/2010 |
| WO | WO 2010/128058 | 11/2010 |
| WO | 2011/009897 | 1/2011 |
| WO | 2011/009898 | 1/2011 |
| WO | 2011/009943 | 1/2011 |
| WO | WO 2011/005738 | 1/2011 |
| WO | WO 2011/009943 | 1/2011 |
| WO | WO 2011/020806 | 2/2011 |
| WO | 2011/029803 | 3/2011 |
| WO | WO 2011/044181 | 4/2011 |
| WO | WO 2011/044184 | 4/2011 |
| WO | WO 2011/044185 | 4/2011 |
| WO | WO 2011/044187 | 4/2011 |
| WO | 2011/058763 | 5/2011 |
| WO | 2011/060207 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | WO 2011/080176 | 7/2011 |
| WO | 2011/138293 | 11/2011 |
| WO | 2011/154431 | 12/2011 |
| WO | WO 2011/154374 | 12/2011 |
| WO | 2012/006953 | 1/2012 |
| WO | WO 2012/000933 | 1/2012 |
| WO | 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/095469 | 7/2012 |
| WO | 2012/095521 | 7/2012 |
| WO | 2012/098064 | 7/2012 |
| WO | 2012/098213 | 7/2012 |
| WO | 2012/098461 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |

OTHER PUBLICATIONS

Database Registry [Online]; Chemical Abstracts Service, Columbus, OH, US; 3-Pyridinepropanol, .beta., .gamma.-diamino-6-fluoro-.gamma.-(4-fluorophenyl)-, (.beta.-R,.gamma.S)-, Apr. 29, 2004, XP002717807.

Church J et al.: "Anticonvulsant actions of phencyclidine receptor ligands: Correlation with N-Methylaspartate Antagonism in vivo"; General Phamacology, Pergamon Press, Oxford, GB, vol. 21, No. 2, Jan. 1, 1990, pp. 165-170, XP023834032.

Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.

Mulcahy et al., "A stereoselective synthesis of (+)-Gonyautoxin 3," Journal of the American Chemical Society, 2008, vol. 130, pp. 12630-12631.

"Diphenyl Cyanocarbonimidate," e-EROS Encyclopedia of Reagents for Organic Synthesis, 2001, 2 pages total.

Shafik et al., "Synthesis of novel 2-[2-(substituted amino)phenethyl]-1H-benzimidazoles; 3,4-dihydro and 1,2,3,4-tetrahydropyrimido[1,6-α]-benzimidazoles as potential antiulcer agents," 2004, Pharmazie, vol. 59, No. 12, pp. 899-905.

Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.

Buschauer et al., "Isohistamine und Homologe als Bausteine von $H_2$-Antagonisten,"Arzneimittel-Forschung, 1985, vol. 35, pp. 1025-1029 (English language abstract provided).

Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.

Borchers et al., "$H_2$-Antihystaminika, 19. Mitt.[1)] Syntheses und $H_2$-antihistaminische Wirkung $W_α$-substituierter Histamine," Archiv der Pharmazie (Weinheim, Germany), 1984, vol. 317, pp. 455-459.

Cheong et al., "Pharmacophore elucidation for a new series of 2-aryl-pyrazolo-triazolo-pyrimidines as potent human $A_3$ adenosine receptor antagonists," Bioorganic & Medicinal Chemistry Letters, 2011, vol. 21, pp. 2898-2905.

Xu et al., "Copper-catalyzed cascade synthesis of benzimidazoquinazoline derivatives under mild condition," Chemical Communications, 2011, vol. 47, pp. 5596-5598.

Kishore et al., "QSAR of adenosine receptor antagonists: exploring physicochemical requirements for binding of pyrazolo[4,3-e]-1,2,4-triazolo[1,5-c]pyrimidine derivatives with human adenosine $A_3$ receptor subtype," Bioorganic & Medicinal Chemistry Letters, 2011, vol. 21, No. 2, pp. 818-823.

Edwards, et al., "Application of Fragment-Based Lead Generation to the Discovery of Novel, Cyclic Amidine β-Secretase Inhibitors with Nanomolar Potency, Cellular Activity, and High Ligand Efficiency", Journal of Medicinal Chemistry, vol. 50, No. 24, 2007, pp. 5912-5925.

Kuo, et al., "A Synthesis of Estrone via Novel Intermediates. Mechanism of the Coupling Reaction of a Vinyl Carbinol with a β Diketone", The Journal of Organic Chemistry, vol. 33, No. 8, Aug. 1968, pp. 3126-3132.

Cohen, et al., "Synthesis of 2-Amino-5,6-dihydro-4,H-1,3-thiazines and Related Compounds by Acid Catalyzed Cyclizationof Allylic Isothiuronium Salts", Journal of Heterocyclic Chemistry, vol. 14, 1977, pp. 717-723.

Hünig, et al., "Azofarbstoffe Durch Oxydative Kupplung, XVIII. Synthese von-3-substituierten Thiazolon-(2)-hydrazonen und Thiazolon-(2)-benzolsulfonylhydrazonen", European Journal of Organic Chemistry, vol. 647, No. 1, May 1961, pp. 66-76.

Schaumann, et al., "Cycloadditionsreaktionen von Heterokumulenen, XXIII. Stickstoffhaltige Fünfring-Heterocyclen aus Carbodiimiden oder Keteniminen mit 3-Dimethylamino-2H-azirinen", Liebigs Ann. Chem., 1981, pp. 290-305.

(56) References Cited

OTHER PUBLICATIONS

Cambie, et al., "*vic*-Iodothiocyanates and Iodoisothiocyanates. Part 2. New Syntheses of Thiazolidin-2-ones and 2-Amino-2-thiazolines", Journal of the Chemical Society, Perkin Transactions I, No. 3, 1979, pp. 765-770.

Fernández, et al., "Syntheses of β-iodourea derivatives of carbohydrates and glycosylamino-oxazolines", Carbohydrate Research, vol. 216, 1991, pp. 21-32.

Fernández, et al., "Syntheses and Spectral Properties of β-Iodoureas and 2-Amino-4,4-diphenyl-2-oxazolines", Journal of Heterocyclic Chemistry, vol. 28, 1991, pp. 777-780.

Liebscher, et al., "2-Arylimino-3-Thiazolines—Formation of Unusual Tautomers of 2-Arylamino-Thiazolines—a Revision", Tetrahedron Letters, vol. 26, No. 35, 1985, pp. 4179-4180.

Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.

Fujisawa et al., "Switchover of diastereofacial selectivity in the condensation reaction of optically active N-sulfinimine with ester enolate," Tetrahedron Letters, vol. 37, No. 22, 1996, pp. 3881-3884.

Vilaivan et al., "Recent Advances in Catalytic Asymmetric Addition to Imines and Related C=N Systems," Current Organic Chemistry, vol. 9, 2005, pp. 1315-1392.

Hua et al., "N-Alkylidenesulfinamides," Sulfur Reports, vol. 21, 1999, pp. 211-239.

Savoca et al., "1,5-Diazabicyclo[4.3.0]non-5-ene[1]," Encyclopedia of Reagents for Organic Synthesis, 2006, 10 pages total.

Creeke et al., "Synthesis and elaboration of heterocycles via iodocyclisation of unsaturated thioureas," Tetrahedron Letters, 1989, vol. 30, No. 33, pp. 4435-4438.

Mellor et al.,"A general route to spirocycles by radical additions to exocyclic unsaturated sulphides and related compounds," Tetrahedron Letters, 1991, vol. 32, No. 48, pp. 7111-7114.

Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.

Singh et al., "Synthesis of heterocyclic compounds via enamines. Part 8.[†] Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.

Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).

Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 935998-84-8.

Schubert et al., "Neue synthesen von 2-Amino-5,6-dihydro-4H-1,3-thiazinen," Archiv der Pharmazie, 1968, vol. 301, No. 10, pp. 750-762.

Huang et al., "Pharmacophore model construction of β-secretase inhibitors," 2008, Acta Chimica Sinica, vol. 66, No. 16, pp. 1889-1897 (English language abstract provided).

Clark, et al., "Antitumor Imidazotetrazines, 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.

Congreve, et al., "Application of Fragment Screening by X-ray Crystallography to the Discovery of Aminopyridines as Inhibitors of β-Secretase", J. Med. Chem., vol. 50, 2007, pp. 1124-1132.

Huang, et al., "Progress in the Development of Nonpeptidomimetic BACE 1 Inhibitors for Alzheimer's Disease", Current Medicinal Chemistry, vol. 16, 2009, pp. 1806-1820.

Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.

Siddiqui et al., "Some extensions of Von Bruan (BrCN) reaction on organic bases," Proc. Pakistan Acad. Sci., 1988, vol. 25, No. 3, pp. 231-240.

Ozawa et al., Pharmacological actions of 2-Aminoethylisothiuronium (AET) derivatives. I[1), Yakugaku Zasshi, 1968, vol. 88, No. 2, pp. 156-162 (English language abstract provided).

Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.

Burton et al., "Addition reactions of quinones. Part I. The reaction of cysteine and thiourea and its derivatives with some quinones," Journal of the Chemical Society, 1952, pp. 2193-2196.

Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103).

Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.

Cole et al., "Acylguanidines as small-molecule beta-secretase inhibitors," J. Med. Chem., 2006, pp. 6158-6161.

Bol'but et al., Heterocyclizations of Functionalized Heterocumulenes with C,N- and C,O-Dinucleophiles: III.* Cyclization of N-(1-Aryl-1-chloro-2,2,2-trifluoroethyl)-N'-arylcarbodiimides with 3-Substituted 1-Phenylpyrazol-5-ones, Russian Journal of Organic Chemistry, 2003, vol. 29, No. 2, pp. 1789-1791.

Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.

Sayed et al., "α-Enones in heterocyclic synthesis of indazole, thiazine, chromene and quinolone derivatives with their antimicrobial activities," Journal of Chemical Research, 2009, vol. 12, pp. 726-728.

Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.

Bol'but et al., "Synthesis of 4-imino-2-trifluoromethyl-3,4-dihydro-2h-Benzo-[1,3]Thiazines" Chemistry of Heterocyclic Compounds, 2001, vol. 37, No. 4, pp. 522-523.

Vovk et al., "Intramolecular thermal cyclization of N-(1-Aryl-1-aryloxy-2,2,2-trifluoroethyl)-N'-arylcarbodiimides" Russian Journal of Organic Chemistry, 2000, vol. 36, No. 12, pp. 1739-1742.

Vovk et al., "Regioselective cyclization of 1-chloroalkylcarbodiimides with 1,1- and 1,2-bifunctional nucleophilic reagents" Russian Journal of Organic Chemistry, 1997, vol. 33, No. 1, pp. 96-102.

Potts et al., "N-Acyl-β-enamino Ketones: Versatile Heterocyclic Synthons" J. Org. Chem., 1983, 48, pp. 623-625.

Rivkin et al., "Piperazinyl pyrimidine derivatives as potent γ-secretase modulators" Bioorganic & Medicinal Chemistry Letters, 2010, 20, pp. 1269-1271.

Rivkin et al., "Purine derivatives as potent γ-secretase modulators" Bioorganic & Medicinal Chemistry Letters, 2010, 20, pp. 2279-2282.

Vippagunta et al. "Crystalline Solids". Advanced Drug Delivery Reviews, vol. 48, 2001, pp. 3-26.

Gavezzotti. "Are Crystal Structures Predictable". Accounts of Chemical Research, vol. 27, 1994, pp. 309-314.

STN a the Web, RN 79005-45-1, 1964.

Zhu et al., Two novel Diastereoselective Three-Component Reactions of Alkenes or 3,4-Dihydro-(2H)-pyran with Urea/Thiourea-Aldehyde Mixtures: [4+] Cycloaddition vs Biginelli-Type Reaction, Organic Letters, 2006, vol. 8, No. 12, pp. 2599-2602.

(56) References Cited

OTHER PUBLICATIONS

Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).
Kavya et al. "Nitric oxide synthase regulation and diversity: Implications in Parkinson's Disease". Nitric Oxide: Biology and Chemistry, vol. 15, No. 4, pp. 280-294 (2006).
Chiou et al. "Review: Effects of Nitric Oxide on Eye Diseases and Their Treatment". Journal of Ocular Pharmacology and Therapeutics, vol. 17, No. 2, pp. 189-198 (2001).
Ishii et al. "Subacute NO generation induced by Alzheimer's β-amyloid in the living brain: reversal by inhibition of the inducible NO synthase". The Federation of American Societies for Experimental Biology Journal, vol. 14, pp. 1485-1489 (2000).
Pak et al. "Morphine via nitric oxide modulates β-amyloid metabolism: a novel protective mechanism for Alzheimer's disease". Medical Science Monitor, vol. 11, No. 10, pp. BR357-BR366 (2005).
Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.
Beaton et al., "The synthesis of 1-aminodihydroisoquinolines by an imine addition cyclisation reaction," 1998, Tetrahedron Letters, vol. 39, pp. 1227-1230.
Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. 1, pp. 49-53.
Weinhardt et al. "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.
Meschino et al., "2-Amino-5,6-dihydro-1,3-oxazines. The reduction of carboxylic esters with sodium borohydride," J. Org. Chem., vol. 28, 1963, pp. 3129-3134.
Poos et al., "2-amino-5-aryl-2-oxazolines. Potent new anorectic agent," J. Med. Chem., vol. 6, 1963, pp. 266-272.
Sandin et al., "A fast and parallel route to cyclic isothioureas and guanidines with use of microwave-assisted chemistry," J. Org. Chem., vol. 69, 2004, pp. 1571-1580.
Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.
Woodgate et al., "A new synthesis of 2-amino-2-thiazolines," Heterocycles, vol. 7, No. 1, 1977, pp. 109-112.
Co-pending U.S. Appl. No. 13/941,082, entitled Aminodihydrothiazine Derivatives, filed Jul. 12, 2013.
Co-pending U.S. Appl. No. 13/887,745, entitled Aminodihydrothiazine Derivatives Substituted With a Cyclic Group, filed May 6, 2013.
Co-pending U.S. Appl. No. 13/952,073, entitled Sulfur-Containing Heterocyclic Derivative Having Beta Secretase Inhibitory Activity, filed Jul. 26, 2013.
Dörwald, "Side reactions in organic synthesis: a guide to successful synthesis design" 2005 Wiley-VCH Verlag GmbH & Co., KGaA, Wienheim, chapter I, 32 pages total.
Wermuth; Practice of Medicinal Chemistry, Third Ed., 2008, Elsevier, chapter 15.
Co-pending U.S. Appl. No. 14/112,400, entitled Pyridine Derivatives and a Pharmaceutical Composition for inhibitiing BACE1 Containing them, filed Oct. 17, 2013.
Co-pending U.S. Appl. No. 14/113,327, entitled Oxazine Derivatives and a Pharmaceautical Composition for Inhibiting BACE1 Containing them, filed Oct. 22, 2013.
Co-pending U.S. Appl. No. 14/070,202, entitled A Pharmaceutical Composition for Treating Alzheimer's disease, filed Nov. 1, 2013.
Bathich, "Synthesis of branched amino polyols and amino hydroxy acids: stereoselective addition of C-Nucleophiles to isoxazoline and isoxazolinium salts and assignment of configurations," 2006, pp. 148.
Dolzhenko et al., "-8-methyl-2[4-(trifluoromethyl)phenyl]-8H-pyrazolo[4,3-e][1,2,4]triazolo[1,5-c]-pyrimidin-5-amine methanol clisolyate," Acta Crystallographica, 2010, Section E: Structure Reports Online, E66(7), 12 pages total.

FUSED AMINODIHYDROPYRIMIDINE DERIVATIVE

TECHNICAL FIELD

The present invention relates to a compound having an effect of inhibiting amyloid β production and is useful as a medicament for treating diseases induced by production, secretion and/or deposition of amyloid β proteins.

BACKGROUND ART

In the brains of patients with Alzheimer's disease, peptides each consisting of approximately 40 amino acids, called amyloid β proteins, which widely accumulate outside neurons to form insoluble plaques (senile plaques) are observed. These senile plaques are considered to kill neurons and cause the onset of Alzheimer's disease, and therefore, agents promoting degradation of amyloid β proteins and amyloid β vaccines have been studied as therapeutic agents for Alzheimer's disease.

Secretases are enzymes which cleave a protein called amyloid precursor protein (APP) within a cell and generate an amyloid β protein. An enzyme which produces N-terminals of amyloid β proteins is called as BACE1 (beta-site APP-cleaving enzyme 1, BACE1). It is considered that production of amyloid β proteins may be suppressed by inhibiting this enzyme, and thus a substance with such an effect can serve as a therapeutic agent for Alzheimer's disease.

Patent Documents 1 to 7 disclose BACE 1 inhibitors but each of them has a structure different from those of the compounds of the present invention.

Patent Documents 21 to 23 and Non-Patent Documents 1 to 12 disclose compounds having a structure similar to those of the compounds of the present invention, but none of these document discloses each of these compound has BACE1 inhibitory activity nor is useful as a therapeutic agent for Alzheimer's disease.

PRIOR ART

Patent Document

[Patent Document 1] WO2006/138265
[Patent Document 2] WO2006/009655
[Patent Document 3] WO2006/076284
[Patent Document 4] WO2008/022024
[Patent Document 5] WO2010/056194
[Patent Document 6] WO2010/056195
[Patent Document 7] WO2010/056196
[Patent Document 8] WO2007/058583
[Patent Document 9] WO2007/049532
[Patent Document 10] WO2008/133274
[Patent Document 11] WO2008/133273
[Patent Document 12] WO2009/151098
[Patent Document 13] WO2010/047372
[Patent Document 14] WO2010/113848
[Patent Document 15] WO2011/071057
[Patent Document 16] WO2011/058763
[Patent Document 17] WO2011/070781
[Patent Document 18] WO2011/077726
[Patent Document 19] WO2011/071135
[Patent Document 20] WO2011/071109
[Patent Document 21] WO2006/023750
[Patent Document 22] WO2011/060207
[Patent Document 23] WO2010/129864

Non-Patent Document

[Non-patent Document 1] Tetrahedron Letters, vol. 50, No. 27, p. 3809-3812 (2009)
[Non-patent Document 2] Journal of the American Chemical Society, vol. 130, No. 38, p. 12630-12631 (2008),
[Non-patent Document 3] e-EROS Encyclopedia of Reagents for Organic Synthesis, (2001), "Diphenyl Cyanocarbonimidate"
[Non-patent Document 4] Pharmazie, vol. 59, No. 12, p. 899-905 (2004)
[Non-patent Document 5] Journal fuer Praktische Chemie/Chemiker-Zeitung, vol. 334, No. 7, p. 630-636 (1992)
[Non-patent Document 6] Arzneimittel-Forschung, vol. 35, No. 7, p. 1025-1029 (1985)
[Non-patent Document 7] Chemische Berichte, vol. 117, No. 8, p. 2597-2614 (1984)
[Non-patent Document 8] Archiv der Pharmazie (Weinheim, Germany), vol. 317, No. 5, p. 455-459 (1984)
[Non-patent Document 9] Bioorganic & Medicinal Chemistry Letters, vol. 21, No. 10, p. 2898-2905 (2011)
[Non-patent Document 10] Chemical Communications, vol. 47, No. 19, p. 5596-5598 (2011)
[Non-patent Document 11] Bioorganic & Medicinal Chemistry Letters, vol. 21, No. 2, p. 818-823 (2011)
[Non-patent Document 12] Acta Crystallographica, Section E: Structure Reports Online, E66 (7), o1835-o1836 (2010)

DISCLOSURE OF INVENTION

Problems to be Solved by the Invention

The object of the present invention to provide novel compounds which have an effect of inhibiting amyloid β production. Especially, the present invention provides novel compounds which have a BACE1 inhibitory activity and a pharmaceutical composition comprising them.

Means for Solving the Problem

This invention relates to:
(1) A compound of the formula (I):

[Chemical Formula 1]

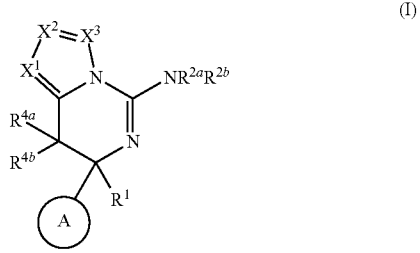

wherein ring A is a substituted or unsubstituted carbocycle or a substituted or unsubstituted heterocycle,
$X^1$—$X^2$=$X^3$ is $CR^5$—$CR^6$=$CR^7$, N—$CR^6$=$CR^7$, $CR^5$—N=$CR^7$ or $CR^5$—$CR^6$=N,
$R^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, substituted or unsubstituted carbocyclyl or substituted or unsubstituted heterocyclyl, $R^{2a}$ and $R^{2b}$ are each independently hydrogen, substituted or unsubstituted alkyl, substituted or unsubstituted acyl, substituted or unsubstituted alkoxycarbonyl or substituted or unsubstituted carbamoyl, $R^{4a}$, $R^{4b}$, $R^5$, $R^6$ and $R^7$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, and $R^{4a}$ and $R^{4b}$ together with the carbon atom to which they are attached may form a substituted or unsubstituted carbocycle or a substituted or unsubstituted heterocycle, provided that when $X^1$—$X^2$=$X^3$ is N—$CR^6$=$CR^7$ or $CR^5$—$CR^6$=N, then ring A is

[Chemical Formula 2]

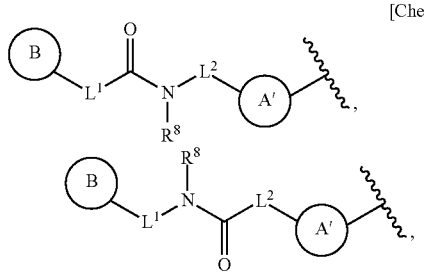

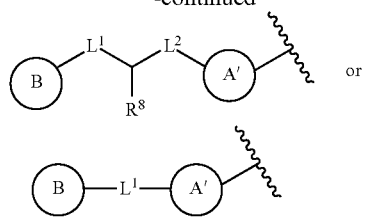

wherein $L^1$ and $L^2$ are each independently a bond, substituted or unsubstituted alkylene, substituted or unsubstituted alkenylene or substituted or unsubstituted alkynylene, ring A', ring B and ring B' are each independently a substituted or unsubstituted carbocycle or a substituted or unsubstituted heterocycle, provided that when $L^1$ is a bond, then ring B' is substituted or unsubstituted pyridine, substituted or unsubstituted pyrimidine or substituted or unsubstituted pyrazine, and $R^8$ is each independently hydrogen, hydroxy, substituted or unsubstituted alkyl, substituted or unsubstituted alkenyl, substituted or unsubstituted alkynyl or substituted or unsubstituted acyl, its pharmaceutically acceptable salt or a solvate thereof.

(2) The compound according to the above (1) wherein $X^1$—$X^2$=$X^3$ is $CR^5$—$CR^6$=$CR^7$ or $CR^5$—N=$CR^7$, its pharmaceutically acceptable salt or a solvate thereof.

(3) The compound according to the above (1) or (2) wherein ring A is

[Chemical Formula 3]

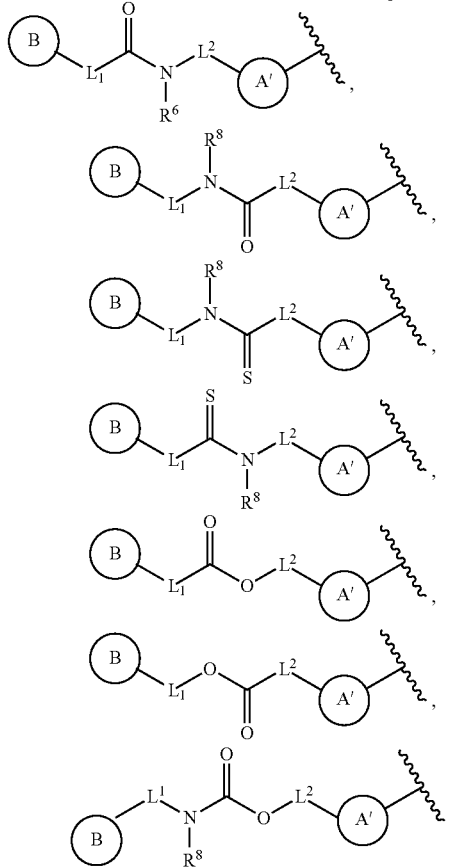

-continued

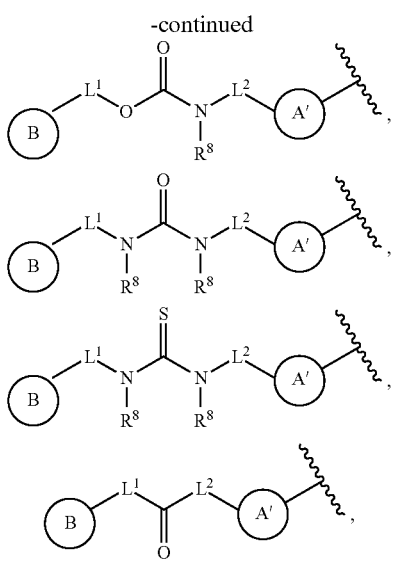

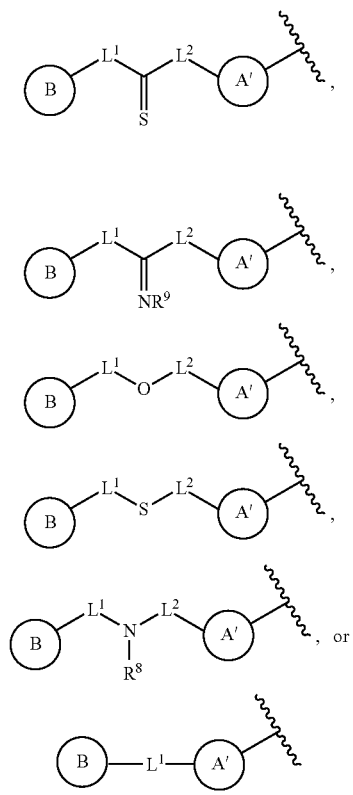

wherein ring A' and ring B are each independently a substituted or unsubstituted carbocycle or a substituted or unsubstituted heterocycle, $L^1$ and $L^2$ are each independently a bond, substituted or unsubstituted alkylene, substituted or unsubstituted alkenylene or substituted or unsubstituted alkynylene, and $R^8$ and $R^9$ are each independently hydrogen, hydroxy, substituted or unsubstituted alkyl, substituted or unsubstituted alkenyl, substituted or unsubstituted alkynyl or substituted or unsubstituted acyl, its pharmaceutically acceptable salt or a solvate thereof.

(4) The compound according to any one of the above (1) to (3) wherein ring A is

[Chemical Formula 4]

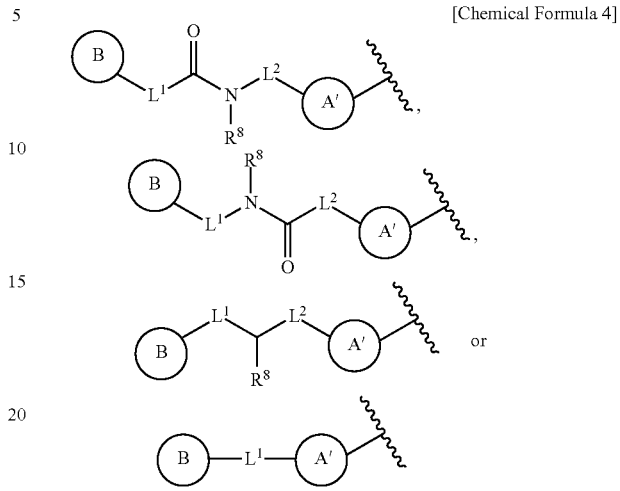

its pharmaceutically acceptable salt or a solvate thereof.

(5) The compound according to the above (3) or (4) wherein each of $L^1$ and $L^2$ is a bond, its pharmaceutically acceptable salt or a solvate thereof.

(6) The compound according to the above (1) wherein $X^1$—$X^2$=$X^3$ is N—$CR^6$=$CR^7$ or $CR^5$—$CR^6$=N, and ring A is

[Chemical Formula 5]

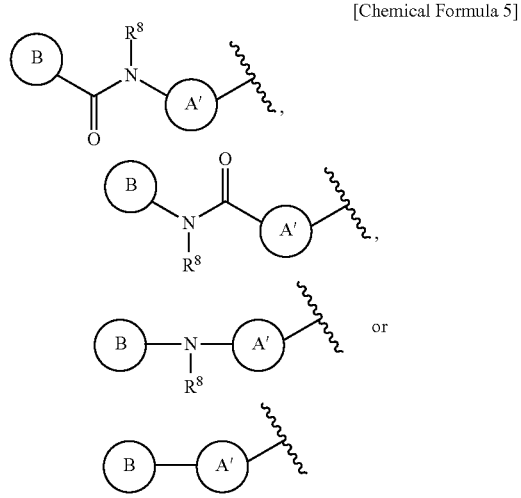

its pharmaceutically acceptable salt or a solvate thereof.

(7) The compound according to any one of the above (4) to (6) wherein ring A' is substituted or unsubstituted benzene or substituted or unsubstituted pyridine, and ring B or ring B' is substituted or unsubstituted pyridine, substituted or unsubstituted pyrimidine or substituted or unsubstituted pyrazine, its pharmaceutically acceptable salt or a solvate thereof.

(8) A pharmaceutical composition comprising the compound according to any one of the above (1) to (7), its pharmaceutically acceptable salt or a solvate thereof.

(9) A pharmaceutical composition having BACE1 inhibitory activity comprising the compound according to any one of the above (1) to (7), its pharmaceutically acceptable salt or a solvate thereof.

(10) A method for treating or preventing diseases related to BACE1 comprising administering the compound according to any one of the above (1) to (7) or its pharmaceutically acceptable salt thereof.

(11) Use of the compound according to any one of the above (1) to (7) or its pharmaceutically acceptable salt thereof for manufacturing a medicament for treating or preventing diseases related to BACE1.

(12) A compound according to any one of the above (1) to (7) or its pharmaceutically acceptable salt thereof for use in treating or preventing diseases related to BACE1.

(13) A method for inhibiting BACE1 activity comprising administering the compound according to any one of the above (1) to (7), its pharmaceutically acceptable salt or a solvate thereof.

(14) A compound according to any one of the above (1) to (7), its pharmaceutically acceptable salt or a solvate thereof for use in a method for inhibiting BACE1 activity.

(15) The pharmaceutical composition according to the above (8) or (9) which is a medicament for treating diseases induced by production, secretion or deposition of amyloid β proteins.

(16) A method for treating diseases induced by production, secretion or deposition of amyloid β proteins comprising administering the compound according to any one of the above (1) to (7), its pharmaceutically acceptable salt or a solvate thereof.

(17) A compound according to any one of the above (1) to (7), its pharmaceutically acceptable salt or a solvate thereof for use in a method for treating diseases induced by production, secretion or deposition of amyloid β proteins.

(18) The pharmaceutical composition according to the above (8) or (9) which is a medicament for treating Alzheimer's disease.

(19) A method for treating Alzheimer's disease comprising administering the compound according to any one of the above (1) to (7), its pharmaceutically acceptable salt or a solvate thereof.

(20) The compound according to any one of the above (1) to (7), its pharmaceutically acceptable salt or a solvate thereof for use in treating Alzheimer's disease.

(21) A method, a system, an apparatus, a kit or the like for manufacturing the compound according to any one of the above (1) to (7).

(22) A method, a system, an apparatus, a kit or the like for preparing the pharmaceutical composition comprising the compound according to any one of the above (1) to (7), its pharmaceutically acceptable salt or a solvate thereof.

(23) A method, a system, an apparatus, a kit or the like using the compound according to any one of the above (1) to (7), its pharmaceutically acceptable salt, or a solvate thereof.

Effect of the Invention

The compound of the present invention has BACE1 inhibitory activity and is useful as a medicament for treating and/or preventing disease induced by production, secretion or deposition of amyloid β protein such as Alzheimer's disease.

MODE FOR CARRYING OUT THE INVENTION

Each meaning of terms used herein is described below. In the present specification, unless otherwise noted, each term is used in the same meaning when used alone or in combination with other words.

In the present specification, the term "halogen" includes fluorine, chlorine, bromine, and iodine.

The halogen portions in "halogenoalkoxy", "halogenoalkyl" and "halogenoalkoxycarbonyl" are the same as the above "halogen".

In the present specification, the term "alkyl" includes linear or branched alkyl having a carbon number of 1 to 15, for example, a carbon number of 1 to 10, for example, a carbon number of 1 to 6, and for example, a carbon number of 1 to 3. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl.

The alkyl portions in "alkoxy", "halogenoalkyl", "halogenoalkoxy", "hydroxyalkoxy", "alkoxycarbonyl", "halogenoalkoxycarbonyl", "alkylamino", "aminoalkyl", "alkoxyalkoxy", "alkoxyalkenyloxy", "alkylcarbamoyl", "hydroxyalkylcarbamoyl", "alkoxyimino", "alkylthio", "alkylsulfonyl", "alkylsulfonylamino", "alkylsulfonylalkylamino", "alkylsulfonylimino", "alkylsulfinylamino", "alkylsulfinylalkylamino", "alkylsulfinylimino", "alkylsulfamoyl", "alkylsulfinyl", "carbocyclylalkyl", "carbocyclylalkoxy", "carbocyclylalkoxycarbonyl", "carbocyclylalkylamino", "carbocyclylalkylcarbamoyl", "cycloalkylalkyl", "cycloalkylalkoxy", "cycloalkylalkylamino", "cycloalkylalkoxycarbonyl", "cycloalkylalkylcarbamoyl", "arylalkyl", "arylalkoxy", "arylalkylamino", "arylalkoxycarbonyl", "arylalkylcarbamoyl", "heterocyclylalkyl", "heterocyclylalkoxy", "heterocyclylalkylamino", "heterocyclylalkoxycarbonyl" and "heterocyclylalkylcarbamoyl" are the same as the above "alkyl".

"Substituted or unsubstituted alkyl" may be substituted with one or more substituents selected from a substituent group α.

As used herein, the substituent group α is a group consisting of halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, carbocyclyl and heterocyclyl wherein each of the carbocycle and heterocycle may be substituted with one or more substituents selected from halogen, alkyl, hydroxy and alkoxy.

Examples of the substituent of "substituted or unsubstituted alkoxy", "substituted or unsubstituted alkoxycarbonyl", "substituted or unsubstituted alkylthio", "substituted or unsubstituted alkylsulfinyl" and "substituted or unsubstituted alkylsulfonyl" are one or more substituents selected from the substituent group α.

Examples of "halogenoalkyl" are trifluoromethyl, fluoromethyl and trichloromethyl.

The term "alkylidene" includes a divalent group of the above "alkyl" and examples include methylidene, ethylidene, propylidene, isopropylidene, butylidene, pentylidene and hexylidene.

The term "alkenyl" includes linear or branched alkenyl having a carbon number of 2 to 15, for example, a carbon number of 2 to 10, for example, a carbon number of 2 to 6, and for example, a carbon number of 2 to 4, having one or more double bonds at any position. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

The term "alkynyl" includes linear or branched alkynyl having a carbon number of 2 to 10, for example, a carbon number of 2 to 8, for example, a carbon number 3 to 6, having one or more triple bonds at any position. Examples include ethynyl, propynyl, butynyl, pentynyl, hexynyl, heptynyl, octynyl, nonynyl and decynyl. These may have further a double bond at any position.

The alkenyl portions in "alkenyloxy", "alkenyloxycarbonyl", "alkoxyalkenyloxy", "alkenylthio", "alkenylsulfinyl", "alkenylsulfonyl", and "alkenylamino" are the same as the above "alkenyl".

The alkynyl portions in "alkynyloxy", "alkynyloxycarbonyl", "alkoxyalkynyloxy", "alkynylthio", "alkynylamino", "alkynylsulfinyl" and "alkynylsulfonyl" are the same as the above "alkynyl".

Examples of the substituent of "substituted or unsubstituted alkenyl", "substituted or unsubstituted alkenyloxy", "substituted or unsubstituted alkenylthio", "substituted or unsubstituted alkenyloxycarbonyl", "substituted or unsubstituted alkenylsulfinyl", "substituted or unsubstituted alkenylsulfonyl", "substituted or unsubstituted alkynyl", "substituted or unsubstituted alkynyloxy", "substituted or unsubstituted alkynyloxycarbonyl", "substituted or unsubstituted alkynylthio", "substituted or unsubstituted alkynylsulfinyl", and "substituted or unsubstituted alkynylsulfonyl" are one or more substituents selected form the substituent group α.

Examples of the substituents of "substituted or unsubstituted amino", "substituted or unsubstituted carbamoyl", "substituted or unsubstituted thiocarbamoyl", and "substituted or unsubstituted sulfamoyl" are one or two substituents selected from alkyl, acyl, hydroxy, alkoxy, alkoxycarbonyl, carbocyclyl, and heterocyclyl.

The term "acyl" includes formyl, alkylcarbonyl, alkenylcarbonyl, alkynylcarbonyl, carbocyclylcarbonyl, and heterocyclylcarbonyl. Examples are formyl, acetyl, propionyl, butyryl, isobutyryl, valeryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolecarbonyl, pyrazinecarbonyl, piperidinecarbonyl and thiomorpholino.

The acyl portions in "acyloxy" and "acylamino" are the same as the above "acyl".

Examples of the substituents of "substituted or unsubstituted acyl" and "substituted or unsubstituted acyloxy" are one or more substituents selected from the substituent group α. The ring portions of carbocyclylcarbonyl and heterocyclylcarbonyl may be substituted with one or more substituents selected from alkyl, the substituent group α, and alkyl substituted with one or more substituents selected from the substituent group α.

The term "carbocyclyl" includes cycloalkyl, cycloalkenyl, aryl and non-aromatic fused carbocyclyl.

The term "cycloalkyl" includes carbocyclyl having a carbon number of 3 to 10, for example, a carbon number of 3 to 8, and for example, a carbon number 4 to 8. Examples are cyclopropyl, cyclobutyl, cyclopentyl, cyclohexyl, cycloheptyl, cyclooctyl, cyclononyl and cyclodecyl.

The cycloalkyl portions in "cycloalkylalkyl", "cycloalkyloxy", "cycloalkylalkoxy", "cycloalkylthio", "cycloalkylamino", "cycloalkylalkylamino", "cycloalkylsulfamoyl", "cycloalkylsulfonyl", "cycloalkylcarbamoyl", "cycloalkylalkylcarbamoyl", "cycloalkylalkoxycarbonyl" and "cycloalkyloxycarbonyl" are the same as the above "cycloalkyl".

The term "cycloalkenyl" includes a group having one or more double bonds at any position in the ring of the above "cycloalkyl". Examples are cyclopropenyl, cyclobutenyl, cyclopentenyl, cyclohexenyl, cycloheptynyl, cyclooctynyl and cyclohexadienyl.

The term "aryl" includes phenyl, naphthyl, anthryl and phenanthryl. Specific example is phenyl.

The term "non-aromatic fused carbocyclyl" includes non-aromatic groups wherein two or more rings selected from the above "cycloalkyl", "cycloalkenyl" and "aryl" are fused. Examples are indanyl, indenyl, tetrahydronaphthyl and fluorenyl.

The carbocycle portions in "carbocycle", "carbocyclyloxy", "carbocyclylalkyl", "carbocyclylalkoxy", "carbocyclylalkoxycarbonyl", "carbocyclylthio", "carbocyclylamino", "carbocyclylalkylamino", "carbocyclylcarbonyl", "carbocyclylsulfamoyl", "carbocyclylsulfinyl", "carbocyclylsulfonyl", "carbocyclylcarbamoyl", "carbocyclylalkylcarbamoyl", and "carbocyclyloxycarbonyl" are the same as the above "carbocyclyl".

The aryl portions in "arylalkyl", "aryloxy", "aryloxycarbonyl", "arylalkoxycarbonyl", "arylthio", "arylamino", "arylalkoxy", "arylalkylamino", "arylsulfonyl", "arylsulfamoyl", "arylcarbamoyl" and "arylalkylcarbamoyl" are the same as the above "aryl".

The term "heterocyclyl" includes a heterocyclic group comprising one or more rings and having one or more same or different hetero atoms arbitrarily selected from O, S, and N in the ring. Specific examples are 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl;

non-aromatic heterocyclyl such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydropyrimidinyl, hexahydroazepinyl, tetrahydrodiazepinyl, tetrahydropyridazinyl, dioxolanyl, dioxazinyl, aziridinyl, dioxolinyl, oxepanyl, thiolanyl, thiinyl, and thiazinyl;

fused bicyclic heterocyclyl such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, imidazopyrazolyl, pyrazolopyridyl, pyrazolopyrazinyl, thiazolopyridyl, pyrazolopyrimidinyl, pyrazolotriazinyl, pyridazolopyridyl, triazolopyridyl, imidazothiazolyl, pyrazinopyridazinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxinyl, dihydrobenzoxezinyl, dihydrobenzodioxepinyl, and dihydrothienodioxinylJ fused tricyclic heterocyclyl such as carbazolyl, acridinyl, xanthenyl, phenothiazinyl, phenoxathiinyl, phenoxazinyl, dibenzofuryl, imidazoquinolyl, and tetrahydrocarbazolyl. Specific examples are 5- or 6-membered heteroaryl and non-aromatic heterocyclyl.

The heterocycle portions in "heterocycle", "heterocyclylalkyl", "heterocyclyloxy", "heterocyclylthio", "heterocyclylcarbonyl", "heterocyclyloxycarbonyl", "heterocyclylalkoxy", "heterocyclylamino", "heterocyclylsulfamoyl", "heterocyclylsulfinyl", "heterocyclylsulfonyl", "heterocyclylcarbamoyl", "heterocyclyloxycarbonyl", "heterocyclylalkylamino", "heterocyclylalkoxycarbonyl" and "heterocyclylalkylcarbamoyl" are the same as the above "heterocyclyl".

A bond of the above "heterocyclyl" may be situated on any ring.

The term "heteroaryl" includes aromatic cyclic groups among the above "heterocyclyl".

In the present specification, examples of "ring A" are groups of the following formulas:

[Chemical Formula 6]

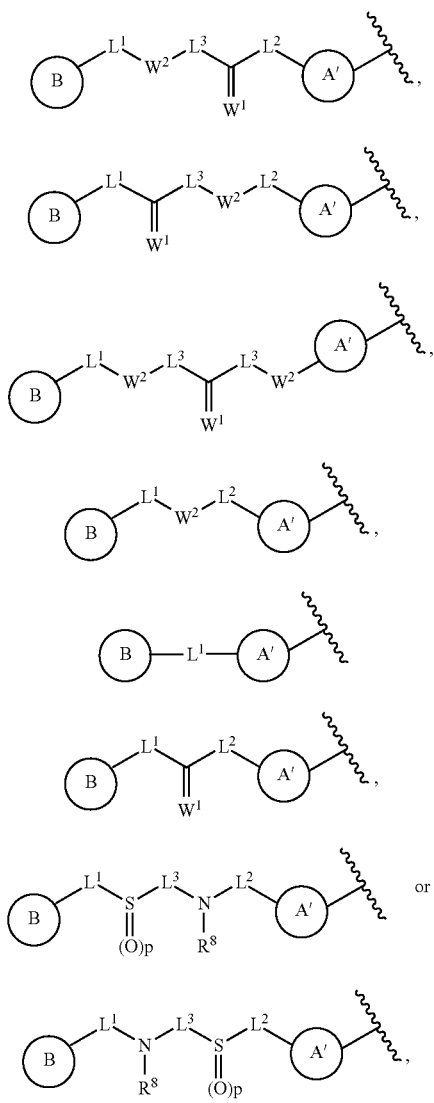

wherein ring A' and ring B are each independently a substituted or unsubstituted carbocycle or a substituted or unsubstituted heterocycle, $L^1$, $L^2$, and $L^3$ are each independently a bond, substituted or unsubstituted alkynylene, substituted or unsubstituted alkenylene or substituted or unsubstituted alkynylene, $=W^1$ is $=O$, $=S$, or $=NR^9$, $W^2$ is O, S, or $NR^8$, $R^8$ is hydrogen, substituted or unsubstituted alkyl, substituted or unsubstituted alkenyl, substituted or unsubstituted alkynyl or substituted or unsubstituted acyl, $R^9$ is hydrogen, hydroxy, substituted or unsubstituted alkyl, substituted or unsubstituted alkenyl, substituted or unsubstituted alkynyl or substituted or unsubstituted acyl, when ring A is (i), then the constituent carbon atom of $L^1$ and the constituent carbon atom of $L^2$, or the nitrogen atom of $W^2$ and the constituent carbon atom of $L^2$ may be connected with substituted or unsubstituted alkylene to form a ring, when ring A is (ii), then the constituent carbon atom of $L^1$ and the constituent carbon atom of $L^2$, or the constituent carbon atom of $L^1$ and the nitrogen atom of $W^2$ may be connected with substituted or unsubstituted alkylene to form a ring, when ring A is then two nitrogen atoms of $W^2$ may be connected with substituted or unsubstituted alkylene to form a ring, when ring A is (vi), then the constituent carbon atom of $L^1$ and the constituent carbon atom of $L^2$ may be connected by substituted or unsubstituted alkylene to form a ring, p is 1 or 2, and when multiple $L^3$, multiple $W^2$, multiple $R^9$ or multiple $R^{11}$ are present, each of them may be independently different.

Specific examples are as follows:

[Chemical Formula 7]

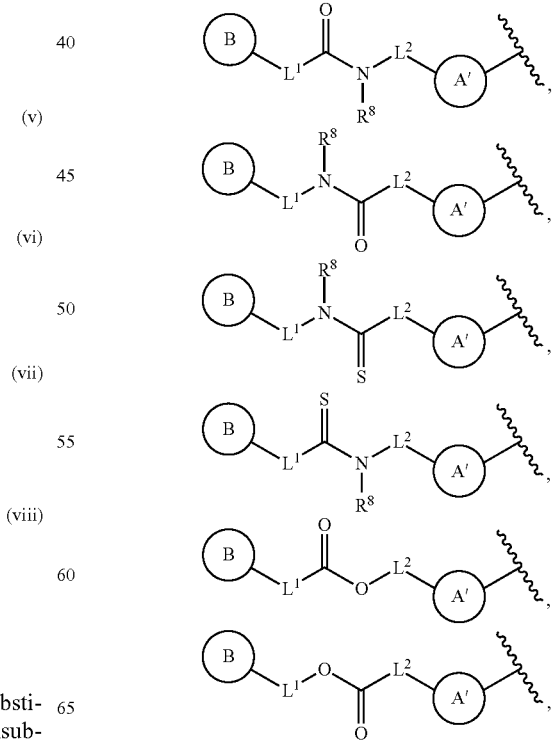

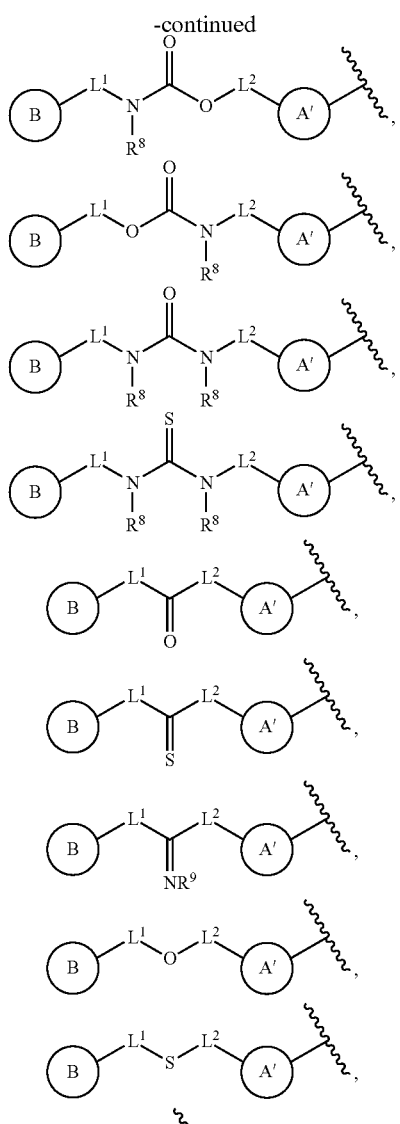

[Chemical Formula 8]

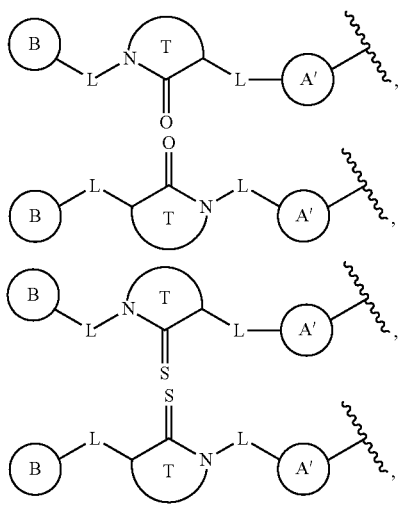

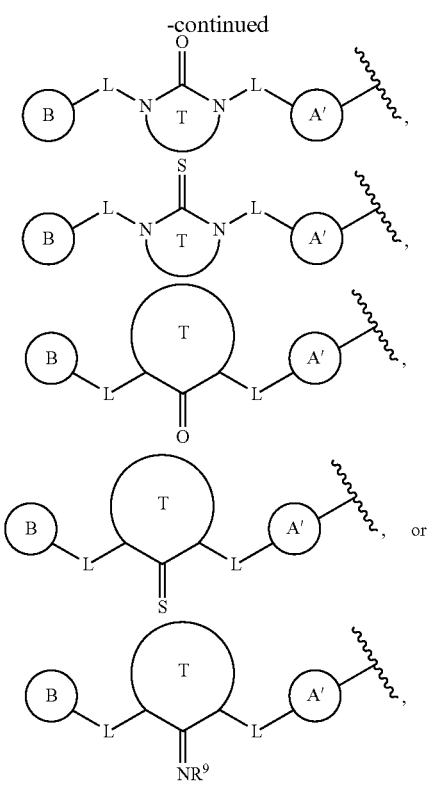

wherein L is each independently a bond, substituted or unsubstituted alkylene, substituted or unsubstituted alkenylene or substituted or unsubstituted alkynylene, ring T is a 5- or 6-membered ring optionally substituted with one or more substituents selected from the substituent group α and other symbols are the same as defined above.

More specific examples are as follows:

[Chemical Formula 9]

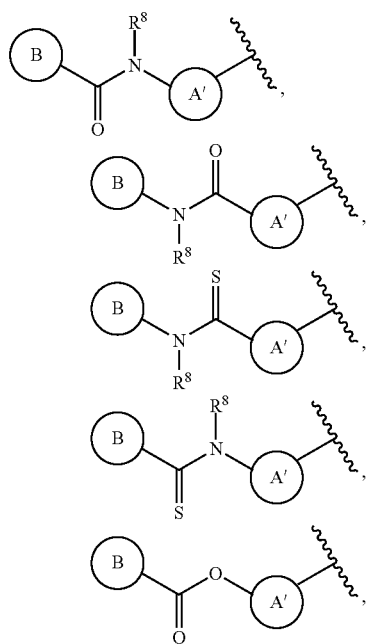

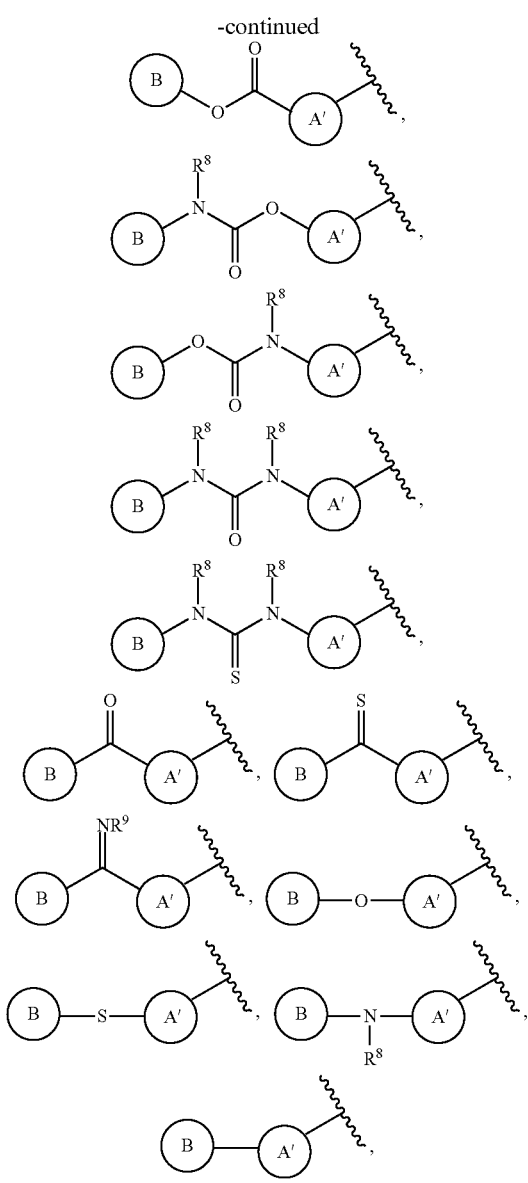
wherein each symbol is the same as defined above.
[Chemical Formula 10]
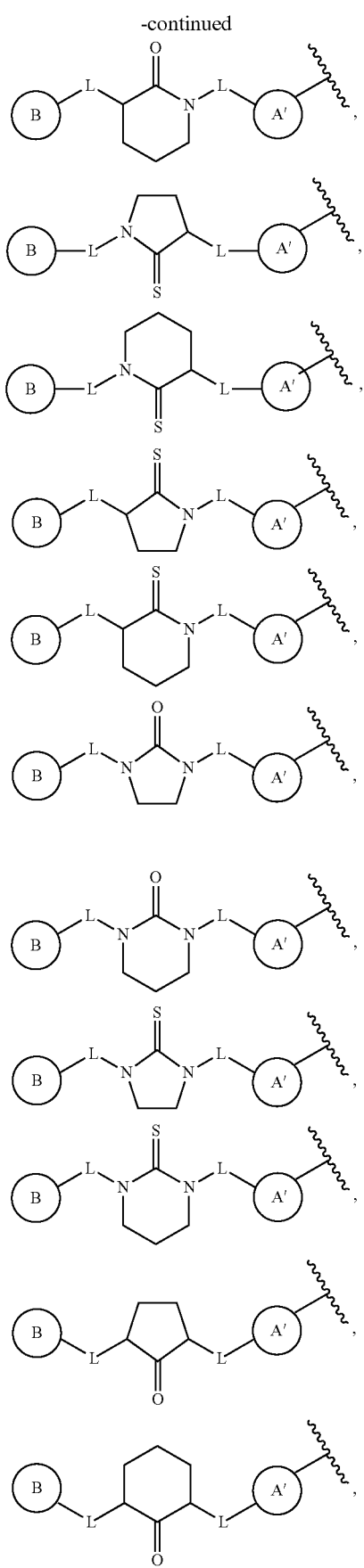

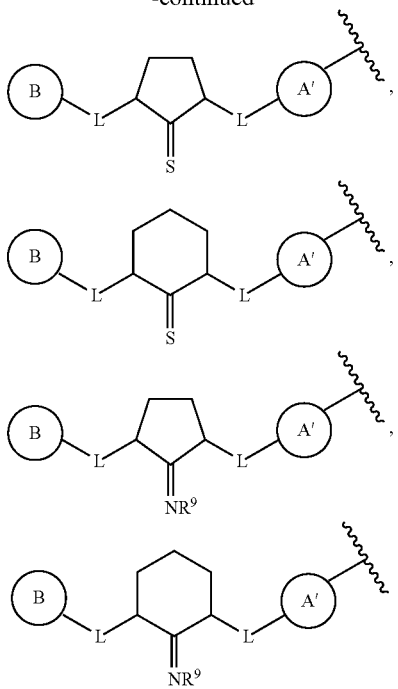

wherein each symbol is the same as defined above.

Other examples of the substituent of "substituted or unsubstituted carbocycle", "substituted or unsubstituted heterocycle", "substituted or unsubstituted benzene", "substituted or unsubstituted pyridine", "substituted or unsubstituted pyrimidine", and "substituted or unsubstituted pyrazine" as ring A and ring B include:

a group selected from the substituent group α such as halogen, hydroxy, alkoxy, acyl, acyloxy, carboxy, alkoxycarbonyl, carbamoyl, amino, cyano, alkylamino and/or alkylthio; alkyl substituted with one or more substituents selected from the substituent group α, hydroxyimino and alkoxyimino, wherein the substituent is, for example, halogen, hydroxy, alkoxy and/or alkoxycarbonyl; or unsubstituted alkyl;

aminoalkyl substituted with one or more substituents selected from the substituent group α; wherein the substituent is, for example, acyl, alkyl and/or alkoxy;

alkenyl substituted with one or more substituents selected from the substituent group α, wherein the substituent is, for example, alkoxycarbonyl, halogen, and/or halogenoalkoxycarbonyl; or unsubstituted alkenyl;

alkynyl substituted with one or more substituents selected from the substituent group α, wherein the substituent is, for example, alkoxycarbonyl; or unsubstituted alkynyl;

alkoxy substituted with one or more substituents selected from the substituent group α, wherein the substituent is, for example, halogen, carbamoyl, alkylcarbamoyl and/or hydroxyalkylcarbamoyl;

alkoxyalkoxy substituted with one or more substituents selected from the substituent group α;

alkenyloxy substituted with one or more substituents selected from the substituent group α, wherein the substituent is, for example, halogen, hydroxy, amino and/or alkylamino; or unsubstituted alkenyloxy;

alkoxyalkenyloxy substituted with one or more substituents selected from the substituent group α;

alkynyloxy substituted with one or more substituents selected from the substituent group α, wherein the substituent is, for example, halogen and/or hydroxy; or unsubstituted alkynyloxy;

alkoxyalkynyloxy substituted with one or more substituents selected from the substituent group α, alkylthio substituted with one or more substituents selected from the substituent group α; or unsubstituted alkylthio;

alkenylthio substituted with one or more substituents selected from the substituent group α; or unsubstituted alkenylthio;

alkynylthio substituted with one or more substituents selected from the substituent group α; or unsubstituted alkynylthio;

alkylamino substituted with one or more substituents selected from the substituent group α;

alkenylamino substituted with one or more substituents selected from the substituent group α;

alkynylamino substituted with one or more substituents selected from the substituent group α;

aminooxy substituted with one or more substituents selected from the substituent group α and alkylidene; or unsubstituted aminooxy;

acyl substituted with one or more substituents selected from the substituent group α;

alkylsulfonyl substituted with one or more substituents selected from the substituent group α; or unsubstituted alkylsulfonyl;

alkylsulfinyl substituted with one or more substituents selected from the substituent group α; or unsubstituted alkylsulfinyl;

alkylsulfamoyl substituted with one or more substituents selected from the substituent group α;

carbocyclyl such as cycloalkyl and aryl, substituted with one or more substituents selected from the substituent group α, azide, alkyl and halogenoalkyl;

heterocyclyl substituted with one or more substituents selected from the substituent group α, azide, alkyl and halogenoalkyl;

carbocyclylalkyl such as cycloalkylalkyl and arylalkyl, substituted with one or more substituents selected from the substituent group α, azide, alkyl and halogenoalkyl; or unsubstituted carbocyclylalkyl, heterocyclylalkyl substituted with one or more substituents selected from the substituent group α, azide, alkyl and halogenoalkyl; or unsubstituted heterocyclylalkyl;

carbocyclyloxy such as cycloalkyloxy and aryloxy, substituted with one or more substituents selected from the substituent group α, azide, alkyl and halogenoalkyl; or unsubstituted carbocyclyloxy such as cycloalkyloxy and aryloxy;

heterocyclyloxy substituted with one or more substituents selected from the substituent group α, azide, alkyl and halogenoalkyl; or unsubstituted heterocyclyloxy;

carbocyclylalkoxy such as cycloalkylalkoxy and arylalkoxy, substituted with one or more substituents selected from the substituent group α, azide, alkyl and halogenoalkyl, or unsubstituted carbocyclylalkoxy such as cycloalkylalkoxy and arylalkoxy;

heterocyclylalkoxy substituted with one or more substituents selected from the substituent group α, azide, alkyl and halogenoalkyl, or unsubstituted heterocyclylalkoxy;

carbocyclylalkoxycarbonyl such as cycloalkylalkoxycarbonyl and arylalkoxycarbonyl, substituted with one or more substituents selected from the substituent group α, azide, alkyl and halogenoalkyl; or unsubstituted carbocyclylalkoxycarbonyl such as cycloalkylalkoxycarbonyl and arylalkoxycarbonyl;

heterocyclylalkoxycarbonyl substituted with one or more substituents selected from the substituent group α, azide, alkyl and halogenoalkyl; or unsubstituted heterocyclylalkoxycarbonyl;

carbocyclylthio such as cycloalkylthio and arylthio, substituted with one or more substituents selected from the substituent group α, azide, alkyl and halogenoalkyl; or unsubstituted carbocyclylthio such as cycloalkylthio and arylthio;

heterocyclylthio substituted with one or more substituents selected from the substituent group α, azide, alkyl and halogenoalkyl; or unsubstituted heterocyclylthio;

carbocyclylamino such as cycloalkylamino and arylamino, substituted with one or more substituents selected from the substituent group α, azide, alkyl and halogenoalkyl; or unsubstituted carbocyclylamino such as cycloalkylamino and arylamino; heterocyclylamino substituted with one or more substituents selected from the substituent group α, azide, alkyl and halogenoalkyl; or unsubstituted heterocyclylamino;

carbocyclylalkylamino such as cycloalkylalkylamino and arylalkylamino, substituted with one or more substituents selected from the substituent group α, azide, alkyl and halogenoalkyl; or unsubstituted carbocyclylalkylamino such as cycloalkylalkylamino and arylalkylamino;

heterocyclylalkylamino substituted with one or more substituents selected from the substituent group α, azide, alkyl and halogenoalkyl; or unsubstituted heterocyclylalkylamino;

carbocyclylsulfamoyl such as cycloalkylsulfamoyl and arylsulfamoyl, substituted with one or more substituents selected from the substituent group α, azide, alkyl and halogenoalkyl; or unsubstituted carbocyclylsulfamoyl;

heterocyclylsulfamoyl substituted with one or more substituents selected from the substituent group α, azide, alkyl and halogenoalkyl; or unsubstituted heterocyclylsulfamoyl;

carbocyclylsulfonyl such as cycloalkylsulfonyl and arylsulfonyl, substituted with one or more substituents selected from the substituent group α, azide, alkyl and halogenoalkyl; or unsubstituted carbocyclylsulfonyl such as cycloalkylsulfonyl and arylsulfonyl;

heterocyclylsulfonyl substituted with one or more substituents selected from the substituent group α, azide, alkyl and halogenoalkyl; or unsubstituted heterocyclylsulfonyl;

carbocyclylcarbamoyl such as cycloalkylcarbamoyl and arylcarbamoyl, substituted with one or more substituents selected from the substituent group α, azide, alkyl and halogenoalkyl; or unsubstituted carbocyclylcarbamoyl such as cycloalkylcarbamoyl and arylcarbamoyl;

heterocyclylcarbamoyl substituted with one or more substituents selected from the substituent group α, azide, alkyl and halogenoalkyl; or unsubstituted heterocyclylcarbamoyl;

carbocyclylalkylcarbamoyl such as cycloalkylalkylcarbamoyl and arylalkylcarbamoyl, substituted with one or more substituents selected from the substituent group α, azide, alkyl and halogenoalkyl; or unsubstituted carbocyclylalkylcarbamoyl such as cycloalkylalkylcarbamoyl and arylalkylcarbamoyl;

heterocyclylalkylcarbamoyl substituted with one or more substituents selected from the substituent group α, azide, alkyl and halogenoalkyl; or unsubstituted heterocyclylalkylcarbamoyl;

carbocyclyloxycarbonyl such as cycloalkyloxycarbonyl and aryloxycarbonyl, substituted with one or more substituents selected from the substituent group α, azide, alkyl and halogenoalkyl; or unsubstituted carbocyclyloxycarbonyl such as cycloalkyloxycarbonyl and aryloxycarbonyl;

heterocyclyloxycarbonyl substituted with one or more substituents selected from the substituent group α, azide, alkyl and halogenoalkyl; or unsubstituted heterocyclyloxycarbonyl;

alkylenedioxy substituted with halogen; or unsubstituted alkylenedioxy;

oxo; azido. The aforementioned ring of ring A and ring B each may be substituted with one or more substituents selected from the above substituents.

Examples of the substituent of "a substituted or unsubstituted carbocycle", "substituted or unsubstituted benzene", "a substituted or unsubstituted heterocycle", "substituted or unsubstituted pyridine", "substituted or unsubstituted pyrimidine" and "substituted or unsubstituted pyrazine" as ring A' and ring B include one or more selected from halogen, cyano, hydroxy, nitro, carboxy, alkyl substituted with one or more substituents selected from the substituent group α, unsubstituted alkyl, alkoxy substituted with one or more substituents selected from the substituent group α, unsubstituted alkoxy, amino substituted with one or more substituents selected from the substituent group α, unsubstituted amino, carbamoyl substituted with one or more substituents selected from the substituent group α, unsubstituted carbamoyl, alkoxycarbonyl substituted with one or more substituents selected from the substituent group α, and unsubstituted alkoxycarbonyl.

Examples of the substituent of "a substituted or unsubstituted carbocycle", "substituted or unsubstituted benzene", "a substituted or unsubstituted heterocycle", and "substituted or unsubstituted pyridine" as ring A' include one or more substituents selected from halogen, hydroxy, alkyl, alkenyl, alkynyl, alkoxy, alkenyloxy, alkynyloxy, acyl, carboxy, alkoxycarbonyl, amino and cyano.

Specific example is halogen.

Examples of the substituent of "a substituted or unsubstituted carbocycle", "substituted or unsubstituted benzene", "a substituted or unsubstituted heterocycle", "substituted or unsubstituted pyridine", "substituted or unsubstituted pyrimidine", and "substituted or unsubstituted pyrazine" as ring B are one or more substituents selected from halogen, alkyl, alkenyl, alkynyl, alkoxy, alkenyloxy, alkynyloxy and cyano.

Examples of the substituent of "substituted or unsubstituted carbocyclyl", "substituted or unsubstituted heterocyclyl", "substituted or unsubstituted carbocyclylalkyl", "substituted or unsubstituted carbocyclylalkoxy", "substituted or unsubstituted carbocyclyloxy", "substituted or unsubstituted carbocyclylthio", "substituted or unsubstituted carbocyclyloxycarbonyl", "substituted or unsubstituted carbocyclylsulfinyl", "substituted or unsubstituted carbocyclylsulfonyl", "substituted or unsubstituted heterocyclyloxy", "substituted or unsubstituted heterocyclylthio", "substituted or unsubstituted heterocyclylalkyl", "substituted or unsubstituted heterocyclylalkoxy", "substituted or unsubstituted heterocyclyloxycarbonyl", "substituted or unsubstituted heterocyclylsulfinyl", "substituted or unsubstituted heterocyclylsulfonyl", "a substituted or unsubstituted carbocycle" and "substituted or unsubstituted heterocycle" as other than the above ring A, ring A' and ring B include one or more substituents selected from the substituent group α, unsubstituted alkyl, and alkyl substituted with one or more substituents selected from the substituent group α.

The term "alkylene" includes a linear or branched divalent carbon chain having a carbon number of 1 to 10, for example, a carbon number of 1 to 6, or a carbon number of 1 to 3. Examples include methylene, dimethylene, trimethylene, tetramethylene, and methyltrimethylene.

The alkylene portion in "alkylenedioxy" is the same as the above "alkylene".

The term "alkenylene" includes a linear or branched divalent carbon chain having a carbon number of 2 to 10, for example, a carbon number of 2 to 6, or a carbon number of 2 to 4, having a double bond at any position. Examples include vinylene, propenylene, butenylene, butadienylene, methylpropenylene, pentenylene and hexenylene.

The term "alkynylene" includes a linear or branched divalent carbon chain having a carbon number of 2 to 10, for example, a carbon number of 2 to 6, or a carbon number of 2 to 4, having a triple bond at any position and, further, optionally having a double bond. Examples include ethynylene, propynylene, butynylene, pentynylene and hexynylene.

Examples of the substituents of "substituted or unsubstituted alkylene", "substituted or unsubstituted alkenylene", and "substituted or unsubstituted alkynylene" include one or more substituents selected from the substituent group α, and specific examples are halogen and hydroxy.

The phrase "$R^{4a}$ and Rob together with the carbon atom to which they are attached may form a substituted or unsubstituted carbocycle or a substituted or unsubstituted heterocycle" includes

[Chemical Formula 11]

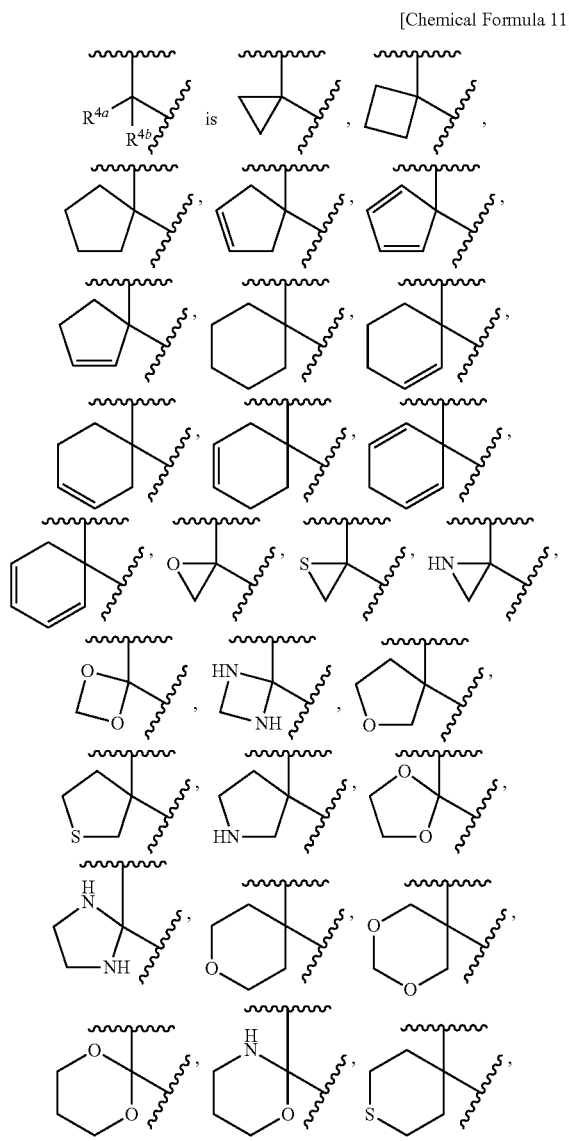

These are optionally substituted with one or more substituents selected from unsubstituted alkyl, the substituent group α and alkyl substituted with one or more selected from the substituent group α at any position.

The compound of the formula (I) is not limited to a specific isomer, and includes all possible isomers such as keto-enol isomers, imine-enamine isomers, diastereoisomers, optical isomers and rotation isomers, racemate and the mixture thereof. For example, the compound of the formula (I) wherein $R^{2a}$ is hydrogen includes the following tautomers.

[Chemical Formula 12]

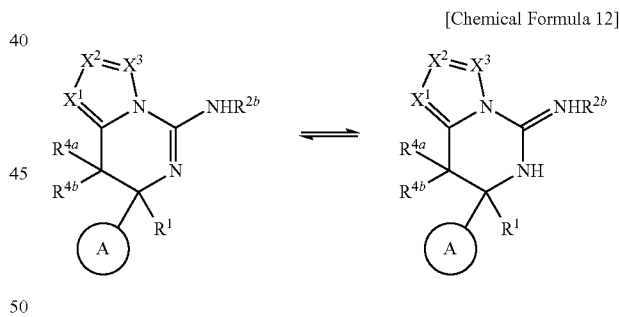

The compound of the formula (I) has an asymmetric carbon atom and includes the following optical isomers.

[Chemical Formula 13]

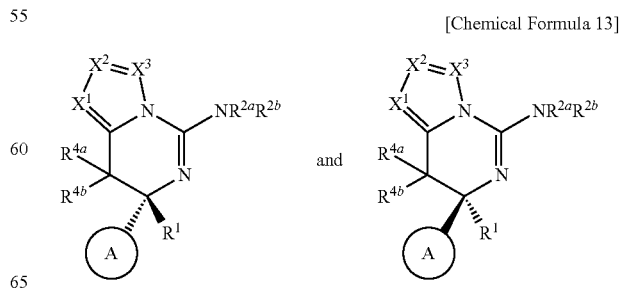

Preferable isomer is as follows.

[Chemical Formula 14]

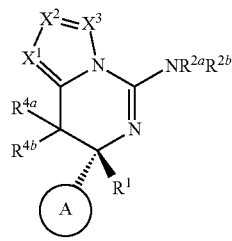

The optical isomer of the compound of the formula (I) can be obtained by known methods such as chiral chromatography or diastereomer salt formation using an optical active acid or base.

One or more hydrogens, carbons and/or other atoms of the compound of the formula (I) can be replaced by isotopes of the hydrogens, carbons and/or other atoms. Examples of isotopes include ones of hydrogen, carbon, nitrogen, oxygen, phosphorous, sulfur, fluorine, iodine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl, respectively. The compound of the formula (I) also includes the compound replaced by such isotopes. The compound replaced by such isotopes is useful also as a medicament, and includes all the radiolabeled compounds of the compound of the formula (I). The invention includes "radio-labelling method" for manufacturing the "radiolabeled compound" and the method is useful as a tool of metabolic pharmacokinetic research, the research in binding assay and/or diagnosis.

Radiolabeled compounds of the compound of the formula (I) can be prepared by methods known in the art. For example, tritiated compounds of the formula (I) can be prepared by introducing tritium into the particular compound of the formula (I) such as by catalytic dehalogenation with tritium. This method may include reacting a suitably halogen-substituted precursor of the compound of the formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

As pharmaceutically acceptable salt of the compound of the formula (I), examples include salts with alkaline metals (e.g. lithium, sodium and potassium), alkaline earth metals (e.g. calcium and barium), magnesium, transition metal (e.g. zinc and iron), ammonia, organic bases (e.g. trimethylamine, triethylamine, dicyclohexylamine, ethanolamine, diethanolamine, triethanolamine, meglumine, diethanolamine, ethylenediamine, pyridine, picoline, quinoline), and amino acids, and salts with inorganic acids (e.g. hydrochloric acid, sulfuric acid, nitric acid, carbonic acid, hydrobromic acid, phosphoric acid and hydroiodic acid) and organic acids (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid and ethanesulfonic acid). Specific examples are salts with hydrochloric acid, sulfuric acid, phosphoric acid, tartaric acid, or methanesulfonic acid. These salts may be formed by usual methods.

The compound of the formula (I) or its pharmaceutically acceptable salt may form solvate such as hydrate, and/or crystalline polymorphism, and the present invention also includes such various kinds of solvate and crystalline polymorphism. The "solvate" includes the compound of the formula (I) which coordinate arbitrary number of solvent molecules such as water molecules. The compound of the formula (I) or its pharmaceutically acceptable salt can adhere water or form hydrate by absorbing water molecules after leaving in the atmosphere. Moreover, the compound of the formula (I) or its pharmaceutically acceptable salt can form the crystalline polymorphism by recrystallization.

The compound of the formula (I) of the present invention or its pharmaceutically acceptable salt may form prodrug, and the present invention also includes such various kinds of prodrug. Prodrug is a derivative of the compound of the present invention having a group which can be chemically or metabolically decomposed and the one which becomes a pharmaceutically active compound of the present invention by solvolysis or physiological conditions in vivo. Prodrug includes a compound which converts into the compound of the formula (I) by enzymatical oxidation, reduction, hydrolysis or the like under physiological conditions in a living body, and a compound which converts into the compound of the formula (I) by hydrolyzing by stomach acid or the like. The method of selecting suitable prodrug derivatives and the method of manufacturing them are disclosed in Design of Prodrugs, Elsevier, and Amsterdam 1985. Prodrug itself may possess the activity.

When the compound of the formula (I) or its pharmaceutically acceptable salt has a hydroxy group, examples of the prodrug includes acyloxy derivatives and sulfonyloxy derivatives which can be prepared by reacting a compound having a hydroxy group with a suitable acid halide, suitable acid anhydride, suitable sulfonyl chloride, suitable sulfonylanhydride or mixed anhydride, or by reacting with a condensation agent. For example, $CH_3COO-$, $C_2H_5COO-$, t-BuCOO—, $C_{15}H_{31}COO-$, PhCOO—, COO(m-NaOOCPh)-, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$—O-$PhSO_3-$, $PhSO_3-$, and p-$CH_3PhSO_3-$ are exemplified.

The compound of the formula (I) includes the compound of the following formulas (Ia) to (Id).

[Chemical Formula 15]

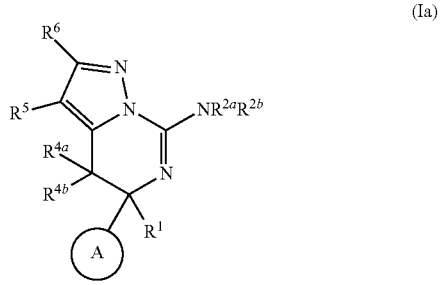

(Ia)

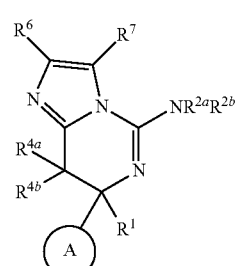

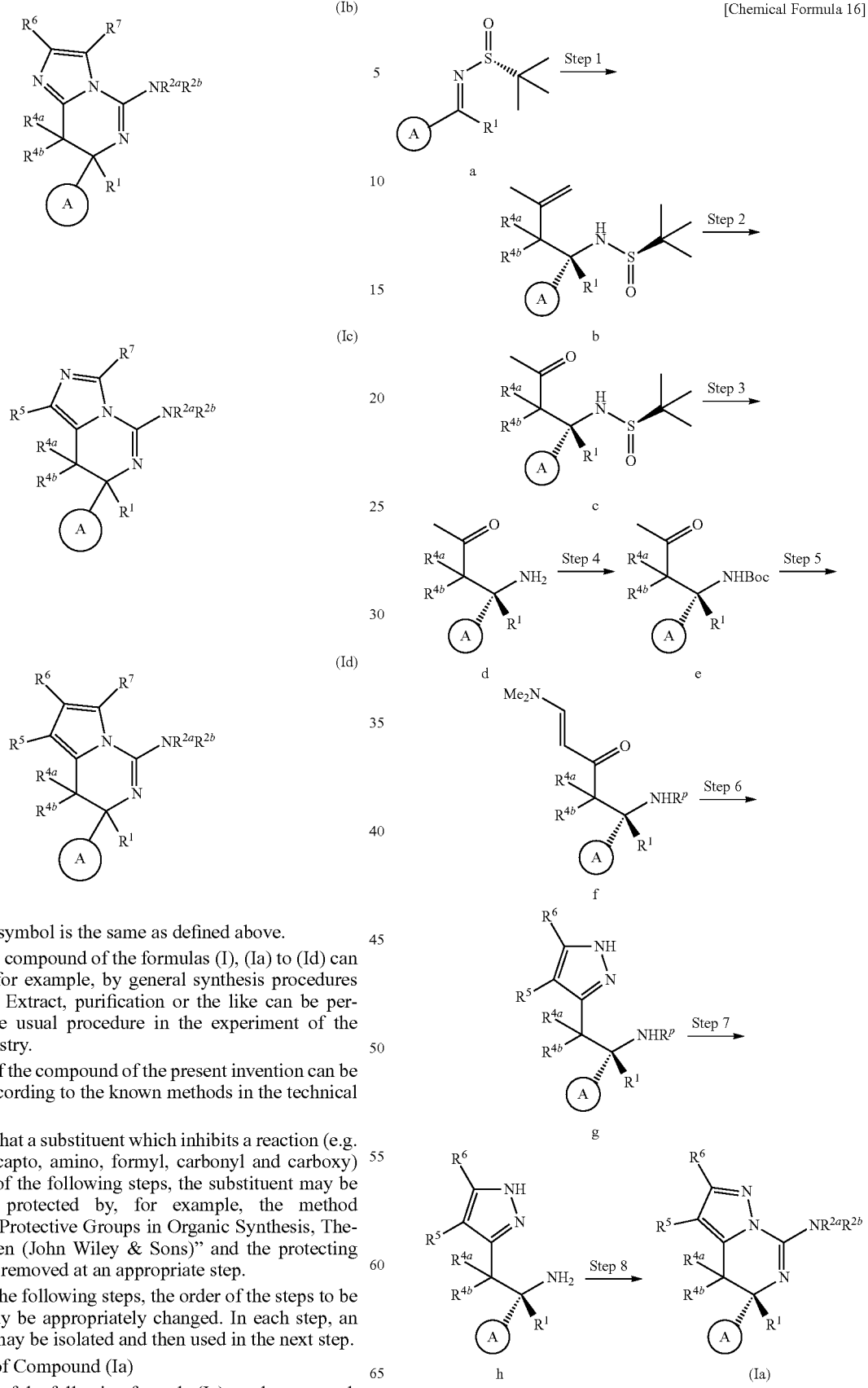

wherein each symbol is the same as defined above.

The present compound of the formulas (I), (Ia) to (Id) can be prepared, for example, by general synthesis procedures shown below. Extract, purification or the like can be performed by the usual procedure in the experiment of the organic chemistry.

Synthesis of the compound of the present invention can be carried out according to the known methods in the technical field.

In the case that a substituent which inhibits a reaction (e.g. hydroxy, mercapto, amino, formyl, carbonyl and carboxy) exists in any of the following steps, the substituent may be preliminarily protected by, for example, the method described in "Protective Groups in Organic Synthesis, Theodora W Green (John Wiley & Sons)" and the protecting group may be removed at an appropriate step.

During all the following steps, the order of the steps to be performed may be appropriately changed. In each step, an intermediate may be isolated and then used in the next step.

A. Synthesis of Compound (Ia)

Compound of the following formula (Ia) can be prepared, for example, according to a process shown below.

wherein Rp is an amino protecting group and other symbols are the same as defined above.

Step 1

To a solution of Compound a which can be prepared in a manner described in WO2009/151098 in a solvent such as ether, tetrahydrofuran, hexane or a mixed solvent thereof is added a Grignard reagent such as 2-methyl allyl magnesium chloride which is commercially available or can be prepared by known methods by a person skilled in the art at a temperature between −100° C. and room temperature, preferably at −78° C. and the mixture is reacted for 0.5 hour to 48 hours, preferably 1 hour to 24 hours to afford Compound b.

Step 2

Ozone gas is bubbled into a solution of Compound b in a solvent such as dichloromethane, toluene or a mixed solvent thereof at a temperature between −100° C. and room temperature, preferably at −78° C. until the reaction solution color changes to blue. Then, the reaction solution is subjected to a known reduction reaction such as addition of an amine such as triethylamine, or a sulfide at a temperature between −100° C. and room temperature, preferably at −78° C. for 0.5 hour to 12 hours, preferably 0.5 hour to 5 hours to afford Compound c.

Step 3

To a solution of Compound c in a solvent such as methanol, dioxane, ethyl acetate, or a mixed solvent thereof is reacted under acidic conditions with hydrogen chloride-1,4-dioxane solution or the like at a temperature between 0° C. and 100° C., preferably 10° C. and 50° C. for 0.5 hour to 72 hours, preferably 0.5 hour to 18 hours to afford Compound d.

Step 4

Tert-butoxycarbonyl (Boc group) is illustrated as an example of amino protecting groups in the following examples, but it does not limit to. To a solution of Compound d in a solvent such as tetrahydrofuran, ether, dioxane, ethyl acetate, or a mixed solvent thereof is added a tert-butyl butoxycarbonylating agent such as di-tert-butyldicarbonate at a temperature between 0° C. and 100° C., preferably 10° C. and 50° C. to afford Compound e.

Step 5

According to known methods (Chem. Ber. 1968, 101, 41), to a solution of Compound e in a solvent such as dimethylformamide, tetrahydrofuran, ether, dioxane, ethyl acetate or a mixed solvent thereof, is added a Bredereck reagent such as N,N-dimethylformamide dimethylacetal or tert-butoxy-bis (dimethylamino)-methane, and reacted at a temperature between 0° C. and 150° C., preferably 10° C. and 100° C. for 0.5 hour to 72 hours, preferably 0.5 hour to 18 hours to afford Compound f.

Step 6

To a solution of Compound f in a solvent such as dimethylformamide, tetrahydrofuran, ether, dioxane, ethanol, methanol, or a mixed solvent thereof is added a hydrazine or its hydrochloride, acetate or the like at a temperature between 0° C. and 150° C., preferably 10° C. and reflux temperature for 0.5 hour to 72 hours, preferably 0.5 hour to 10 hours to afford Compound g.

Step 7

To a solution of Compound g in a solvent such as dichloromethane, chloroform, toluene, or a mixed solvent thereof is added an acid such as trifluoroacetic acid is at a temperature between 0° C. and 100° C., preferably 10° C. and reflux temperature for 0.5 hour to 10 hours, preferably 0.5 hour to 3 hours to afford Compound h.

Step 8

To a solution of Compound h in a solvent such as acetonitrile, tetrahydrofuran, ether, dioxane, or a mixed solvent thereof is added an isothiocyanate with a protecting group which is commercially available or prepared by known methods (e.g., isothiocyanate protected with 9-fluorenylmethyloxycarbonyl, Fmoc) and reacted at a temperature between −78° C. and 50° C., preferably −10° C. and 30° C. for 0.5 hour to 10 hour, preferably 0.5 hour to 3 hours. To the mixture are added an alkylating agent such as methyl iodide and an amine such as diisopropylethyl amine and reacted at a temperature between 0° C. and 100° C., preferably 10° C. and reflux temperature for 0.5 hour to 10 hour to afford Compound (Ia). If $R^{2a}$ and $R^{2b}$ of the obtained Compound (Ia) are hydrogen, the target substituent $R^{2a}$ and $R^{2b}$ can be introduced by known methods.

B. Synthesis of Compound (Ib)

Compound of the above formula (Ib) can be prepared, for example, according to a process shown below.

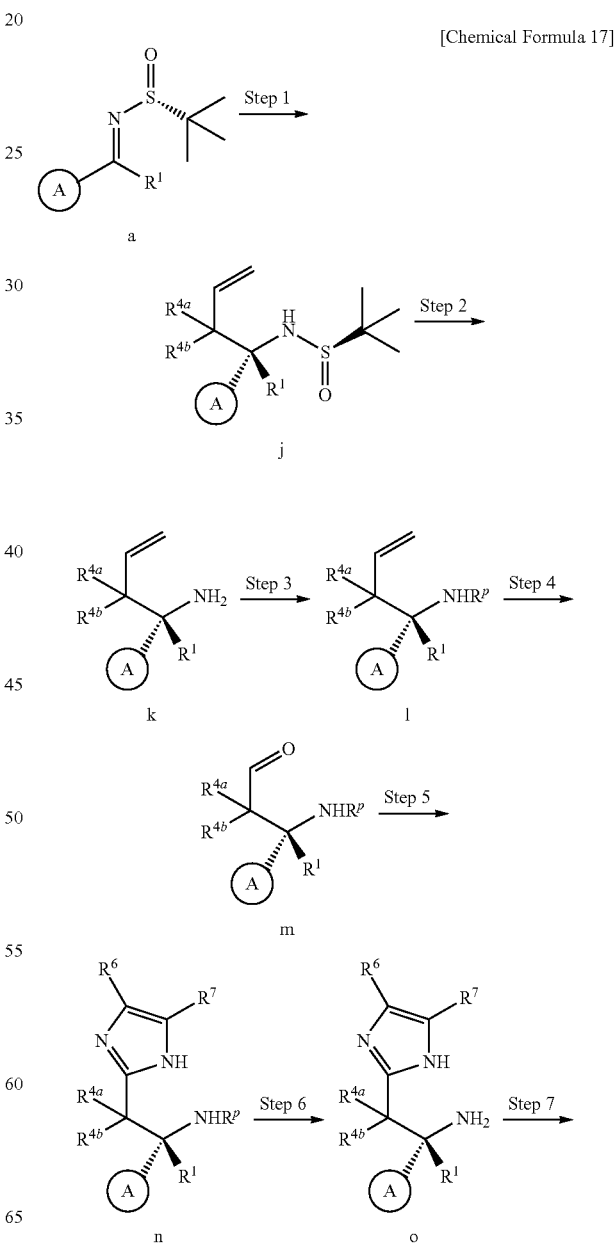

[Chemical Formula 17]

-continued

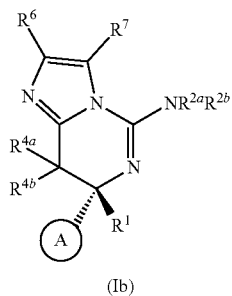

(Ib)

wherein each symbol is the same as defined above.

Step 1

To a solution of Compound a which can be prepared in a manner described in WO2009/151098 in a solvent such as ether, tetrahydrofuran, hexane or a mixed solvent thereof is added a Grignard reagent such as allyl magnesium chloride which is commercially available or prepared by known methods by a person skilled in the art at a temperature between −100° C. and room temperature, preferably at −78° C. for 0.5 hour to 72 hours, preferably 1 hour to 24 hours to afford Compound j.

Step 2

Compound j is reacted in a solvent such as methanol, dioxane, ethyl acetate or a mixed solvent thereof under acidic conditions using 4N hydrogen chloride-1,4-dioxane solution or the like at a temperature between 0° C. and 100° C., preferably 10° C. and 50° C. for 0.5 hour to 72 hours, preferably 0.5 hour to 18 hours to afford Compound Step 3

Tert-butoxycarbonyl (Boc group) is illustrated as an example of amino protecting groups in the following examples, but it does not limit to. To a solution of Compound k in a solvent such as tetrahydrofuran, ether, dioxane, ethyl acetate, or a mixed solvent thereof is added a tert-butoxycarbonylating agent such as di-tert-butyl dicarbonate at a temperature between 0° C. and 100° C., preferably 10° C. and 50° C. to afford Compound l.

Step 4

Ozone gas is bubbled to Compound l in a solvent such as dichloromethane, toluene or a mixed solvent thereof until the color of the reaction solution changes to blue at a temperature between −100° C. and room temperature, preferably at −78° C. Then, the reaction solution is subjected to a known reduction reaction such as addition of an amine, e.g., triethylamine, or a sulfide between −100° C. and room temperature, preferably at −78° C. for 0.5 hour to 12 hours, preferably 0.5 hour to 5 hours to afford Compound m.

Step 5

To a solution of Compound m in a solvent such as methanol, ethanol, dioxane, water or a mixed solvent thereof are added glyoxal and ammonium bicarbonate and reacted at a temperature between 0° C. and 150° C., preferably room temperature and reflux temperature for 0.5 hour to 48 hours, preferably 1 hour to 24 hours to afford Compound n.

Step 6

To a solution of Compound n in a solvent such as dichloromethane, chloroform, toluene, or a mixed solvent thereof is added an acid such as trifluoroacetic acid and reacted at a temperature between 0° C. and 100° C., preferably 10° C. and reflux temperature for 0.5 hour to 10 hours, preferably 0.5 hour to 3 hours to afford Compound o.

Step 7

To a solution of Compound o in a solvent such as acetonitrile, tetrahydrofuran, ether, dioxane, or a mixed solvent thereof is added an isothiocyanate having a protecting group which is commercially available or prepared by known methods (e.g., isothiocyanate protected with benzoyl, Bz) and reacted at a temperature between −78° C. and 50° C., preferably −10° C. and 30° C. for 0.5 hour to 10 hours, preferably 0.5 hour to 3 hours. To the mixture are added an alkylating agent such as methyl iodide and an amine such as diisopropylethyl amine and reacted at a temperature between 0° C. and 100° C., preferably 10° C. and reflux temperature for 0.5 hour to 10 hours to afford Compound (Ib). If $R^{2a}$ and $R^{2b}$ of the obtained Compound (Ib) are hydrogen, the target substituent $R^{2a}$ and $R^{2b}$ can be introduced by known methods.

C. Synthesis of Compounds (Ic) and (Id)

Compound of the above formula (Ic) or (Id) can be prepared, for example, by the process shown below.

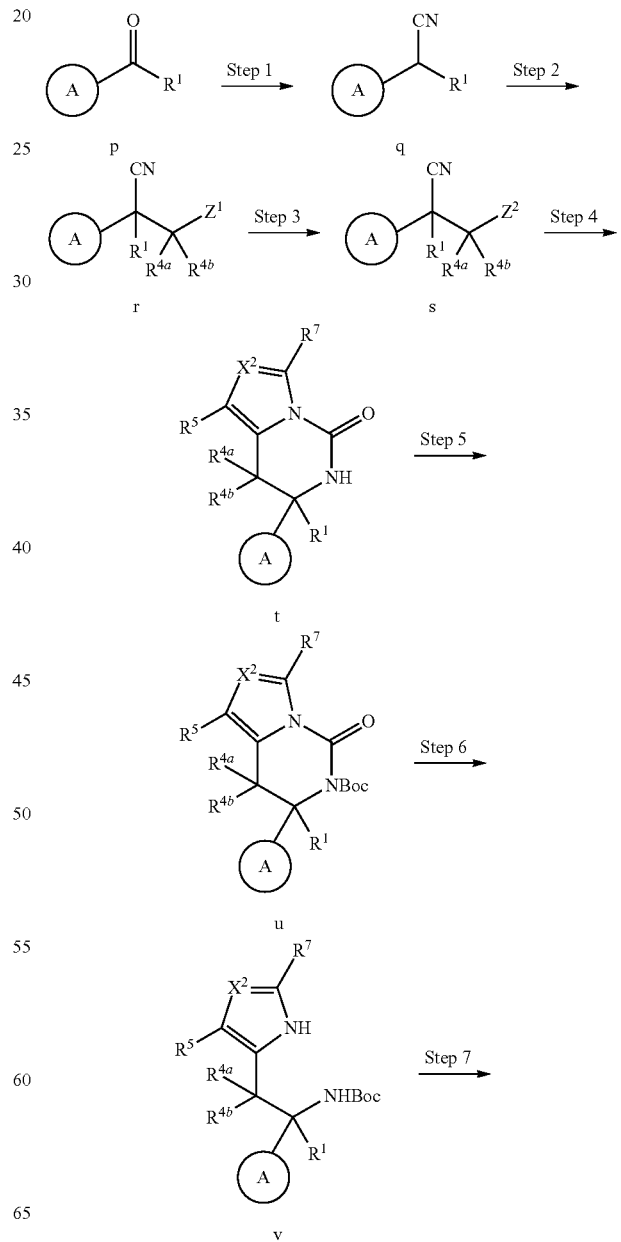

-continued

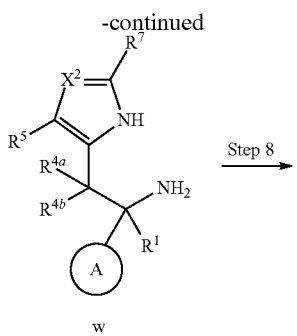

w

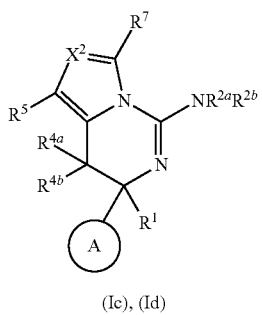

(Ic), (Id)

wherein

[Chemical Formula 19]

$Z^1$ is 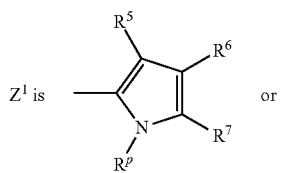 or 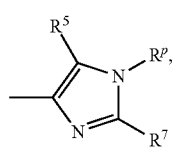  (i), (ii)

$Z^2$ is 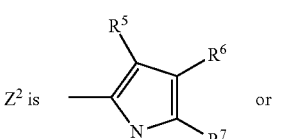 or 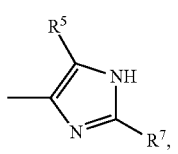  (iii), (iv)

$R^p$ is an amino protecting group, $X^2$ is $CR^6$ or N, and other symbols are the same as defined above.

Step 1

To a solution of Compound p in a solvent such as methanol, ethanol, acetonitrile, tetrahydrofuran, ether, dioxane or a mixed solvent thereof are added p-toluene sulfonylmethyl isocyanide and a base such as potassium carbonate, sodium carbonate or sodium hydride and reacted at a temperature between 0° C. and 150° C., preferably 10° C. and reflux temperature for 0.5 hour to 10 hours, preferably 0.5 hour to 3 hours to afford Compound q.

Step 2

To a solution of Compound q in a solvent such as ether, tetrahydrofuran, hexane, or a mixed solvent thereof are added a base such as lithium diisopropylamide which is commercially available or prepared by known methods and a substrate corresponding to the target compound (e.g., a 4-chloromethyl-1-trithyl imidazole derivative or a 2-chloromethyl-1H-pyrrole derivative) which is commercially available or prepared by known methods and reacted at a temperature between −78° C. and 50° C., preferably 0° C. and room temperature for 0.5 hour to 10 hours, preferably 0.5 hour to 3 hours to afford Compound r.

Step 3

To a solution of Compound r in a solvent such as dichloromethane, chloroform, toluene or a mixed solvent thereof is added an acid such as trifluoroacetic acid and reacted at a temperature between 0° C. and 100° C., preferably 10° C. and reflux temperature for 0.5 hour to 10 hours, preferably 0.5 hour to 5 hours to afford Compound s.

Step 4

Compound s is dissolved in an acid such as concentrated hydrochloric acid and stirred at a temperature between 50° C. and 100° C., preferably at 100° C. for 5 hours to 24 hours, preferably 10 hours to 24 hours and the acid is removed under reduced pressure. To the residue in a solvent such as toluene, acetonitrile, tetrahydrofuran, ether or a mixed solvent thereof are added triethyl amine and diphenylphosphoryl azide and the mixture is stirred at a temperature between 50° C. and 100° C. for 0.5 hour to 10 hours, preferably 0.5 hour to 5 hours to afford Compound t.

Step 5

To a solution of compound t in a solvent such as ether, tetrahydrofuran, dioxane or a mixed solvent thereof are added di-tert-butyl dicarbonate and an amine such as 4,4-dimethylaminopyridine and reacted at a temperature between −78° C. and 50° C., preferably 0° C. and room temperature for 0.5 hour to 10 hours, preferably 0.5 hour to 3 hours to afford Compound u.

Step 6

To a solution of Compound u in a solvent such as methanol, ethanol, water, acetonitrile, tetrahydrofuran, ether, dioxane or a mixed solvent thereof is added a base such as barium hydroxide, lithium hydroxide, or sodium hydroxide and reacted at a temperature between −78° C. and 50° C., preferably 0° C. and room temperature for 0.5 hour to 10 hours, preferably 0.5 hour to 3 hours to afford Compound v.

Step 7

An acid such as trifluoroacetic acid is added to Compound v and reacted at a temperature between 0° C. and 100° C., preferably 10° C. and reflux temperature for 0.5 hour to 10 hours, preferably 0.5 hour to 3 hours to afford Compound w.

Step 8

To a solution of Compound w in a solvent such as acetonitrile, tetrahydrofuran, ether, dioxane, or a mixed solvent thereof is added an isothiocyanate with a protecting group which is commercially available or prepared by known methods (e.g., isothiocyanate protected with 9-fluorenylmethyloxycarbonyl, Fmoc) and reacted at a temperature between −78° C. and 50° C., preferably −10° C. and 30° C. for 0.5 hour to 10 hours, preferably 0.5 hour to 3 hours. After addition of an alkylating agent such as methyl iodide, an amine such as piperidine, or diisopropylethyl amine is added and reacted at a temperature between 0° C. and 100° C., preferably 10° C. and reflux temperature for 0.5 hour to 10 hours to afford Compound (Ic) or (Id). If $R^{2a}$ and $R^{2b}$ of the obtained Compound (Ic) or (Id) are hydrogen, the target substituent $R^{2a}$ and $R^{2b}$ can be introduced by known methods.

Optically active compounds of Compounds (Ia) to (Id) can be prepared from an optically active intermediate obtained in a manner of asymmetry synthesis using an asymmetry reagent at a suitable stage, or by being performed optical resolution of an intermediate or a target compound, each of which is a racemate, at a suitable stage. It is known that there are optical resolution methods such as separation of an optical isomer using an optically active column; kinetic optical resolution utilizing an enzymatic reaction; crystallization resolution of a diastereomer by salt formation using a chiral acid or a chiral base; and preferential crystallization method.

D. Synthesis of Compound (If)

[Chemical Formula 20]

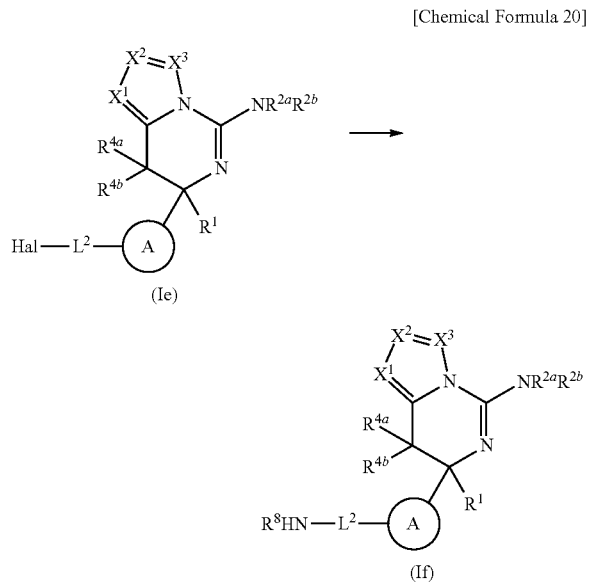

wherein Hal is halogen and other symbols are the same as defined above.

To a solution of Compound (Ie) with halogen on ring A in a solvent such as tetrahydrofuran, toluene or xylene are added trisbenzylidene aceton dipalladium, palladium acetate or palladium (0) which is prepared in the reaction system and a phosphine ligand such as tri-tert-butylphosphine or dicyclohexylbiphenylphosphine. A reagent such as lithium hexamethyl disilazide, or benzophenone imine having a substituent corresponding to a target compound is added at a temperature between −10° C. and 30° C. and the mixture is reacted at a temperature between 30° C. and 120° C., preferably 50° C. and 100° C. for 0.5 hour to 48 hours, preferably 3 hours to 20 hours to afford Compound (If).

E. Synthetic of Compound (Ih)

[Chemical Formula 21]

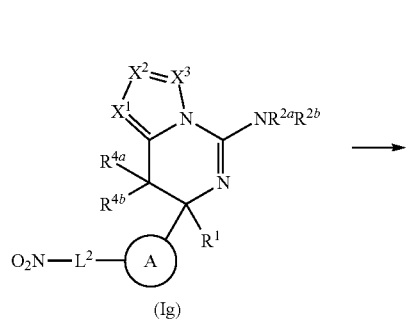

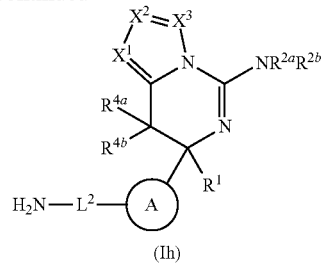

wherein each symbol is the same as defined above.

To a solution of Compound (Ig) in a mixed solvent of acetic acid and water is added an iron and reacted at a temperature between 20° C. and 120° C., preferably 50° C. and 80° C. for 0.5 hour to 48 hours, preferably 6 hours to 20 hours to afford Compound (Ih).

Alternatively, to a solution of Compound 410 in a solvent such as tetrahydrofuran, ethyl acetate or methanol is added a catalytic reduction agent such as 10% palladium/carbon and reacted in the range from atmospheric pressure to 5 atom, preferably atmospheric pressure to 2 atom under hydrogen atmosphere at a temperature between 30° C. and 120° C., preferably 50° C. and 80° C. for 0.5 hour to 48 hours, preferably 6 hours to 20 hours to afford Compound (Ih). Compound (Ih) can be prepared according to methods in Comprehensive Organic Transformations and given in Richard C Larock (Mcgraw-Hill), too.

F. Synthetic of Compound (If)

[Chemical Formula 22]

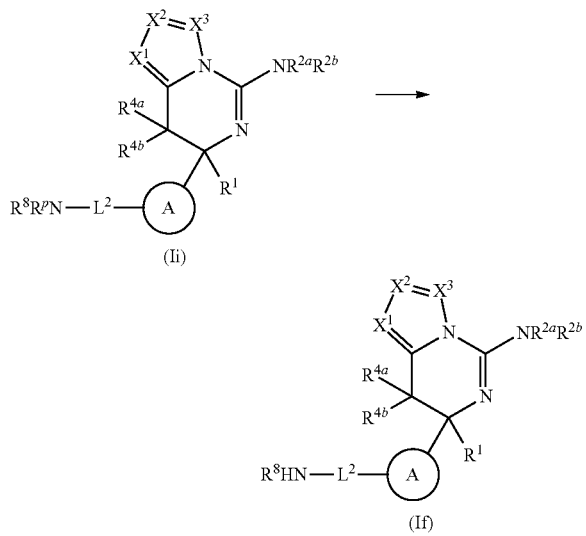

wherein $R^p$ is an amino protecting group and other symbols are the same as defined above.

Compound (If) can be obtained by deprotecting an amino protected Compound (Ii) according to the method in Protective Groups in Organic Synthesis and Theodora W Greene (John Wiley & Sons) or the like.

Any substituent which can be deprotected by the method in Protective Groups in Organic Synthesis, Theodora W Green (John Wiley & Sons) or the like can be employed as an amino protecting group, for example, alkoxycarbonyl, alkenyloxycarbonyl, trialkylsilyl, acyl, methanesulfonyl, trifluoroethanesulfonyl, or toluenesulfonyl.

G. Synthetic of Compound (Ij)

[Chemical Formula 23]

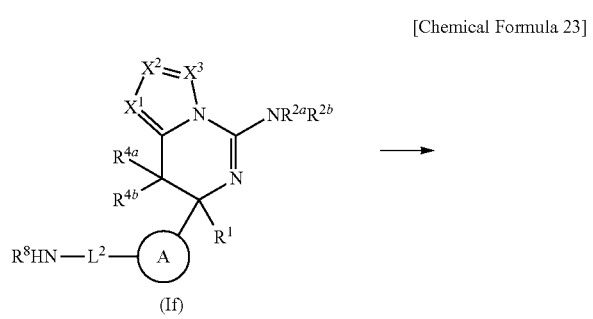

(If)

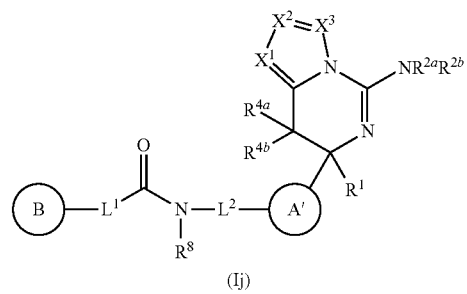

(Ij)

wherein each symbol is the same as defined above.

Compound (Ij) can be prepared by being reacted Compound (If) having a substituted or unsubstituted amino group on ring A with a reactant such as an acid chloride, an acid anhydride, a chlorocarbonic ester or an isocyanate (e.g., benzoyl chloride, 2-furoyl chloride, anhydrous acetic acid, benzyl chloro carbonate, di-tert-butyl dicarbonate, or phenyl isocyanate), each of which has a substituent corresponding to the target compound, in the absence or the presence of a solvent such as tetrahydrofuran or dichloromethane, and in the absence or the presence of a base such as pyridine or triethylamine at a temperature between −80° C. and 100° C., preferably −20° C. and 40° C. for 0.1 hour to 24 hours, preferably 1 hour to 12 hours. Alternatively, Compound (If) in a solvent such as dimethylformamide, tetrahydrofuran, or dichloromethane is reacted with a carboxylic acid such as benzoic acid or 2-pyridine carboxylic acid, each of which has a substituent corresponding to the target compound, in the presence of a dehydration-condensation agent such as dicyclohexylcarbodiimide, carbonyldiimidazole, dicyclohexylcarbodiimide-N-hydroxybenzotriazole at a temperature between −80° C. and 100° C., preferably −20° C. and 40° C. for 0.1 hour to 24 hours, preferably 1 hour to 12 hours to afford Compound (Ij).

H. Synthetic of Compound (Ik)

Compound (Ik) can be prepared by method A or method B.

[Chemical Formula 24]

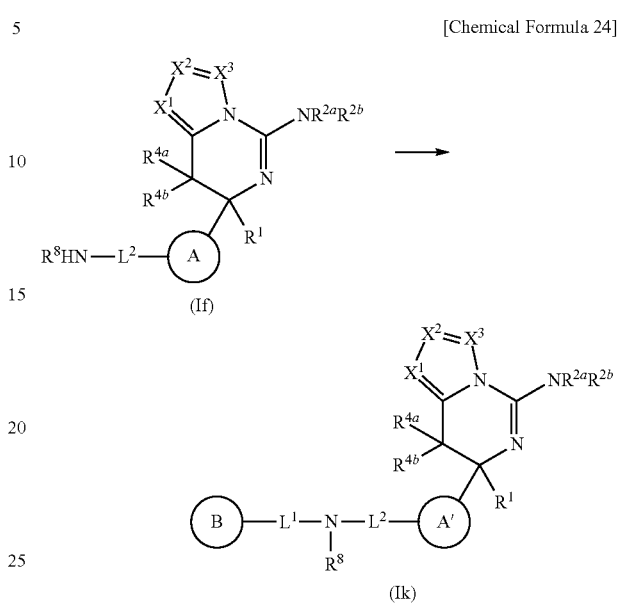

wherein each symbol is the same as defined above.

Method A: Condensation Under Acidic Conditions

An acid such as hydrochloride, sulfuric acid, trifluoroacetic acid, methanesulfonic acid, trifluoromethanesulfonic acid, or perchloric acid is added to an aryl halide or a heteroaryl halide, each of which is commercially available or prepared by the known method (Tetrahedron 2009, vol. 65 757-764) or similar method thereof, and Compound (If) in a solvent such as methanol, ethanol, isopropyl alcohol, butanol, isobutanol, sec-butanol, acetic acid, water or a mixed solvent thereof. The mixture is reacted at a temperature between 0° C. and 180° C., preferably 20° C. and 140° C. for 0.1 hour to 120 hours, preferably 0.5 hour to 72 hours to afford Compound (Ik).

Method B: Condensation Under Basic Conditions

An aryl halide or a heteroaryl halide, each of which is commercially available or prepared by known methods (Tetrahedron, 2009, vol. 65, 757-764) or similar methods thereof is reacted with Compound (If) in a solvent such as toluene, tetrahydrofuran, dimethylformamide, 1,2-dimethoxy ethane, 1,4-dioxane or methanol, in the presence of a base such as triethylamine, sodium carbonate, potassium carbonate, cesium carbonate, sodium methoxide, potassium tert-butoxide, n-butyl lithium, lithium hexamethyldisilazide at a temperature between 0° C. and 180° C., preferably 20° C. and 140° C. for 0.5 hour to 100 hours, preferably 0.5 hour to 72 hours to afford Compound (Ik).

Alternatively, the reaction can be performed after addition of trisdibenzylideneacetone dipalladium, palladium acetate or palladium (0) which is prepared in the reaction system and a phosphine ligand such as triphenylphosphine, tri-tert-butylphosphine, dicyclohexylbiphenylphosphine, 9,9-dimethyl-4,5-bis(diphenylphosphino)xanthene (Xantphos), 2-dicyclohexylphosphino-2',4',6'-tri isopropyl biphenyl (X-Phos), 2-dicyclohexylphosphino-2',6'-diidopropoxy-1,1'-biphenyl (Ruphos). In this case, Compound (Ik) can be prepared by reacting under the microwave irradiation or unirradiated, at a temperature between 0° C. and 150° C., preferably 10° C. and 100° C. for 0.5 hour to 72 hours, preferably 1 hour to 24 hours.

I. Synthetic of Compound (Im)

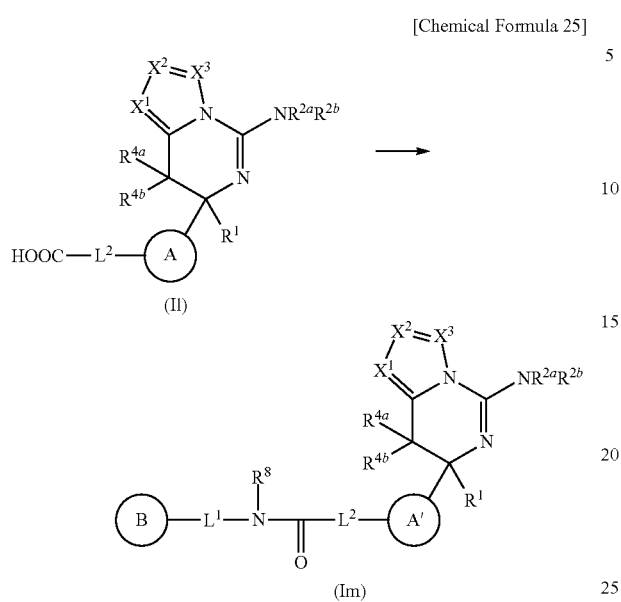

[Chemical Formula 25]

wherein each symbol is the same as defined above.

Compound (II) which has carboxy on ring A in a solvent such as dimethylformamide, tetrahydrofuran or dichloromethane is reacted with a primary amine or a secondary amine such as aniline, 2-aminopyridine or dimethylamine which has a substituent corresponding to the target compound in the presence of a dehydration-condensation agent such as dicyclohexylcarbodiimide, carbonyldiimidazole, or dicyclohexylcarbodiimide-N-hydroxybenzotriazole at a temperature between −80° C. and 100° C., preferably −20° C. and 40° C. for 0.1 hour to 24 hours, preferably 1 hour to 12 hours to afford Compound (Im).

As specific embodiments of the compounds (I) of the present invention, the compounds of the above formulas (Ia) to (Id) wherein each substituent is as follows are exemplified.

Examples of ring A are as follows:

[Chemical Formula 26]

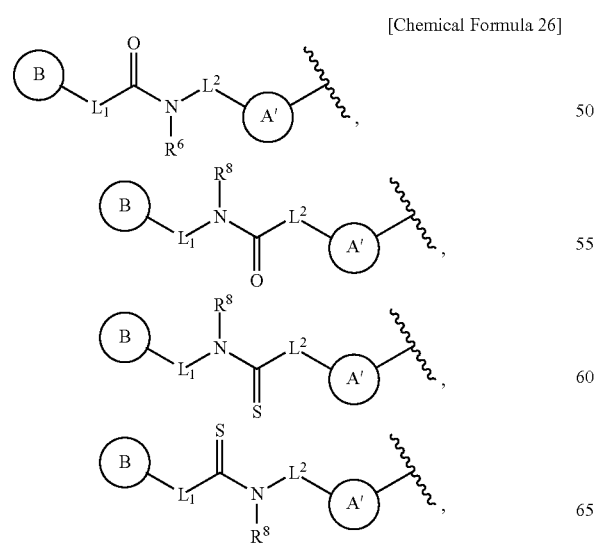

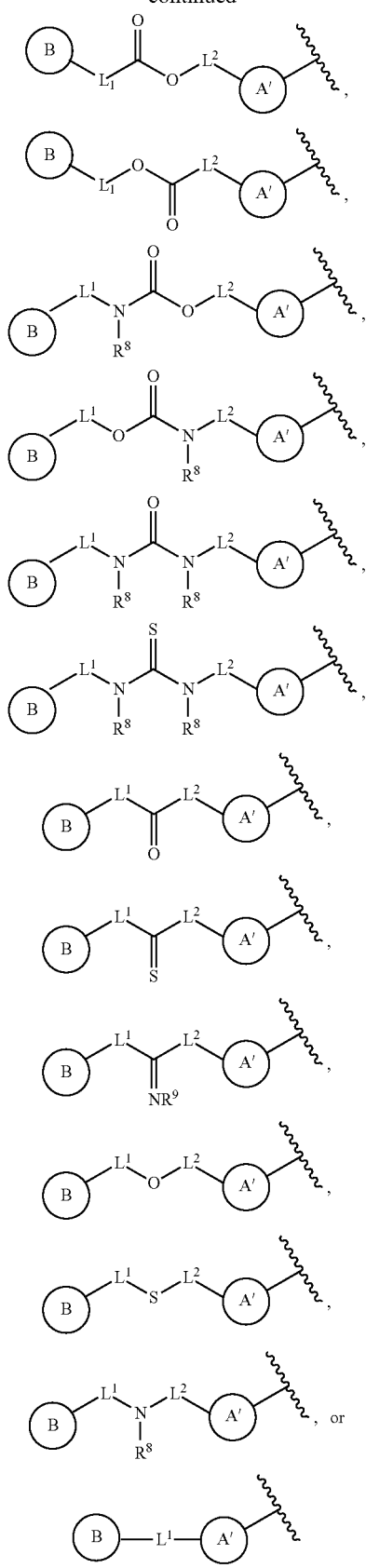

wherein each symbol is the same as defined above.

Ring A is, for example,

[Chemical Formula 27]

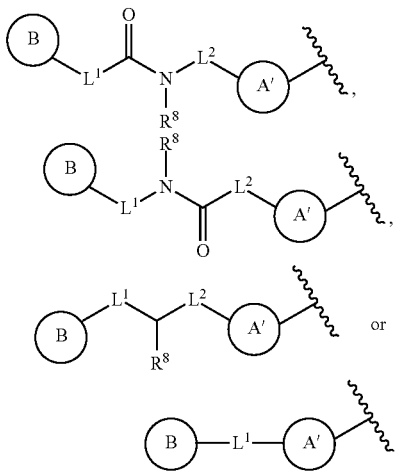

wherein each symbol is the same as defined above.

Ring A is, for example,

[Chemical Formula 28]

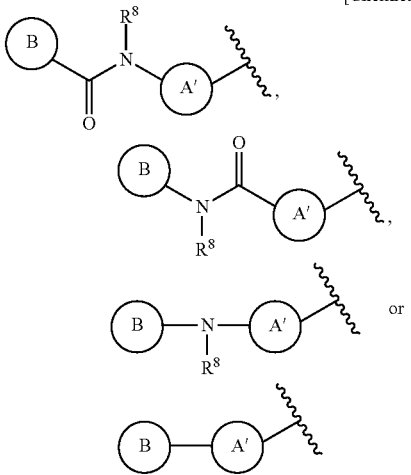

wherein each symbol is the same as defined above.

Ring A' is, for example, a substituted or unsubstituted carbocycle or a substituted or unsubstituted heterocycle.

Ring A' is, for example, substituted or unsubstituted benzene or substituted or unsubstituted pyridine. Examples of the substituents are one or more substituents selected from halogen, cyano, alkyl and alkoxy.

Ring A' is, for example, substituted or unsubstituted benzene. Examples of the substituents are one or more substituents selected from halogen, cyano, alkyl and alkoxy.

Ring B is, for example, a substituted or unsubstituted carbocycle or a substituted or unsubstituted heterocycle.

Ring B is, for example, substituted or unsubstituted pyridine, substituted or unsubstituted pyrimidine or substituted or unsubstituted pyrazine. Examples of the substituents are one or more substituents selected from halogen, cyano, alkyl and alkoxy.

Ring B is, for example, substituted or unsubstituted pyridine. Examples of the substituents are one or more substituents selected from halogen, cyano, alkyl and alkoxy.

$L^1$ and $L^2$ are, for example, each independently a bond, substituted or unsubstituted alkylene, substituted or unsubstituted alkenylene or substituted or unsubstituted alkynylene.

$L^1$ and $L^2$ are, for example, each independently a bond, substituted or unsubstituted alkylene.

$L^1$ and $L^2$ are, for example, both a bond.

$R^5$, $R^6$ and $R^7$ are each independently hydrogen, halogen, hydroxy, substituted or unsubstituted alkyl, substituted or unsubstituted alkenyl, substituted or unsubstituted alkoxy, substituted or unsubstituted alkenyloxy, substituted or unsubstituted alkylthio, substituted or unsubstituted alkenylthio, substituted or unsubstituted acyl, substituted or unsubstituted acyloxy, cyano, carboxy, substituted or unsubstituted alkoxycarbonyl, substituted or unsubstituted alkenyloxycarbonyl, substituted or unsubstituted amino, substituted or unsubstituted carbamoyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, or substituted or unsubstituted heterocyclyloxycarbonyl.

$R^5$, $R^6$ and $R^7$ are, for example, hydrogen, halogen, hydroxy, substituted or unsubstituted alkyl, substituted or unsubstituted alkoxy, substituted or unsubstituted acyl, substituted or unsubstituted acyloxy, cyano, carboxy, substituted or unsubstituted alkoxycarbonyl or substituted or unsubstituted amino.

$R^5$, $R^6$ and $R^7$ are, for example, hydrogen; halogen; hydroxy; alkyl optionally substituted with one or more substituents selected from the substituent group α; alkoxy optionally substituted with one or more substituents selected from the substituent group α; acyl optionally substituted with one or more substituents selected from the substituent group α; acyloxy optionally substituted with one or more substituents selected from the substituent group α; cyano; carboxy; alkoxycarbonyl optionally substituted with one or more substituents selected from the substituent group α; or amino optionally substituted with one or more substituents selected from the substituent group α.

$R^5$, $R^6$ and $R^7$ are, for example, hydrogen.

$R^1$ is, for example, substituted or unsubstituted alkyl, substituted or unsubstituted alkenyl, substituted or unsubstituted alkynyl, cyano, substituted or unsubstituted carbocyclyl or substituted or unsubstituted heterocyclyl.

$R^1$ is, for example, substituted or unsubstituted alkyl.

$R^1$ is, for example, unsubstituted alkyl having a carbon number of 1 to 3.

$R^{2a}$ and $R^{2b}$ are, for example, each independently hydrogen, substituted or unsubstituted alkyl or substituted or unsubstituted acyl.

$R^{2a}$ and $R^{2b}$ are, for example, both hydrogen.

$R^{4a}$ and $R^{4b}$ are, for example, hydrogen, halogen, hydroxy, substituted or unsubstituted alkyl, substituted or unsubstituted alkenyl or substituted or unsubstituted alkynyl.

$R^{4a}$ and $R^{4b}$ are, for example, hydrogen.

Preferable combinations of the substituents of the compound (I) are, for example, the following 1) to 8):

1) The compound wherein ring A is a substituted or unsubstituted carbocycle, $X^1$—$X^2$=$X^3$ is $CR^5$—$CR^6$=$CR^7$ or $CR^5$—N=$CR^7$, $R^1$ is substituted or unsubstituted alkyl, and $R^{2a}$, $R^{2b}$, $R^{4a}$, $R^{4b}$, $R^5$, $R^6$ and $R^7$ are hydrogen, 2) The compound wherein ring A is

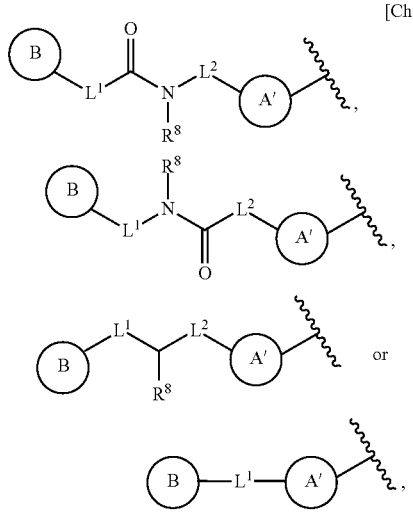

ring A' and ring B are each independently a substituted or unsubstituted carbocycle or a substituted or unsubstituted heterocycle, $L^1$ and $L^2$ are each independently a bond, substituted or unsubstituted alkylene, substituted or unsubstituted alkenylene or substituted or unsubstituted alkynylene, $R^8$ is hydrogen, hydroxy, substituted or unsubstituted alkyl, substituted or unsubstituted alkenyl, substituted or unsubstituted alkynyl or substituted or unsubstituted acyl, $X^1$—$X^2$=$X^3$ is $CR^5$—$CR^6$=$CR^7$ or $CR^5$—N=$CR^7$, $R^1$ is substituted or unsubstituted alkyl, and $R^{2a}, R^{2b}, R^{4a}, R^{4b}, R^5, R^6$ and $R^7$ are hydrogen, 3) The compound wherein ring A is

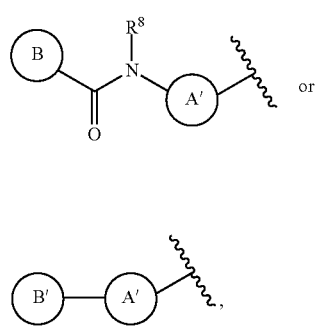

ring A' and ring B are each independently a substituted or unsubstituted carbocycle or a substituted or unsubstituted heterocycle, $R^8$ is hydrogen, hydroxy, substituted or unsubstituted alkyl, substituted or unsubstituted alkenyl, substituted or unsubstituted alkynyl or substituted or unsubstituted acyl, $X^1$—$X^2$=$X^3$ is $CR^5$—$CR^6$=$CR^7$ or $CR^5$—N=$CR^7$, and $R^1$ is substituted or unsubstituted alkyl, and $R^{2a}, R^{2b}, R^{4a}, R^{4b}, R^5, R^6$ and $R^7$ are hydrogen, 4) The compound wherein ring A is

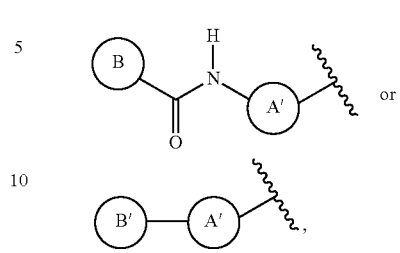

ring A' and ring B are each independently a substituted or unsubstituted carbocycle or a substituted or unsubstituted heterocycle, $X^1$—$X^2$=$X^3$ is $CR^5$—$CR^6$=$CR^7$ or $CR^5$—N=$CR^7$, $R^1$ is substituted or unsubstituted alkyl, and $R^{2a}, R^{2b}, R^{4a}, R^{4b}, R^5, R^6$ and $R^7$ are hydrogen, 5) The compound wherein ring A is

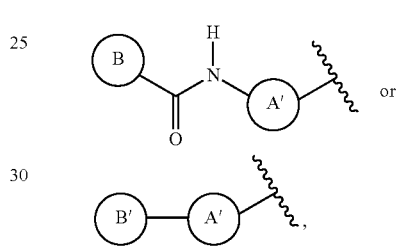

ring A' and ring B are each independently substituted or unsubstituted benzene or substituted or unsubstituted pyridine, $X^1$—$X^2$=$X^3$ is $CR^5$—$CR^6$=$CR^7$ or $CR^5$—N=$CR^7$, $R^1$ is substituted or unsubstituted alkyl, and $R^{2a}, R^{2b}, R^{4a}, R^{4b}, R^5, R^6$ and $R^7$ are hydrogen, 6) The compound wherein ring A is

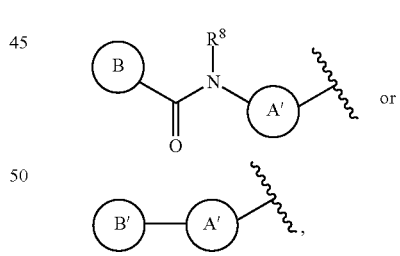

ring A' and ring B are each independently a substituted or unsubstituted carbocycle or a substituted or unsubstituted heterocycle, ring B' is substituted or unsubstituted pyridine, substituted or unsubstituted pyrimidine or substituted or unsubstituted pyrazine, $R^8$ is each independently hydrogen, hydroxy, substituted or unsubstituted alkyl, substituted or unsubstituted alkenyl, substituted or unsubstituted alkynyl or substituted or unsubstituted acyl, $X^1$—$X^2$=$X^3$ is N—$CR^6$=$CR^7$ or $CR^5$—$CR^6$=N, $R^1$ is substituted or unsubstituted alkyl, or $R^{2a}, R^{2b}, R^{4a}, R^{4b}, R^5, R^6$ and $R^7$ are hydrogen, 7) The compound wherein ring A is

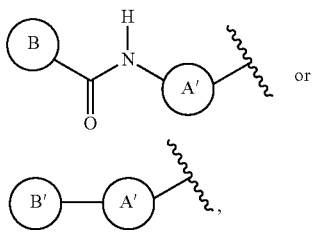

[Chemical Formula 34]

or ring A' and ring B are each independently a substituted or unsubstituted carbocycle or a substituted or unsubstituted heterocycle,
ring B' is substituted or unsubstituted pyridine, substituted or unsubstituted pyrimidine or substituted or unsubstituted pyrazine,
$X^1$—$X^2$=$X^3$ is N—$CR^6$=$CR^7$ or $CR^5$—$CR^6$=N,
$R^1$ is substituted or unsubstituted alkyl, and
$R^{2a}$, $R^{2b}$, $R^{4a}$, $R^{4b}$, $R^5$, $R^6$ and $R^7$ are hydrogen, and
8) The compound wherein ring A is

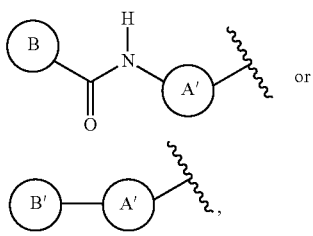

[Chemical Formula 35]

or ring A' and ring B are each independently substituted or unsubstituted benzene, substituted or unsubstituted pyridine or substituted or unsubstituted thiophen,
ring B' is substituted or unsubstituted pyridine,
$X^1$—$X^2$=$X^3$ is N—$CR^6$=$CR^7$ or $CR^5$—$CR^6$=N,
$R^1$ is substituted or unsubstituted alkyl, and
$R^{2a}$, $R^{2b}$, $R^{4a}$, $R^{4b}$, $R^5$, $R^6$ and $R^7$ are hydrogen.

The compounds of the present invention have BACE1 inhibitory activity, and therefore, are useful as a medicament for treatment, prevention, and/or symptom improvement of the diseases induced by the production, secretion or deposition of amyloid β protein such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia such as coexist Alzheimer's disease with vascular type dementia, dementia with Parkinson's Disease, dementia with progressive supranuclear palsy, dementia with Cortico-basal degeneration, Alzheimer's disease with diffuse Lewy body disease, age-related macular degeneration, Parkinson's Disease and amyloid angiopathy.

The compound of the present invention has not only BACE1 inhibitory activity but the beneficialness as a medicament. The compound has any or all of the following superior properties.
a) Inhibitory activity for CYP enzymes such as CYP1A2, CYP2C9, CYP2C19, CYP2D6 or CYP3A4 of the compound is weak.
b) The compound show excellent pharmacokinetics such as high bioavailability or moderate clearance.
c) The compound has high metabolic stability.
d) The compound does not show irreversible inhibition to CYP enzyme such as CYP3A4 in the range of the concentration of the measurement conditions described in this description.
e) The compound does not show mutagenesis.
f) Risk of cardiovascular systems of the compound is low.
g) The compound show high solubility.
h) The compound show high brain distribution.
i) The compound has high oral absorption.
j) The compound has long half-life period.
k) The compound has high protein unbinding ratio.
l) The compound show negative in the Ames test.

Since the compound of the present invention has high inhibitory activity on BACE1 and/or high selectivity on other enzymes, it can be a medicament with reduced side effect. Further, since the compound has high effect of reducing amyloid β production in a cell system, particularly, has high effect of reducing amyloid β production in brain, it can be an excellent medicament. In addition, by converting the compound into an optically active compound having suitable stereochemistry, the compound can be a medicament having a wider safety margin on the side effect.

When a pharmaceutical composition of the present invention is administered, it can be administered orally or parenterally. The composition for oral administration can be administered in usual dosage forms such as tablets, granules, powders, capsules which can be prepared according to the conventional manners. The composition for parenteral administration can be administered suitably in usual parenteral dosage forms such as injections. Since the compounds of the present invention have high oral absorption, they can be preferably administered in an oral dosage form.

A pharmaceutical composition can be formulated by mixing various additive agents for medicaments, if needed, such as excipients, binders, disintegrating agents, and lubricants which are suitable for the formulations with an effective amount of the compound of the present invention.

Although the dosage of a pharmaceutical composition of the present invention should be determined in consideration of the patient's age and body weight, the type and degree of diseases, the administration route and the like, an usual oral dosage for an adult is 0.05 to 100 mg/kg/day and preferable is 0.1 to 10 mg/kg/day. For parenteral administration, although the dosage highly varies with administration routes, an usual dosage is 0.005 to 10 mg/kg/day and preferably 0.01 to 1 mg/kg/day. The dosage may be administered in one to several divisions per day.

The compound of the present invention can be used combining other medicaments for treating Alzheimer's disease such as an acetylcholinesterase inhibitor (hereinafter referred to as a concomitant medicament) for the purpose of enforcement of the activity of the compound or reduction of the amount of medication of the compound or the like. Under the present circumstances, timing of administration of the compound of the present invention and the concomitant medicament is not limited and these may be administered to the subject simultaneously or in a time proximity to each other. Furthermore, the compound of the present invention and concomitant medicament may be administered as two different compositions containing each active ingredient or as a single composition containing both active ingredient.

The dose of the concomitant medicament can be suitably selected on the basis of the dose used on clinical. Moreover, the mix ratio of the compound of the present invention and a concomitant medicament can be suitably selected in consideration of the subject of administration, administration route, target diseases, symptoms, combinations, etc. For example, when the subject of administration is human, the concomitant medicament can be used in the range of 0.01-100 parts by weight relative to 1 part by weight of the compound of the present invention.

Examples of a concomitant medicament are Donepezil hydrochloride, Tacrine, Galanthamine, Rivastigmine, Zanapezil, Memantine and Vinpocetine.

EXAMPLE

The present invention will be described in more detail with reference to, but not limited to, the following examples and test examples.

In this description, meanings of each abbreviation are as follows:

Me methyl
Et ethyl
Bz benzoyl
Boc t-butoxycarbonyl
THF tetrahydrofuran
DMF N,N-dimethylformamide
EDC 1-ethyl-3-(3-dimethylaminopropyl)carbodiimide NMR analysis of each Example was performed by 300 MHz using DMSO-$d_6$ and CDCl$_3$.

$^1$H-NMR was measured using tetramethylsilane as an internal standard in deuterochloroform (CDCl$_3$) solvent. The δ values were shown by ppm and the coupling constant (J) were shown by Hz. In the data, s means singlet, d means doublet, t means triplet, m means multiplet, br means broad and brs means broad singlet.

"RT" in tables means retention time in LC/MS: liquid column chromatography/mass analysis, and these were measured under the conditions as mentioned below. (Compound I-4 was measured under Conditions B and others were measured under Conditions A)

Conditions A
Column: Shim-pack XR-ODS (2.2 μm, i.d.50×3.0 mm) (Shimadzu)
Flow rate: 1.6 mL/min
Columns oven: 50° C.
UV detection wavelength: 254 nm
Mobile phases: [A] is 0.1% formic acid solution, and [B] is 0.1% formic acid in acetonitrile solvent.
Gradient: linear gradient of 10% to 100% solvent[B] for 3 minutes was performed, and 100% solvent[B] was maintained for 1 minute.

Conditions B
Column: XBridge C18 (5 μm, i.d. 4.6×50 mm) (Waters)
Flow rate: 3 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 1 minute.

Example 1

Synthesis of Compound (I-2)

[Chemical Formula 36]

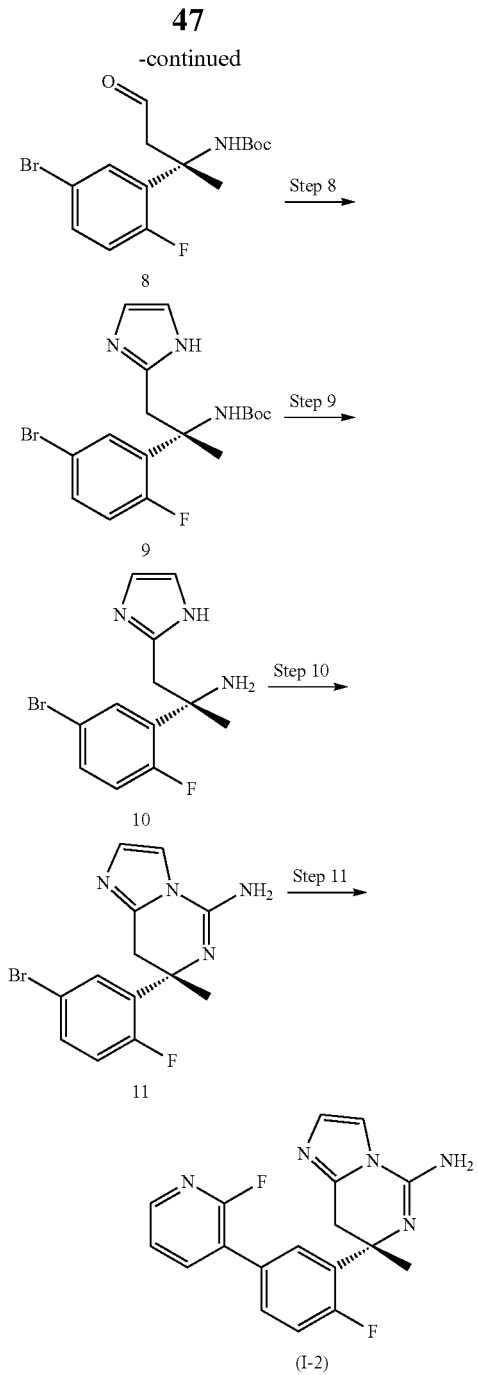

¹H-NMR (CDCl₃) δ: 1.50 (d, J=6.4 Hz, 3H), 1.91 (d, J=4.2 Hz, 1H), 5.16 (dq, J=4.2, 6.4 Hz, 1H), 6.91 (dd, J=9.9, 8.7 Hz, 1H), 7.31-7.38 (m, 1H), 7.64 (dd, J=6.5, 2.5 Hz, 1H).

Step 2

To a solution of Compound 2 (14.01 g) in ethyl acetate (150 ml) was added 2-iodoxybenzoic acid (35.8 g), and the mixture was refluxed for 7 hours. The reaction solution was cooled in an ice bath and the precipitated solid was removed by filtration. The filtrate was evaporated under reduced pressure to afford Compound 3 (13.66 g)

¹H-NMR (CDCl₃) δ: 2.64 (d, J=5.0 Hz, 3H), 7.05 (dd, J=10.2, 8.7 Hz, 1H), 7.58-7.64 (m, 1H), 7.98 (dd, J=6.4, 2.5 Hz, 1H).

Step 3

To a solution of Compound 3 (13.40 g) in THF (300 ml) were added (R)-2-methyl-2-propane sulfinamide (9.73 g) and titanium (IV) ethoxide (42.3 g) under nitrogen atmosphere and the mixture was refluxed for 4.5 hours. To the reaction solution were added water and ethyl acetate and the precipitated solid was removed by filtration. The filtrate was extracted with ethyl acetate. The organic layer was washed with water and brine and dried over anhydrous sodium sulfate. The solvent was evaporated under reduced pressure and the obtained residue was purified by column chromatography to afford Compound 4 (16.80 g).

¹H-NMR (CDCl₃) δ: 1.32 (s, 9H), 2.75 (d, J=3.4 Hz, 3H), 7.01 (dd, J=10.6, 8.9 Hz, 1H), 7.50-7.57 (m, 1H), 7.75-7.80 (m, 1H).

Step 4

Allylmagnesium bromide (1M diethyl ether solution, 100 ml) was poured into a 4-neck flask under nitrogen atmosphere and cooled in a dry ice-acetone bath. A solution of Compound 4 (10.65 g) in diethyl ether (50 ml) was added and the mixture was stirred at −78° C. for 1 hour and at 0° C. for 1 hour. After completion of addition, the mixture was stirred at a temperature between −10° C. and −5° C. for 1 hour. To the reaction solution were added an aqueous saturated ammonium chloride solution and water. The aqueous layer was extracted with ethyl acetate and the organic layer was sequentially washed with water and brine. The organic layer was dried over anhydrous magnesium sulfate and the solvate was evaporated under reduced pressure. The obtained residue was purified by column chromatography to afford Compound 5 (9.04 g).

¹H-NMR (CDCl₃) δ: 1.22 (s, 9H), 1.69 (s, 3H), 2.65 (dd, J=13.8, 7.5 Hz, 1H), 2.75 (dd, J=13.8, 6.8 Hz, 1H), 4.01 (s, 1H), 5.06 (s, 1H), 5.11 (d, J=3.7 Hz, 1H), 5.43-5.58 (m, 1H), 6.92 (dd, J=12.1, 8.6 Hz, 1H), 7.34-7.40 (m, 1H), 7.56 (dd, J=7.2, 2.5 Hz, 1H).

Step 5

To a solution of Compound 5 (8.99 g) in methanol (50 ml) was added a 4 mol/L hydrogen chloride-1,4-dioxane (8.68 ml) solution and the mixture was stirred at room temperature for 1 hour. The solvent was evaporated under reduced pressure. To the obtained residue was added water and extracted with diethyl ether. The organic layer was washed with water. The combined aqueous layer was made alkaline using a saturated sodium bicarbonate solution and extracted with ethyl acetate. The organic layer was washed with water and brine, and dried over anhydrous magnesium sulfate. The solvent was evaporated under reduced pressure to afford Compound 6 (6.56 g).

¹H-NMR (CDCl₃) δ: 1.50 (s, 3H), 1.61 (s, 2H), 2.46 (dd, J=13.7, 8.1 Hz, 1H), 2.73 (dd, J=13.7, 6.6 Hz, 1H), 5.03-5.10 (m, 2H), 5.23-5.59 (m, 1H), 6.91 (dd, J=11.7, 8.6 Hz, 1H), 7.30-7.35 (m, 1H), 7.61 (dd, J=7.6, 2.5 Hz, 1H).

Step 1

5-Bromo-2-fluorobenzaldehyde (1) (12.98 g) was dissolved in tetrahydrofuran (60 ml) under nitrogen atmosphere, and the solution was cooled in a dry ice-acetone bath. To the solution was added dropwise methylmagnesium chloride (3M in THF, 25.6 ml) at a temperature between −78° C. and −30° C. After completion of addition, the mixture was stirred at a temperature between −10° C. and −5° C. for 1 hour. To the reaction solution were added an aqueous saturated ammonium chloride solution and water, extracted with ethyl acetate and washed subsequently with water and brine. The organic layer was dried over anhydrous magnesium sulfate and the solvent was evaporated under reduced pressure to afford Compound 2 (14.51 g).

Step 6

To a solution of Compound 6 (3.00 g) in THF (30 ml) was added di-tert-butyl dicarbonate (3.80 g), and the mixture was stirred at 60° C. for 8 hours. The solvent was evaporated under reduced pressure. To the residue were added water and an aqueous saturated sodium bicarbonate solution and extracted with ethyl acetate. The organic layer was dried over anhydrous magnesium sulfate and the solvent was evaporated under reduced pressure. The residue was purified by column chromatography to afford crude Compound 7 (4.58 g).

$^1$H-NMR (CDCl$_3$) δ: 1.38 (brs, 9H), 1.72 (s, 3H), 2.55 (dd, J=13.9, 7.9 Hz, 1H), 2.78-2.87 (m, 1H), 4.94 (br, 1H), 5.13 (d, J=2.0 Hz, 1H), 5.18 (s, 1H), 5.52-5.65 (m, 1H), 6.90 (dd, J=11.9, 8.6 Hz, 1H), 7.29-7.35 (m, 1H), 7.38 (dd, J=7.2, 2.2 Hz, 1H).

Step 7

A solution of Compound 7 (4.16 g) in dichloromethane (60 ml) was cooled in a dry ice-acetone bath and ozone gas was bubbled at −78° C. Bubbling was stopped when the color of the reaction solution changed to blue and nitrogen gas was introduced. To the reaction solution was added triethylamine (4.83 ml). The mixture was warmed to room temperature from −78° C. and stirred for 1 hour. Water was added and the solution was extracted with dichloromethane. The organic layer was washed with brine and dried over anhydrous magnesium sulfate. The solvent was evaporated under reduced pressure and the obtained residue was purified by column chromatography to afford Compound 8 (3.57 g).

$^1$H-NMR (CDCl$_3$) δ: 1.41 (s, 9H), 1.72 (s, 3H), 2.99 (dd, J=16.3, 1.8 Hz, 1H), 3.50 (d, J=16.3 Hz, 1H), 5.17 (s, 1H), 6.94 (dd, J=11.9, 8.6 Hz, 1H), 7.33-7.45 (m, 2H), 9.72 (s, 1H).

Step 8

To a suspension of ammonium hydrogen carbonate (1.85 g) in water (5 ml) was added a 39% aqueous solution of glyoxal (1.38 ml) and subsequently added a solution of Compound 8 (1.76 g) in methanol (20 ml). The mixture was stirred at room temperature for 24 hours and the solvent was evaporated under reduced pressure. To the residue were added water and an aqueous saturated sodium bicarbonate solution and extracted with chloroform. The organic layer was dried over anhydrous magnesium sulfate and the solvent was evaporated under reduced pressure. The obtained residue was purified by column chromatography to afford Compound 9 (1.13 g).

$^1$H-NMR (CDCl$_3$) δ: 1.43 (s, 9H), 1.75 (s, 3H), 3.34 (d, J=14.4 Hz, 1H), 3.62 (d, J=14.4 Hz, 1H), 5.75 (br, 1H), 6.88-6.96 (m, 2H), 7.03 (br, 1H), 7.30-7.36 (m, 2H), 9.19 (br, 1H).

Step 9

To a solution of Compound 9 (1.13 g) in methanol (10 mL) was added a 4 mol/L hydrogen chloride-1,4-dioxane solution (7.09 ml) and the mixture was stirred at room temperature for 16 hours. After the solvent was evaporated under reduced pressure, the obtained residue was made alkaline using an aqueous saturated sodium bicarbonate solution and the mixture was extracted with chloroform. The organic layer was dried over anhydrous magnesium sulfate and the solvent was evaporated under reduced pressure. The obtained residue was purified by column chromatography to afford Compound 10 (0.82 g).

$^1$H-NMR (CDCl$_3$) δ: 1.49 (s, 3H), 3.16 (d, J=15.2 Hz, 1H) 3.35 (d, J=15.2 Hz, 1H), 3.70 (s, 3H), 6.91 (s, 2H), 6.92 (dd, J=11.9, 8.6 Hz, 1H), 7.30-7.36 (m, 1H), 7.57 (dd, J=7.4, 2.5 Hz, 1H).

Step 10

A solution of Compound 10 (185 mg) in acetonitrile (1 ml) was cooled in an ice bath. To the solution was added a solution of 9-fluorene methoxycarbonyl isothiocyanate (175 mg) in acetonitrile (2 ml), and the mixture was stirred at room temperature for 0.5 hours. To the reaction solution were added methyl iodide (176 mg) and N,N-diisopropylethylamine (401 mg) and the mixture was stirred at 80° C. for 1 hour. After the solution was cooled to room temperature, piperidine (63.3 mg) was added and the mixture was stirred at room temperature for 1 hour. After the solvent was evaporated under reduced pressure, water was added to the residue and extracted with chloroform. The organic layer was dried over anhydrous magnesium sulfate and the solvent was evaporated under reduced pressure. The obtained residue was purified by column chromatography to afford Compound 11 (183 mg).

$^1$H-NMR (CDCl$_3$) δ: 1.53 (brs, 3H), 3.20-3.50 (m, 2H), 6.92 (dd, J=11.7, 8.6 Hz, 1H), 6.99 (s, 1H), 7.31-7.36 (m, 1H), 7.31-7.36 (m, 1H), 7.85 (br, 1H).

Step 11

To a solution of Compound 11 (118 mg) in DMF (4 ml) were added 2-fluoropyridin-3-yl boronic acid (77 mg) and a 2M aqueous sodium carbonate solution (0.55 ml) under nitrogen atmosphere after degassing. After [1,1'-bis(diphenylphosphino)ferrocene]dichloropalladium-dichloromethane complex (1:1) (29.8 mg) was added, cyano picolinic acid hydrate (34.8 mg) and EDC hydrochloride (40.2 mg) were added. DMF (1 ml) was poured into the solution and the system was purged with nitrogen. After the mixture was stirred at 100° C. for 2 hours, water was added to the reaction solution and extracted with ethyl acetate. The organic layer was washed subsequently with water and brine and dried over anhydrous magnesium sulfate. The solvent was evaporated under reduced pressure and the obtained residue was purified by column chromatography to afford Compound (I-2) (85.9 mg).

Example 2

Synthetic of Compound (I-1)

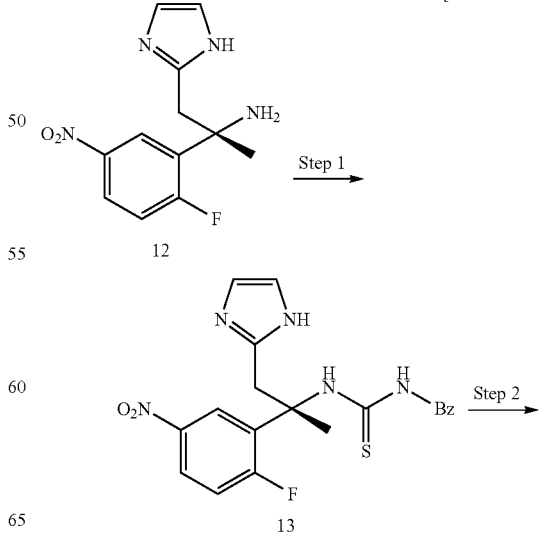

[Chemical Formula 37]

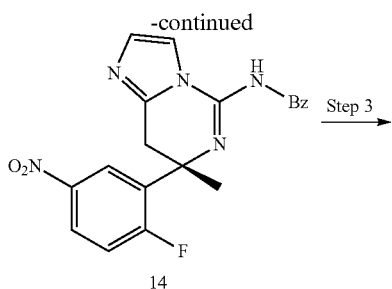

14

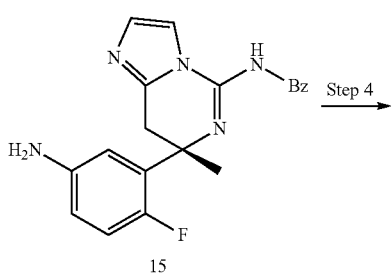

15

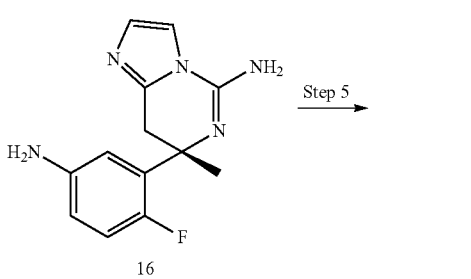

16

(I-1)

Step 1

Compound 12 can be synthesized in a similar manner to Step 3 to Step 9 in Example 1 using commercially available 2-fluoro-5-nitroacetophenone as a starting material. To a solution of Compound 12 (500 mg) in acetone (10 ml) was added benzoyl isothiocyanate (340 mg), and the mixture was stirred at room temperature for 1 hour. The solvent was evaporated under reduced pressure, then water was added to the residue and extracted with ethyl acetate. The organic layer was washed sequentially with water and brine and dried over anhydrous magnesium sulfate. The solvent was evaporated under reduced pressure and the obtained residue was purified by column chromatography to afford Compound 13 (292 mg).

$^1$H-NMR (CDCl$_3$) δ 2.03 (s, 3H), 3.51 (d, J=14.1 Hz, 1H), 4.54 (d, J=14.1 Hz, 1H), 7.00 (brs, 1H), 7.21 (dd, J=11.0, 8.9 Hz, 1H), 7.53 (t, J=7.3 Hz, 2H), 7.65 (t, J=7.3 Hz, 1H), 7.83 (d, J=7.3 Hz, 2H), 8.17-8.24 (m, 1H), 8.32 (dd, J=6.7, 2.7 Hz, 1H), 8.82 (s, 1H), 9.47 (br, 1H), 11.32 (s, 1H).

Step 2

To a solution of Compound 13 (292 mg) in acetonitrile (10 ml) were added methyl iodide (194 mg) and N,N-diisopropylethylamine (441 mg), and the mixture was refluxed for 2 hours. The solvent was evaporated under reduced pressure, then water was added to the residue and extracted with ethyl acetate. The organic layer was washed sequentially with water and brine and dried over anhydrous magnesium sulfate. The solvent was evaporated under reduced pressure and the obtained residue was purified by column chromatography to afford Compound 14 (101 mg).

$^1$H-NMR (CDCl$_3$) δ: 1.95 (s, 3H), 3.40 (d, J=16.6 Hz, 1H) 3.96 (d, J=16.6 Hz, 1H), 7.00 (d, J=1.7 Hz, 1H) 7.22-7.31 (m, 1H), 7.45-7.52 (m, 2H), 7.54-7.60 (m, 1H), 7.74 (d, J=1.7 Hz, 1H), 8.18-8.25 (m, 2H), 8.29-8.34 (m, 2H), 11.46 (brs, 1H).

Step 3

To a solution of Compound 14 (74.2 mg) in THF (3 ml) was added 10% palladium-carbon (20 mg, containing 50% water), the system was replaced with hydrogen gas. The mixture was stirred at room temperature for 24 hours and filtered through Celite. The filtrate was concentrated under reduced pressure and the obtained residue was purified by column chromatography to afford Compound 15 (64.1 mg).

$^1$H-NMR (CDCl$_3$) δ: 1.86 (s, 3H), 3.28 (d, J=16.5 Hz, 1H) 3.55 (brs, 1H), 3.90 (d, J=16.5 Hz, 1H) 6.44-6.54 (m, 2H), 6.86 (dd, J=11.9, 8.6 Hz, 1H), 6.98 (d, J=1.7 Hz, 1H), 7.43-7.60 (m, 3H), 7.72 (d, J=1.7 Hz, 1H), 8.29-8.34 (m, 2H), 11.31 (brs, 1H).

Step 4

Concentrated sulfuric acid (15.4 mg) was added to Compound 15 (57 mg) and the mixture was stirred at 80° C. for 16 hours. The reaction solution was cooled in an ice bath and an aqueous saturated sodium bicarbonate solution and water were added. The mixture was extracted with chloroform and the solvent was evaporated under reduced pressure. The obtained residue was purified by column chromatography to afford Compound 16 (42 mg).

$^1$H-NMR (CDCl$_3$) δ: 1.64 (s, 3H), 3.22 (d, J=16.3 Hz, 1H), 3.57 (d, J=16.3 Hz, 1H), 4.08 (br, 4H) 6.45-6.51 (m, 1H), 6.71 (dd, J=6.7, 2.7 Hz, 1H), 6.82 (dd, J=12.1, 8.7 Hz, 1H), 6.94 (d, J=1.7 Hz, 1H), 7.25 (d, J=1.7 Hz, 1H).

Step 5

To a solution of Compound 16 (21.2 mg) in methanol (0.5 ml) was added 2 mol/L hydrochloric acid (0.05 ml), and the mixture was stirred at room temperature for 10 minutes. To the mixture were added 5-cyanopicolinic acid hydrate (16.3 mg), EDC hydrochloride (18.8 mg) and methanol (0.5 ml), and the mixture was stirred at room temperature for 15 hours. The solvent was evaporated under reduced pressure. To the residue were added an aqueous saturated sodium bicarbonate solution and water and extracted with ethyl acetate. The organic layer was washed sequentially with water and brine, and dried over anhydrous magnesium sulfate. The solvent was evaporated under reduces pressure and the obtained residue was purified by column chromatography to afford Compound (I-1) (17.3 mg).

Example 3

Synthesis of Compound (I-3)

[Chemical Formula 38]

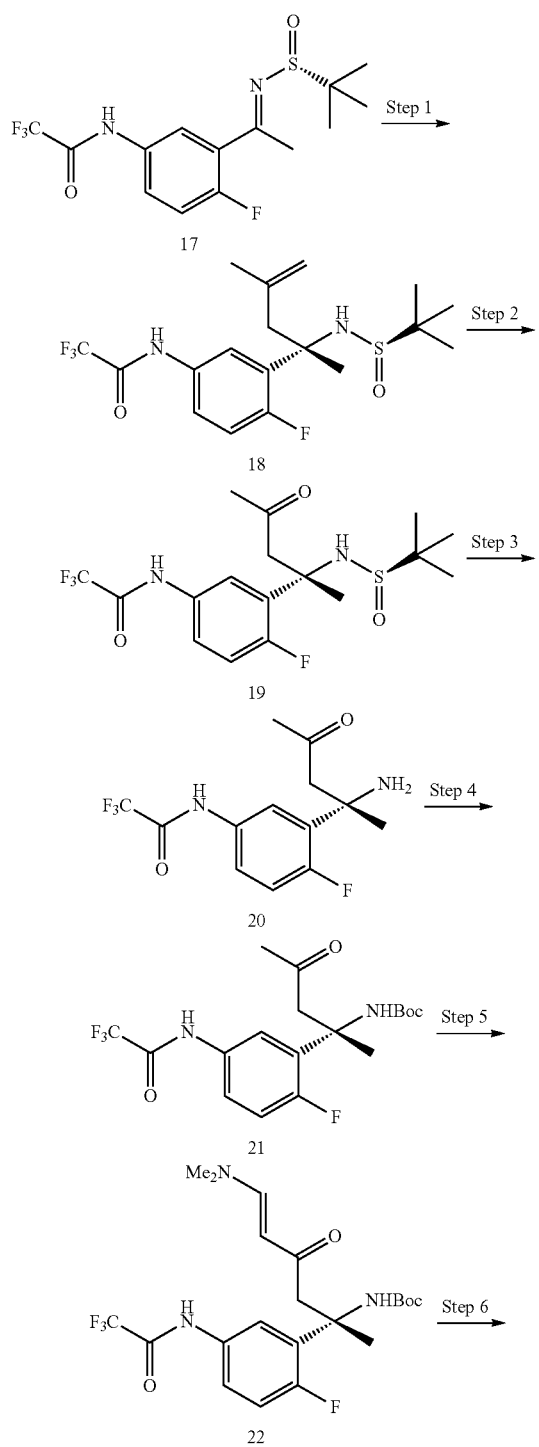

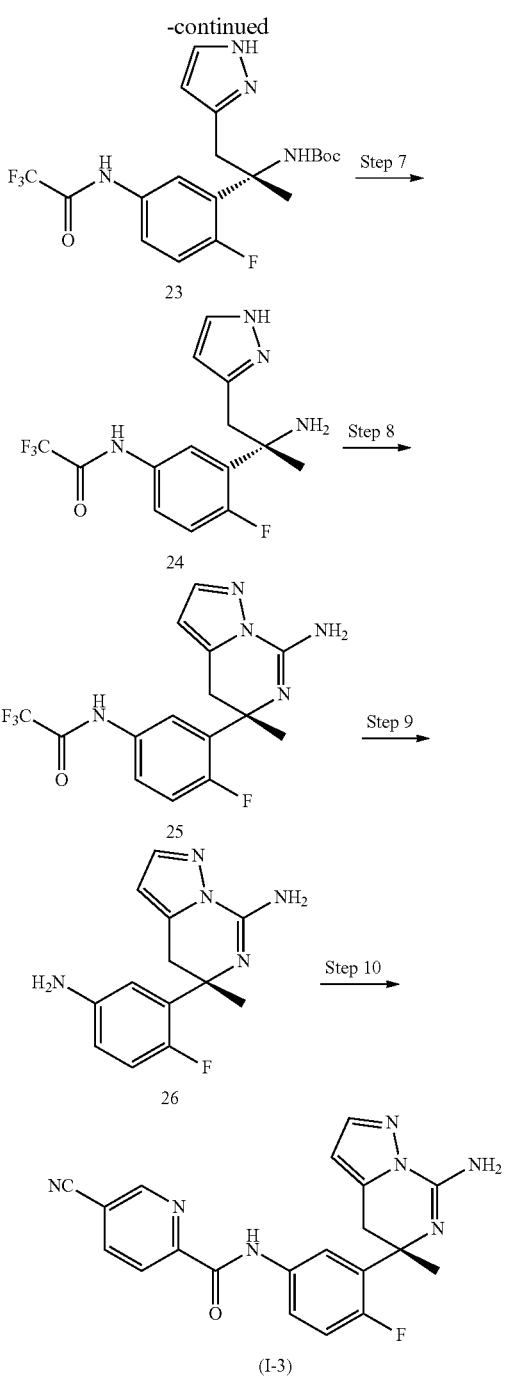

Step 1

Compound 17 (3.00 g) which can be prepared in a manner described in WO2009/151098 was dissolved in tetrahydrofuran (30 ml) under nitrogen atmosphere, and the solution was cooled in a dry ice acetone bath. To the solution was added dropwise 2-methyl allylmagnesium chloride (0.5M THF solution, 85.0 ml) at −78° C. and the mixture was stirred at −78° C. for 2 hours. To the reaction solution were added an aqueous saturated ammonium chloride solution and water, and extracted with ethyl acetate. The organic layer was washed sequentially with water and brine, and dried over anhydrous magnesium sulfate. The solvent was evaporated under reduced pressure and the obtained residue was purified by column chromatography to afford Compound 18 (2.49 g).

¹H-NMR (CDCl₃) δ: 1.26 (s, 9H), 1.38 (s, 3H), 1.86 (s, 3H), 2.84 (ABq, J=13.4 Hz, 2H), 4.21 (s, 1H), 4.81 (s, 1H), 4.92 (d, J=1.5 Hz, 1H), 7.74 (dd, J=6.8, 2.7 Hz, 1H), 7.05 (dd, J=11.7, 8.7 Hz, 1H), 7.45-7.51 (m, 1H), 8.37 (brs, 1H).
Step 2

A solution of Compound 18 (4.17 g) in dichloromethane (60 ml) was cooled in a dry ice acetone bath, and ozone gas was bubbled at −78° C. Bubbling was stopped when the color of the reaction solution changed to blue and nitrogen gas was introduced. To the reaction solution was added triethylamine (4.25 ml), and the mixture was stirred at −78° C. for 1 hour. To the reaction solution was added water and extracted with dichloromethane. The organic layer was washed with brine and dried over anhydrous magnesium sulfate. The solvent was evaporated under reduced pressure to afford Compound 19 (4.43 g).

¹H-NMR (CDCl₃) δ: 1.31 (s, 9H), 1.73 (s, 3H), 2.10 (s, 3H), 3.35 (dd, J=18.6, 2.5 Hz, 1H), 3.66 (d, J=18.6 Hz, 1H), 5.35 (s, 1H), 6.99 (dd, J=11.9, 8.7 Hz, 1H), 7.30-7.35 (m, 1H), 7.98 (dd, J=7.2, 2.7 Hz, 1H).
Step 3

To a solution of Compound 19 (4.19 g) in methanol (30 ml) was added a 4 mol/L hydrogen chloride-1,4-dioxane solution (3.57 ml) and the mixture was stirred at room temperature for 2 hours. The solvent was evaporated under reduced pressure and water was added to the obtained residue. The aqueous layer was extracted with diethyl ether and then the organic layer was washed with water. The combined aqueous layer was made alkaline using an aqueous saturated sodium bicarbonate solution and extracted with ethyl acetate. The organic layer was washed with water and brine and dried over anhydrous magnesium sulfate. The solvent was evaporated under reduced pressure to afford Compound 20 (3.00 g).

¹H-NMR (CDCl₃) δ: 1.48 (s, 3H), 2.06 (s, 3H), 2.18 (br, 2H), 2.86 (d, J=17.8 Hz, 1H), 3.44 (d, J=17.8 Hz, 1H), 7.01 (dd, J=11.7, 8.7 Hz, 1H), 7.60-7.70 (m, 2H), 8.17 (br, 1H).
Step 4

To a solution of Compound 20 (500 mg) in THF (5 ml) was added di-tert-butyl dicarbonate (534 mg), and the mixture was stirred at room temperature for 15 hours and at 60° C. for 5 hours. The solvent was evaporated under reduced pressure and the obtained residue was purified by column chromatography to afford Compound 21 (607 mg).

¹H-NMR (CDCl₃) δ: 1.41 (s, 9H), 1.80 (s, 3H), 2.10 (s, 3H), 3.10 (d, J=16.3 Hz, 1H), 3.46 (d, J=16.3 Hz, 1H) 5.79 (s, 1H), 7.53 (dd, J=7.1, 2.7 Hz, 1H) 7.00 (dd, J=11.8, 8.7 Hz, 1H), 7.43-7.52 (m, 1H), 8.19 (brs, 1H).
Step 5

To a solution of Compound 21 (450 mg) in DMF (5 ml) was added tert-butoxybis(dimethylamino)methane (965 mg) and the mixture was stirred at 80° C. for 5 hours. To the reaction solution was added water and extracted with ethyl acetate. The organic layer was washed sequentially with water and brine and dried over anhydrous magnesium sulfate. The solvent was evaporated under reduced pressure and the obtained residue was purified by column chromatography to afford Compound 22 (495 mg).

¹H-NMR (CDCl₃) δ: 1.41 (s, 9H), 1.88 (s, 3H) 2.59 (d, J=13.6 Hz, 1H), 2.73 (brs, 3H), 3.01 (m, 1H), 3.04 (brs, 3H), 4.81 (d, J=12.4 Hz, 1H) 6.97 (dd, J=11.6, 8.9 Hz, 1H), 7.13 (br, 1H), 7.37 (dd, J=7.1, 2.7 Hz, 1H), 7.40-7.57 (m, 2H), 8.28 (br, 1H).
Step 6

To a solution of Compound 22 (495 mg) in ethanol (10 ml) was added hydrazine acetate (148 mg) and refluxed for 1 hour. The solvent was evaporated under reduced pressure. To the residue was added water and extracted with ethyl acetate. The organic layer was washed sequentially with 1 mol/L hydrochloric acid, water, an aqueous saturated sodium bicarbonate solution, water and brine. The organic layer was dried over anhydrous magnesium sulfate and the solvent was evaporated under reduced pressure to afford Compound 23 (316 mg).

¹H-NMR (CDCl₃) δ: 1.37 (brs, 9H), 1.72 (brs, 3H) 3.16 (d, J=13.7 Hz, 1H), 3.47 (br, 1H), 5.64 (br, 1H), 5.84 (br, 1H), 7.03 (dd, J=11.7, 9.1 Hz, 1H), 7.30-7.60 (m, 3H), 8.83 (br, 1H).
Step 7

To a solution of Compound 23 (285 mg) in dichloromethane (10 ml) was added trifluoroacetic acid (1.0 ml), and the mixture was stirred at room temperature for 3 hours. The reaction solution was concentrated under reduced pressure. To the residue was added an aqueous saturated sodium bicarbonate solution and extracted with chloroform. The organic layer was dried over anhydrous magnesium sulfate and the solvent was evaporated under reduced pressure to afford Compound 24 (161 mg).

¹H-NMR (CDCl₃) δ: 1.57 (s, 3H), 3.09 (d, J=14.8 Hz, 1H), 3.39 (d, J=14.8 Hz, 1H), 5.86 (d, J=2.0 Hz, 1H), 7.08 (dd, J=11.9, 8.9 Hz, 1H), 7.39 (d, J=2.0 Hz, 1H), 7.52 (dd, J=6.9, 2.7 Hz, 1H), 7.58-7.64 (m, 1H), 9.20 (br, 1H).
Step 8

A solution of Compound 24 (162 mg) in acetonitrile (2 ml) was cooled in an ice bath. To the solution was added 9-fluorenemethoxycarbonyl isothiocyanate (138 mg), and the mixture was stirred at 0° C. for 1 hour. To the reaction solution were added methyl iodide (139 mg) and N,N-diisopropylethylamine (317 mg), and the mixture was stirred at room temperature for 1 hour and at 80° C. for 16 hours. After the reaction solution was cooled to room temperature, piperidine (50.1 mg) was added and stirred at room temperature for 20 hours. The solvent was evaporated under reduced pressure. To the residue were added an aqueous saturated sodium bicarbonate solution and water, and extracted with chloroform. The organic layer was dried over anhydrous magnesium sulfate and the solvent was evaporated under reduced pressure. The obtained residue was purified by column chromatography to afford Compound 25 (125 mg).

¹H-NMR (CDCl₃) δ: 1.57 (s, 3H), 3.33 (d, J=16.5 Hz, 1H) 3.40 (d, J=16.5 Hz, 1H), 6.13 (s, 1H), 7.06 (dd, J=11.6, 8.7 Hz, 1H), 7.50 (s, 1H), 7.69-7.75 (m, 1H), 7.78 (dd, J=6.9, 2.9 Hz, 1H).
Step 9

To a solution of Compound 25 (124 mg) in methanol (7.5 ml) were added potassium carbonate (289 mg), THF (2.5 ml) and water (2.5 ml), and stirred at 40° C. for 24 hours. The solvent was evaporated under reduced pressure, then water was added to the residue and extracted with chloroform. The organic layer was dried over anhydrous magnesium sulfate. The solvent was evaporated under reduced pressure to afford Compound 26 (74.4 mg).

¹H-NMR (CDCl₃) δ: 1.58 (s, 3H), 3.29 (d, J=16.2 Hz, 1H), 3.41 (d, J=16.2 Hz, 1H), 3.60 (br, 2H), 5.00 (br, 2H), 6.08 (d, J=1.5 Hz, 1H), 6.43-6.50 (m, 1H), 6.79 (dd, J=11.9, 8.6 Hz, 1H), 7.00 (dd, J=7.1, 3.0 Hz, 1H), 7.48 (d, J=1.5 Hz, 1H).
Step 10

To a solution of Compound 26 (27.2 mg) in methanol (1 ml) was added 2 mol/L hydrochloric acid (0.06 ml), and stirred at room temperature for 10 minutes. To the mixture were added 5-cyanopicolinic acid hydrate (26.1 mg), EDC hydrochloride (30.2 mg) and methanol (1 ml), and stirred at room temperature for 4 hours. The solvent was evaporated under reduced pressure. To the residue were added an aqueous saturated sodium bicarbonate solution and water, and extracted with chloroform. The organic layer was dried over anhydrous magnesium sulfate and the solvent was evaporated under reduced pressure. The obtained residue was purified by column chromatography to afford Compound (I-3) (32.9 mg).

Example 4

Synthesis of Compound (I-4)

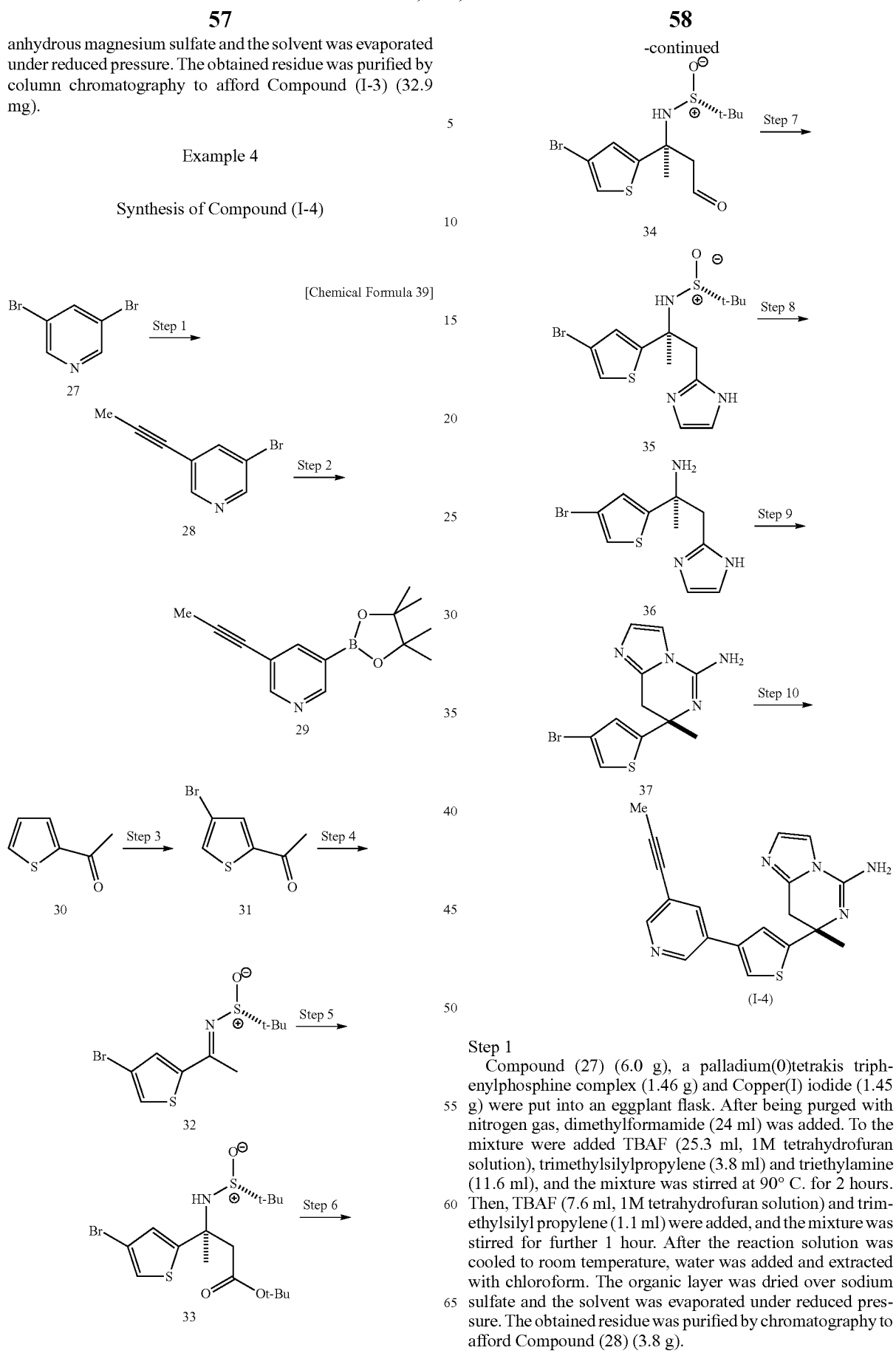

Step 1

Compound (27) (6.0 g), a palladium(0)tetrakis triphenylphosphine complex (1.46 g) and Copper(I) iodide (1.45 g) were put into an eggplant flask. After being purged with nitrogen gas, dimethylformamide (24 ml) was added. To the mixture were added TBAF (25.3 ml, 1M tetrahydrofuran solution), trimethylsilylpropylene (3.8 ml) and triethylamine (11.6 ml), and the mixture was stirred at 90° C. for 2 hours. Then, TBAF (7.6 ml, 1M tetrahydrofuran solution) and trimethylsilyl propylene (1.1 ml) were added, and the mixture was stirred for further 1 hour. After the reaction solution was cooled to room temperature, water was added and extracted with chloroform. The organic layer was dried over sodium sulfate and the solvent was evaporated under reduced pressure. The obtained residue was purified by chromatography to afford Compound (28) (3.8 g).

$^1$H-NMR (CDCl$_3$) δ: 2.07 (s, 3H), 7.80 (dd, J=2.1, 1.8 Hz, 1H), 8.50 (d, J=1.8 Hz, 1H), 8.53 (d, J=2.1 Hz, 1H).

Step 2

Compound (28) (500 mg), diboron pinacol ester (1.17 g), potassium acetate (751 mg) and a palladium(0)tetrakistriphenylphosphine complex (295 mg) were put into an eggplant flask. After being purged with nitrogen gas, dioxane (20 ml) was added and stirred at 110° C. for 2.5 hours. The reaction solution was cooled to room temperature and made acidic using water and a 2 mol/L aqueous hydrochloric acid solution. The impurity was removed by back-extraction with ethyl acetate. The aqueous layer was made alkaline using sodium hydroxide and the product was extracted to the organic layer with ethyl acetate. The organic layer was dried over sodium sulfate and the solvent was evaporated under reduced pressure to afford Compound (29) (508 mg).

$^1$H-NMR (CDCl$_3$) δ: 1.34 (s, 12H), 2.06 (s, 3H), 8.06 (dd, J=2.2, 1.7 Hz, 1H), 8.66 (d, J=2.2 Hz, 1H), 8.79 (d, J=1.7 Hz, 1H).

Step 3

To a solution of Compound (30) (30 g) in chloroform (60 ml) were added trimethyl aluminium (33.3 g) and bromine (12.9 ml) at 0° C. The mixture was stirred at room temperature for 1 hour, warmed to 50° C. and stirred for 2 hours. After addition of trimethyl aluminium (16.0 g), the mixture was stirred for 1 hour and cooled to room temperature. To the reaction solution was added sodium acetate and filtered through Celite. The filtrate was extracted with chloroform and dried over sodium sulfate. The solvent was evaporated under reduced pressure and the obtained residue was purified by chromatography to afford Compound (31) (40 g).

$^1$H-NMR (CDCl$_3$) δ: 2.56 (s, 3H), 7.53 (d, J=1.4 Hz, 1H), 7.58 (d, J=1.4 Hz, 1H).

Step 4

To a solution of Compound (31) (27 g) in tetrahydrofuran (150 ml) were added (R)-2-methylproane-2-sulfinamide (20 g) and the titanium tetraethoxide (38.6 ml). The mixture was stirred at 70° C. for 3.5 hours and at 90° C. for 6 hours. To the mixture was added brine and filtered through Celite. The filtrate was extracted with ethyl acetate and dried over sodium sulfate. The solvent was evaporated under reduced pressure and the obtained residue was purified by chromatography to afford Compound (32) (30.1 g).

$^1$H-NMR (CDCl$_3$) δ: 1.30 (s, 9H), 2.71 (s, 3H), 7.39 (d, J=1.4 Hz, 1H), 7.41 (d, J=1.4 Hz, 1H).

Step 5

To tetrahydrofuran (70 ml) in an eggplant flask were added lithium diisopropylamide (100 ml, 2M), t-butyl acetate (26.4 ml) and triisopropoxy titanium (IV) chloride (98 ml) at a temperature between −70° C. and −60° C., and stirred for 1 hour. To the mixture were added Compound (32) (30.1 g) and tetrahydrofuran (80 ml), and stirred at a temperature between −60° C. and −50° C. for 1.5 hours. After addition of an aqueous saturated ammonium chloride solution, the mixture was filtered through Celite and the filtrate was dried over sodium sulfate. The solvent was evaporated under reduced pressure and the obtained residue was purified by chromatography to afford Compound (33) (13.4 g).

$^1$H-NMR (CDCl$_3$) δ: 1.29 (s, 9H), 1.37 (s, 9H), 1.79 (s, 3H), 2.89 (d, J=15.8 Hz, 1H), 2.99 (d, J=15.8 Hz, 1H), 5.74 (s, 1H), 6.81 (d, J=1.4 Hz, 1H), 7.09 (d, J=1.4 Hz, 1H).

Step 6

Compound (33) (13.4 g) was dissolved in toluene (50 ml), and DIBAL (158 ml, 1M hexane solution) was added at −70° C. After stirring at 0° C. for 2 hours, ethyl acetate and an aqueous Rochelle salt solution were added and extracted. The organic layer was washed with water and dried over sodium sulfate. The solvent was evaporated under reduced pressure and the obtained residue was purified by chromatography to afford Compound (34) (2.26 g).

$^1$H-NMR (CDCl$_3$) δ: 1.27 (s, 9H), 1.78 (s, 3H) 3.26 (dd, J=18.1, 1.1 Hz, 1H), 3.33 (d, J=18.1 Hz, 1H), 5.04 (s, 1H), 6.79 (d, J=1.4 Hz, 1H), 7.12 (d, J=1.4 Hz, 1H), 9.73 (d, J=1.1 Hz, 1H).

Step 7

To a 40% aqueous glyoxal solution (868 mg) in an eggplant flask were added water (2 ml) and ammonium carbonate (946 mg) and stirred at room temperature for 10 minutes. To the mixture were added Compound (34) (439 mg) and methanol (8 ml), and the mixture was stirred at room temperature overnight. To the reaction mixture were added an aqueous saturated sodium hydrogen carbonate solution and ethyl acetate, and extracted. The organic layer was dried over sodium sulfate and the solvent was evaporated under reduced pressure to afford Compound (35) (371 mg).

$^1$H-NMR (CDCl$_3$) δ: 1.31 (s, 9H), 1.71 (s, 3H), 3.20 (d, J=14.7 Hz, 1H), 3.39 (d, J=14.7 Hz, 1H), 5.77 (s, 1H), 6.90 (s, 1H), 6.94 (d, J=1.4 Hz, 1H), 7.06 (s, 1H), 7.08 (d, J=1.4 Hz, 1H), 7.61 (s, 1H).

Step 8

To a solution of Compound (35) (371 mg) in methanol (5 ml) was added concentrated hydrochloric acid (580 μl) at 0° C. and stirred at room temperature for 1.5 hours. To the mixture were added an aqueous saturated sodium hydrogen carbonate solution and ethyl acetate, and extracted. The organic layer was dried over sodium sulfate and the solvent was evaporated under reduced pressure to afford Compound (36) (313 mg, quant).

$^1$H-NMR (CDCl$_3$) δ: 1.51 (s, 3H), 3.13 (d, J=15.0 Hz, 1H), 3.14 (d, J=15.0 Hz, 1H), 6.79 (d, J=1.4 Hz, 1H), 6.94 (s, 1H), 7.06 (d, J=1.4 Hz, 1H), 7.09 (s, 1H), 7.65 (s, 1H).

Step 9

To a solution of Compound (36) (313 mg) in acetonitrile (5 ml) was added Fmoc NCS (281 mg) at 0° C. and stirred at room temperature for 1 hour. To the mixture were added iodomethane (119 μl) and diisopropylethylamine (830 μl), and the mixture was stirred at 80° C. for 1 hour. Piperidine (282 μl) was added and the mixture was stirred at room temperature for 4.5 hours. To the mixture were added water and ethyl acetate, extracted, and dried over sodium sulfate. The solvent was evaporated under reduced pressure and the obtained residue was purified by chromatography and recrystallization to afford Compound (37) (91 mg).

$^1$H-NMR (CDCl$_3$) δ: 1.58 (s, 3H), 3.20 (d, J=16.2 Hz, 1H) 3.30 (d, J=16.2 Hz, 1H), 6.81 (d, J=1.3 Hz, 1H), 7.00 (d, J=1.7 Hz, 1H), 7.05 (d, J=1.3 Hz, 1H), 7.12 (d, J=1.7 Hz, 1H).

Step 10

Compound (37) (48.0 mg), Compound (3) (52.5 mg), a palladium(0) tetrakistriphenylphosphine complex (35.6 mg) and sodium carbonate (65.4 mg) were put into an eggplant flask. After being purged with nitrogen gas, dioxane (6 ml) and water (0.6 ml) were added and the solution was stirred at 110° C. for 2 hours. After the reaction solution was cooled to room temperature, it was made acidic using water and a 2 mol/L aqueous hydrochloric acid solution. The impurity was removed by back-extraction with ethyl acetate. The aqueous layer was made alkaline using sodium carbonate and the product was extracted to the organic layer with ethyl acetate. The organic layer was dried over sodium sulfate and the solvent was evaporated under reduced pressure. The obtained residue was purified by chromatography and recrystallization to afford Compound (I-4) (12.2 mg).

Example 5

Synthesis of Compound (I-7)

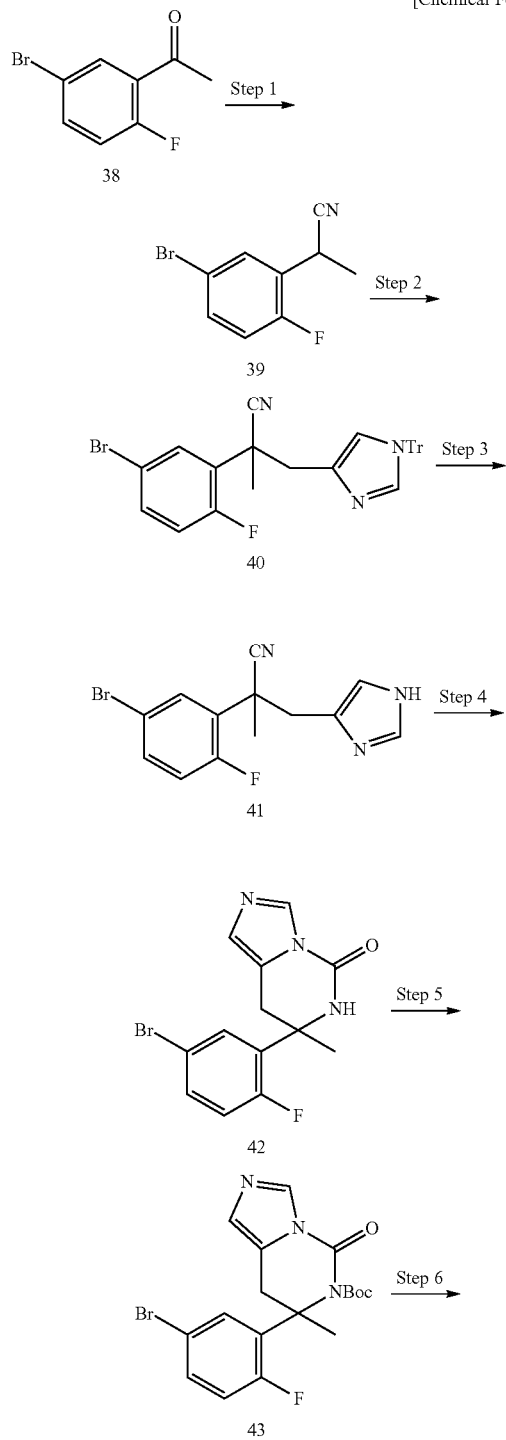

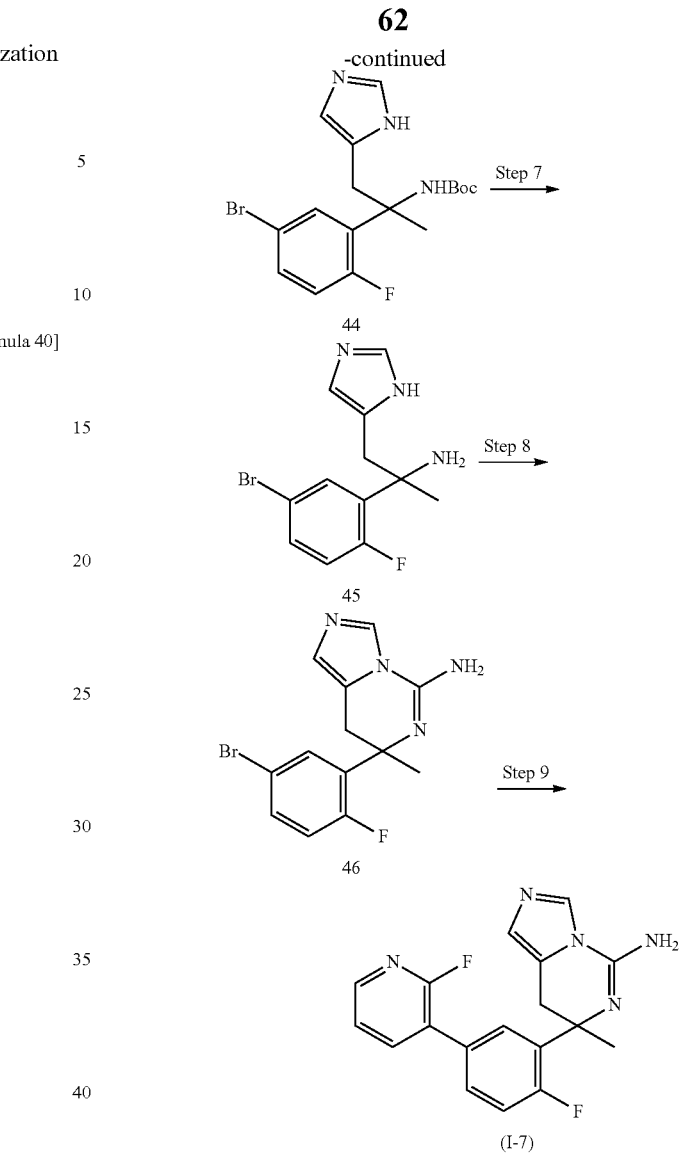

Step 1

To a solution of Compound (38) (7.00 g) in ethanol (50 ml) were added p-toluenesulfonylmethyl isocyanide (9.45 g) and potassium carbonate (8.92 g) at room temperature, and stirred under reflux for 1.5 hours. To the mixture were added 2 mol/L hydrochloric acid and diethyl ether and the organic layer was washed with water and brine. The organic layer was dried over sodium sulfate and the solvent was evaporated under reduced pressure. The obtained residue was purified by chromatography to afford Compound (39) (3.29 g).

$^1$H-NMR (DMSO-$d_6$) δ: 1.57 (d, J=7.1 Hz, 3H), 4.46 (q, J=7.1 Hz, 1H), 7.30 (t, J=9.3 Hz, 1H), 7.58-7.73 (m, 2H).

Step 2

To a solution of diisopropylamine (1.20 ml) in tetrahydrofuran (50 ml) was added 2.66 mol/L butyllithium (2.90 ml) at −78° C. and stirred at −78° C. for 30 minutes. To the reaction solution was added a solution of Compound (39) (1.60 g) in tetrahydrofuran (20 ml) and stirred at −30° C. for 20 minutes. To the solution was added a solution of 4-chloromethyl-1-tritylimidazole (2.77 g) in tetrahydrofuran (30 ml) and stirred at room temperature for 4 hours. To the mixture were added sequentially an aqueous saturated ammonium chloride solution and ethyl acetate, and the organic layer was washed with water and brine. The organic layer was dried over sodium sulfate and the solvent was evaporated under reduced pressure. The obtained residue was purified by chromatography to afford Compound (40) (2.56 g).

$^1$H-NMR (DMSO-d$_6$) δ: 1.80 (s, 3H), 3.20 (s, 2H) and 6.42 (s, 1H), 6.93-6.99 (m, 6H), 7.20-7.25 (m, 2H), 7.34-7.44 (m, 10H), 7.59-7.67 (m, 1H).

Step 3

To a solution of Compound (40) (2.42 g) in dichloromethane (7.0 ml) was added trifluoroacetic acid (6.77 ml) at room temperature and stirred for 3.5 hours. To the mixture were added sequentially an aqueous potassium carbonate solution and ethyl acetate, and the organic layer was washed with water and brine. The residue was purified by chromatography to afford Compound (41) (651 mg).

$^1$H-NMR (DMSO-d$_6$) δ: 1.77 (s, 3H), 3.15 (d, J=14.1 Hz, 1H), 3.26 (d, J=14.1 Hz, 1H), 6.83 (s, 1H), 7.29 (t, J=9.6 Hz, 1H), 7.47-7.54 (m, 2H), 7.66-7.56 (m, 1H), 11.88 (br s, 1H).

Step 4

Compound (41) (651 mg) was dissolved in concentrated hydrochloric acid (19 ml), and the solution was stirred at 100° C. for 23 hours. Then, concentrated hydrochloric acid was evaporated under reduced pressure and the obtained residue was dissolved in toluene (14 ml). To the solution were added triethylamine (0.878 ml) and diphenylphosphoryl azide (1.37 ml) and stirred at 80° C. for 15 hours. To the mixture were added sequentially water and chloroform, and the organic layer was washed with water and brine. The organic layer was dried over sodium sulfate the solvent was evaporated under reduced pressure. The obtained residue was purified by chromatography to afford Compound (42) (375 mg).

$^1$H-NMR (DMSO-d$_6$) δ: 1.65 (s, 3H), 3.12 (d, J=16.2 Hz, 1H) 3.65 (d, J=16.2 Hz, 1H), 8.08 (s, 1H) 6.74 (s, 1H), 7.21 (dd, J=7.6, 11.6 Hz, 1H), 7.33 (d, J=7.6 Hz, 1H), 7.55-7.48 (m, 1H), 8.98 (s, 1H).

Step 5

To a solution of Compound (42) (358 mg) in tetrahydrofuran (13 ml) were added di-tert-butyl dicarbonate (2.56 ml) and 4,4-dimethylaminopyridine (13.5 mg) at room temperature and stirred for 17 hours. The solvent was evaporated under reduced pressure and the obtained residue was purified by chromatography to afford Compound (43) (243 mg).

$^1$H-NMR (DMSO-d$_6$) δ 1.32 (s, 9H), 1.82 (s, 3H) 3.29 (d, J=15.7 Hz, 1H), 3.56 (d, J=15.7 Hz, 1H), 6.84 (s, 1H), 7.21-7.29 (m, 1H), 7.64-7.52 (m, 2H), 8.26 (s, 1H).

Step 6

Compound (43) (242 mg) was dissolved in ethanol (2 ml) and water (1 ml). To the solution was added barium hydroxide octahydrate (540 mg) at room temperature and the mixture was stirred for 1 hour. To the mixture were added an aqueous citric acid solution and ethyl acetate, and the organic layer was washed with water and brine. The organic layer was dried over sodium sulfate and the solvent was evaporated under reduced pressure to afford Compound (44) (228 mg).

$^1$H-NMR (DMSO-d$_6$) δ: 1.37 (s, 9H), 1.63 (s, 3H), 2.86-2.96 (m, 1H), 3.01-3.12 (m, 1H), 6.65 (br s, 1H), 7.11-7.58 (m, 5H), 11.85 (br s, 1H).

Step 7

To Compound (44) (175 mg) was added trifluoroacetic acid (1.52 ml) at room temperature, and the mixture was stirred for 20 minutes. To the mixture were adeded an aqueous potassium carbonate solution and ethyl acetate, and the organic layer was washed with water and brine. The organic layer was dried over sodium sulfate and the solvent was evaporated under reduced pressure to afford Compound (45) (125 mg).

$^1$H-NMR (DMSO-d$_6$) δ: 1.38 (s, 3H), 2.89 (d, J=14.1 Hz, 1H) 3.05 (d, J=14.1 Hz, 1H), 6.53 (s, 1H), 7.07 (dd, J=8.6, 11.6 Hz, 1H), 7.35-7.41 (m, 1H), 7.44 (s, 1H), 7.69-7.64 (m, 1H).

Step 8

Compound (45) (125 mg) was dissolved in acetonitrile (2.0 ml) and was added 9-fluorenyl methyloxycarbonyl isothiocyanate (118 mg) under ice-cooling. After stirring at room temperature for 20 minutes, were added diisopropylethylamine (0.366 ml) and methyl iodide (0.105 ml). The mixture was stirred at room temperature for 1.5 hours and at 80° C. for 4 hours. To the mixture was added piperidine (0.0830 ml) and stirred at room temperature for 1 hour. To the mixture were added water and chloroform, and the organic layer was washed with brine. The organic layer was dried over sodium sulfate and the solvent was evaporated under reduced pressure. The obtained residue was purified by chromatography to afford Compound (46) (83.0 mg).

$^1$H-NMR (DMSO-d$_6$) δ: 1.32 (s, 3H), 2.96 (d, J=15.7 Hz, 1H) 3.22 (d, J=15.7 Hz, 1H), 6.66-6.86 (m, 3H), 7.16 (dd, J=9.1, 11.1 Hz, 1H), 7.42-7.51 (m, 1H), 7.96-7.89 (m, 1H), 8.05 (s, 1H).

Step 9

Compound (46) (39.0 mg), 2-fluoropyridine-3-boronic acid (85.0 mg), [1,1'-bis(di-tert-butylphosphino)ferrocene] palladium (II) dichloride (15.7 mg) and potassium carbonate (50.0 mg) were dissolved in dioxane (1.5 ml) and water (0.15 ml). The solution was stirred under microwave irradiation at 170° C. for 1 hour. To the mixture were added water and ethyl acetate, and the organic layer was washed with brine. The organic layer was dried over sodium sulfate, and the solvent was evaporated under reduced pressure. The obtained residue was purified by chromatography and solidified in hexane-ethyl acetate to afford Compound (I-7) (22.4 mg)

Example 6

Synthesis of Compound (I-6)

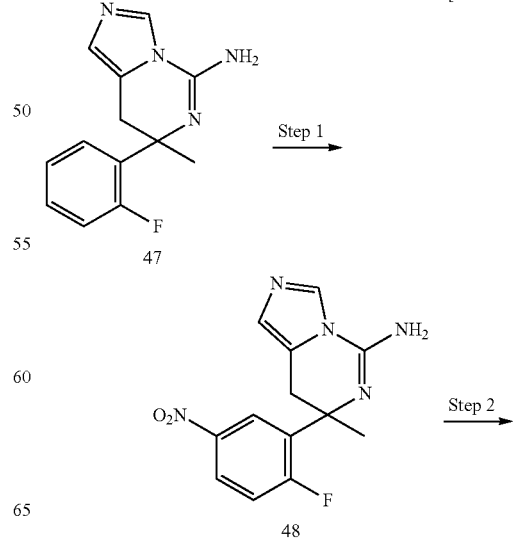

[Chemical Formula 41]

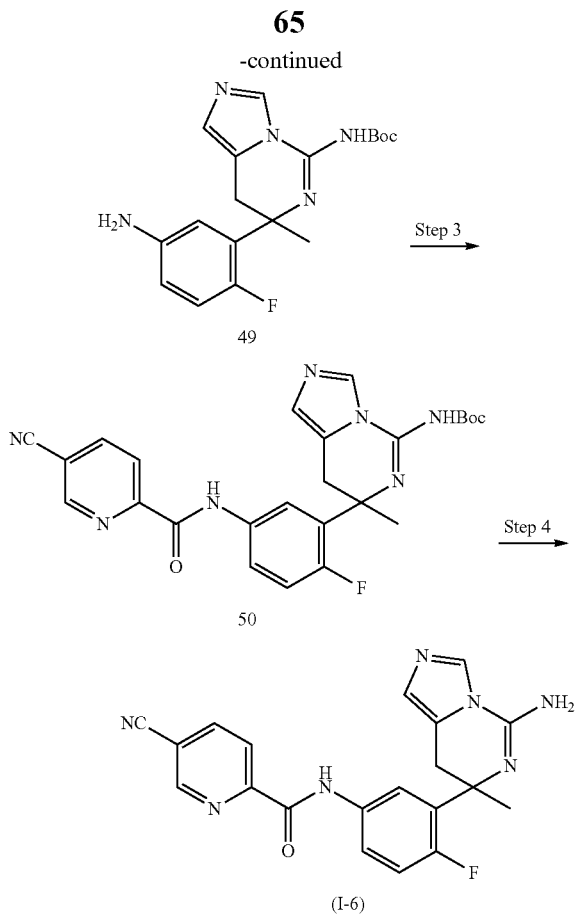

Step 1

Compound (47) (100 mg) synthesized in a similar manner to Example 5 was dissolved in sulfuric acid (0.455 ml). To the solution was added nitric acid (27.4 μl under ice-cooling and stirred for 20 minutes. After the reaction solution was poured into ice, were added a 2 mol/L aqueous sodium hydroxide solution and chloroform, and the organic layer was washed with brine. The organic layer was dried over sodium sulfate and the solvent was evaporated under reduced pressure to afford Compound (48) (118 mg).

$^1$H-NMR (DMSO-d$_6$) δ: 1.33 (s, 3H), 2.95 (d, J=14.7 Hz, 1H), 6.82 (br s, 3H), 7.49 (t, J=9.9 Hz, 1H), 8.07 (s, 1H), 8.17-8.23 (m, 1H), 8.77-8.70 (m, 1H).

Step 2

To a solution of Compound (48) (118 mg) in tetrahydrofuran (1.8 ml) was added di-tert-butyl dicarbonate (95 μl) at room temperature. After stirring for 14 hours, methanol (1.2 ml), distilled water (0.48 ml), iron (128 mg) and ammonium chloride (98 mg) were added at room temperature and the mixture was stirred at 70° C. for 2.5 hours. The reaction solution was filtered and water, an aqueous saturated sodium hydrogen carbonate solution and ethyl acetatewere added to the filtrate. The organic layer was washed with water and brine and dried over sodium sulfate. The solvent was evaporated under reduced pressure and the obtained residue was purified by chromatography to afford Compound (49) (44.0 mg).

$^1$H-NMR (DMSO-d$_6$) δ: 1.47 (s, 9H), 1.70 (s, 3H) 3.20 (d, J=15.2 Hz, 1H), 3.62 (d, J=15.2 Hz, 1H) 5.02 (s, 2H), 8.13 (s, 1H) 6.34-6.40 (m, 1H), 6.41-6.48 (m, 1H), 6.91-6.83 (m, 2H), 9.85 (s, 1H).

Step 3

To a solution of Compound (49) (44.0 mg) in tetrahydrofuran (1.0 ml) were added 5-cyano picolinic acid monohydrate (24.4 mg), triethylamine (44 μl) and O-(benzotriazole-1-yl)-N,N,N',N'-tetramethyluroniumhexafluorophosphate (60.5 mg) under ice-cooling. The mixture was stirred at room temperature for 1 hour. To the mixture were added an aqueous saturated sodium hydrogen carbonate solution and ethyl acetate, and the organic layer was washed with water and brine. The organic layer was dried over sodium sulfate and the solvent was evaporated under reduced pressure. The obtained residue was purified by chromatography to afford Compound (50) (59.9 mg).

$^1$H-NMR (DMSO-d$_6$) δ: 1.49 (s, 9H), 1.77 (s, 3H), 3.29 (d, J=15.2 Hz, 1H), 3.72 (d, J=15.2 Hz, 1H), 6.87 (s, 1H), 7.27 (t, J=10.1 Hz, 1H) 7.84-7.90 (m, 1H), 7.96-7.91 (m, 1H), 8.14 (s, 1H), 8.25 (d, J=8.1 Hz, 1H), 8.57 (d, J=8.1 Hz, 1H), 9.17 (s, 1H), 9.97 (s, 1H), 10.91 (s, 1H).

Step 4

Compound (50) (59.9 mg) was dissolved in formic acid (1.4 ml), and stirred at room temperature for 15 hours. To the solution were added an aqueous potassium carbonate solution and ethyl acetate and the organic layer was washed with water and brine. The organic layer was dried over sodium sulfate, and the solvent was evaporated under reduced pressure. The obtained residue was purified by chromatography, and solidified in hexane-ethyl acetate to afford Compound (I-6) (6.0 mg).

The following compounds are prepared in a similar manner to the above.

TABLE 1

| Compound No. | Structure | NMR (Solvent: Shift value ascending order) | LC/MS RT |
|---|---|---|---|
| I-1 | 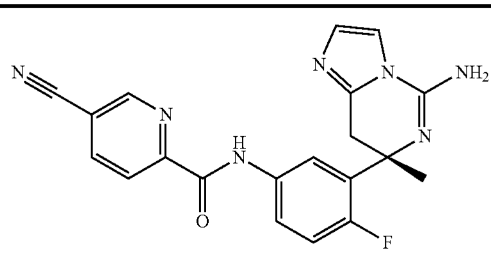 | 1H-NMR (CDCl3) δ: 1.63 (s, 3H), 3.45 (m, 4H), 6.97 (d, J = 1.5 Hz, 1H), 7.09 (dd, J = 11.8, 8.7 Hz, 1H), 7.23 (br, 1H), 7.79 (dd, J = 8.7, 4.2 Hz, 1H), 7.87 (br, 1H), 8.18 (dd, J = 8.1, 2.0 Hz, 1H), 8.39 (dd, J = 8.1, 0.8 Hz, 1H), 8.86 (d, J = 0.8 Hz, 1H), 9.80 (brs, 1H). | 0.93 |

TABLE 1-continued

| Compound No. | Structure | NMR (Solvent: Shift value ascending order) | LC/MS RT |
|---|---|---|---|
| I-2 | 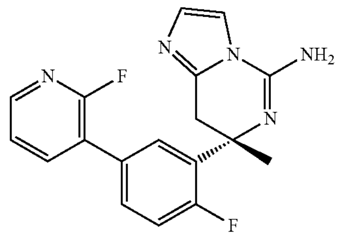 [SMILES: C[C@@]1(c2cc(-c3cccnc3F)ccc2F)Cc2nccn2C(N)=N1] | 1H-NMR (CDCl3) δ: 1.65 (brs, 3H), 3.41 (br, 2H), 4.83 (br, 2H), 6.97 (s, 1H), 7.14 (dd, J = 11.7, 8.6 Hz, 1H), 7.22-7.28 (m, 1H), 7.40-7.45 (m, 1H), 7.77 (br, 2H), 8.18 (dd, J = 3.2, 1.8 Hz, 1H). | 0.85 |
| I-3 | 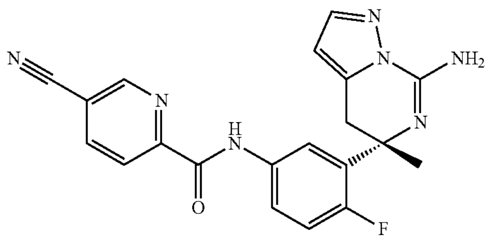 [SMILES: C[C@@]1(c2cc(NC(=O)c3ccc(C#N)cn3)ccc2F)Cc2ccnn2C(N)=N1] | 1H-NMR (CDCl3) δ: 1.61 (s, 3H), 3.36 (d, J = 16.3 Hz, 1H), 3.44 (d, J = 16.3 Hz, 1H), 5.00 (br, 2H), 6.14 (d, J = 1.5 Hz, 1H), 7.06 (dd, J = 11.8, 8.7 Hz, 1H), 7.49 (d, J = 1.5 Hz, 1H), 7.86-7.96 (m, 2H), 8.16 (dd, J = 8.2, 2.0 Hz, 1H), 8.36 (dd, J = 8.2, 0.8 Hz, 1H), 8.77 (d, J = 0.8 Hz, 1H), 9.80 (brs, 1H). | 0.95 |
| I-4 | 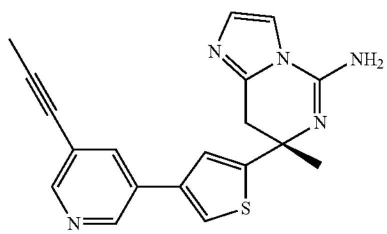 [SMILES: CC#Cc1cncc(-c2csc([C@]3(C)Cc4nccn4C(N)=N3)c2)c1] | 1H-NMR (CDCl3) δ: 1.66 (s, 3H), 2.09 (s, 3H), 3.25 (d, J = 16.1 Hz, 1H), 3.36 (brs, 2H), 3.41 (d, J = 16.1 Hz, 1H), 6.99 (d, J = 1.4 Hz, 1H), 7.14 (d, J = 1.4 Hz, 1H), 7.16 (d, J = 1.4 Hz, 1H), 7.32 (d, J = 1.4 Hz, 1H), 7.77 (dd, J = 2.1, 2.0 Hz, 1H), 8.49 (d, J = 2.0 Hz, 1H), 8.64 (d, J = 2.1 Hz, 1H). | 0.95 |
| I-5 | 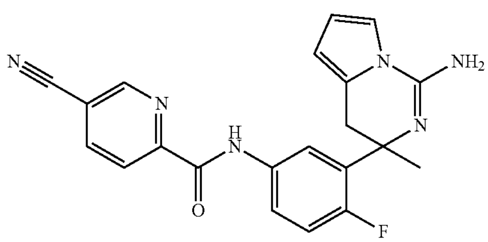 [SMILES: CC1(c2cc(NC(=O)c3ccc(C#N)cn3)ccc2F)Cc2cccn2C(N)=N1] | | |
| I-6 | 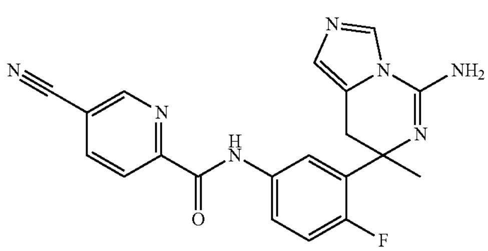 [SMILES: CC1(c2cc(NC(=O)c3ccc(C#N)cn3)ccc2F)Cc2cncn2C(N)=N1] | 1H-NMR (DMSO-d6) δ: 1.40 (3H, s), 3.11 (2H, s), 6.65 (2H, br s), 6.75 (1H, s), 7.15 (1H, t, J = 10.9 Hz), 7.68-7.76 (1H, m), 8.02 (1H, s), 8.04-8.11 (1H, m), 8.26 (1H, d, J = 8.6 Hz), 8.56 (1H, d, J = 8.6 Hz), 9.18 (1H, s), 10.73 (1H, s). | 1.02 |
| I-7 | 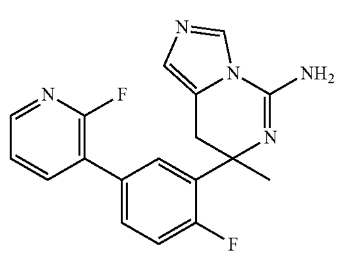 [SMILES: CC1(c2cc(-c3cccnc3F)ccc2F)Cc2cncn2C(N)=N1] | 1H-NMR (DMSO-d6) δ: 1.44 (3H, s), 3.11-3.24 (2H, m), 6.59-6.82 (3H, m), 7.29 (1H, t, J = 9.3 Hz), 7.43-7.53 (2H, m), 7.82-7.93 (1H, m), 7.96-8.06 (2H, m), 8.24 (1H, d, J = 3.0 Hz). | 0.97 |

Test Examples of compounds of the present invention are described below.

Test Example 1

Assay of BACE1 Inhibitory Activity 48.5 µL of substrate peptide solution (Biotin-XSEVNLDAEFRHDSGC-Eu: X=ε-amino-n-caproic acid, Eu=Europium cryptate) was added to each well of 96-hole half-area plate (a black plate: Costar), and after addition of 0.5 µl of the compound of the present invention (N,N'-dimethylformamide solution) and 1 µl of Recombinant human BACE-1 (R&D Systems), the reaction mixture was incubated at 30° C. for 3 hours. The substrate peptide was synthesized by reacting Cryptate TBPCOOH mono SMP (CIS bio international) with Biotin-XSEVNLDAEFRHDSGC (Peptide Institute, Inc.). The final concentrations of the substrate peptide and Recombinant human BACE1 were adjusted to 18 nmol/L and 7.4 nmol/L, respectively, and the reaction was performed in sodium acetate buffer (50 mmol/L sodium acetate, pH 5.0, 0.008% Triton X-100). After the incubation for reaction, 50 µl of 8.0 µg/ml Streptavidin-XL665 (CIS bio international) dissolved in phosphate buffer (150 mmol/L $K_2HPO_4$—$KH_2PO_4$, pH 7.0, 0.008% Triton X-100, 0.8 mol/L KF) was added to each well and left stand at 30° C. for 1 hour. After then, fluorescence intensity was measured (excitation wavelength: 320 nm, measuring wavelength: 620 nm and 665 nm) using Wallac 1420 multilabel counter (Perkin Elmer life sciences). Enzymatic activity was determined from counting ratio of each wavelength (10,000×Count 665/Count 620) and 50% inhibitory concentration against the enzymatic activity ($IC_{50}$) was calculated.

Compound I-3 showed the $IC_{50}$ value of 0.036 µmol/L

Compounds I-1, 2, 4, 6 and 7 showed the $IC_{50}$ values of 1 µmol/L, or less.

Test Example 2

Measurement of β-Amyloid (Aβ) Production Inhibiting Effect in Cell

Neuroblastoma SH-SY5Y cells (SH/APPwt) with human wild-type β-APP excessively expressed therein were prepared at $8×10^5$ cells/mL, and 150 µl portions thereof were inoculated into each well of a 96-well culture plate (Falcon). The cells were cultured for 2 hours at 37° C. in a 5% gaseous carbon dioxide incubator. Then, a solution which have been preliminarily prepared by adding and suspending the compound of the present invention (DMSO (dimethyl sulfoxide) solution) so as to be 2 µl/50 µl medium was added to the cell sap. Namely, the final DMSO concentration was 1%, and the amount of the cell culture was 200 µl. After the incubation was performed for 24 hours from the addition of the test compound, 100 µl of the culture supernatant was collected from each fraction. The amount of the Aβ in each fraction was measured.

The Aβ amount was measured as follows. 10 µl of a homogeneous time resolved fluorescence (HTRF) measurement reagent (Amyloid β 1-40 peptide; IBA Molecular Holding, S.A.) and 10 µl of the culture supernatant were put into a 384-well half area microplate (black microplate, Costar) and mixed with each other, and then left standing overnight at 4° C. while the light was shielded. Then, the fluorescence intensity (excitation wavelength: 337 nm, measurement wavelength: 620 nm and 665 nm) was measured with Wallac 1420 multilabel counter (Perkin Elmer life sciences). The Aβ amount was determined from the count rate at each measurement wavelength (10000×Count 665/Count 620), and the amount needed to inhibit Aβ production by 50% ($IC_{50}$) was calculated from at least six different dosages.

Compound I-3 showed the $IC_{50}$ value of 0.003 µmol/L. Compounds I-1, 2, 4, 6 and 7 showed the $IC_{50}$ values of 1 µmol/L or less.

Test Example 3

Lowering Effect on Brain β Amyloid in Rats

Compound of the present invention is suspended in 0.5% methylcellulose, the final concentration is adjusted to 2 mg/mL, and this is orally administered to male Crj:SD rat (7 to 9 weeks old) at 10 mg/kg. In a vehicle control group, only 0.5% methylcellulose is administered, and an administration test is performed at 3 to 8 animals per group. A brain is isolated 3 hours after administration, a cerebral hemisphere is isolated, a weight thereof is measured, the hemisphere is rapidly frozen in liquid nitrogen, and stored at −80° C. until extraction date. The frozen cerebral hemisphere is transferred to a homogenizer manufactured by Teflon (registered trade mark) under ice cooling, a 5-fold volume of a weight of an extraction buffer (containing 1% CHAPS ({3-[(3-chloroamidopropyl)dimethylammonio]-1-propanesulfonate}), 20 mmol/L Tris-HCl (pH 8.0), 150 mmol/L NaCl, Complete (Roche) protease inhibitor) is added, up and down movement is repeated, and this is homogenized to solubilize for 2 minutes. The suspension is transferred to a centrifugation tube, allowed to stand on an ice for 3 hours or more and, thereafter centrifuged at 100,000×g, 4° C. for 20 minutes. After centrifugation, the supernatant is transferred to an ELISA plate (product No. 294-62501, Wako Junyaku Kogyo) for measuring β amyloid 40. ELISA measurement is performed according to the attached instruction. The lowering effect is calculated as a ratio compared to the brain β amyloid 40 level of vehicle control group of each test.

Test Example 4

CYP3A4 Fluorescent MBI Test

The CYP3A4 fluorescent MBI test is a test of investigating enhancement of CYP3A4 inhibition of the compound of the present invention by a metabolism reaction. 7-benzyloxytrifluoromethylcoumarin (7-BFC) is debenzylated by the CYP3A4 enzyme (enzyme expressed in *Escherichia coli*) and a metabolite, 7-hydroxytrifluoromethylcoumarin (7-HFC) which emits fluorescent light is produced. The test is performed using 7-HFC production reaction as an index.

The reaction conditions are as follows: substrate, 5.6 mmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); concentration of the compound of the present invention, 0.625, 1.25, 2.5, 5, 10, 20 µmol/L (six points).

An enzyme in a K-Pi buffer (pH 7.4) and the compound of the present invention solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. NADPH was added to a remaining preincubation solution to initiate a pre-incubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving the compound of the present invention to a reaction system was adopted as a control (100%), remaining activity (%) was calculated at each concentration of the compound of the present invention added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

Compound I-1: (−)

Test Example 5

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a compound of the present invention was assessed.

The reaction conditions were as follows: substrate, 0.5 µmol/L ethoxyresorufin (CYP1A2), 100 µmol/L tolbutamide (CYP2C9), 50 µmol/L S-mephenyloin (CYP2C19), 5 mol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; concentration of the compound of the present invention, 1, 5, 10, 20 µmol/L (four points).

Each five kinds of substrates, human hepatic microsome, and a compound of the present invention in 50 mmol/L Hepes buffer as a reaction solution was added to a 96-well plate at the composition as described above. NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a multi-label counter and hydroxytolbutamide (CYP2C9 metabolite), 4'-hydroxymephenyloin (CYP2C19 metabolite), dextrorphan (CYP2D6 metabolite), and terfenadine alcohol metabolite (CYP3A4 metabolite) were quantified by LC/MS/MS.

Addition of only DMSO being a solvent dissolving a compound to a reaction system was adopted as a control (100%), remaining activity (%) was calculated and $IC_{50}$ was calculated by reverse presumption by a logistic model using a concentration and an inhibition rate.

Compound I-2: five kinds >20 µM

Test Example 6

Fluctuation Ames Test

Each 20 µL of freeze-stored *Salmonella typhimurium* (TA98 and TA100 strain) is inoculated in 10 mL of liquid nutrient medium (2.5% Oxoid nutrient broth No. 2), and the cultures are incubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension is added to 110 mL of Exposure medium (Micro F buffer containing Biotin: 8 µg/mL, histidine: 0.2 µg/mL, glucose: 8 mg/mL). 3.16 mL of TA100 culture is added to 120 mL of Exposure medium to prepare the test bacterial solution. 588 µL of the test bacterial solution (or mixed solution of 498 µl of the test bacterial solution and 90 µL of the S9 mix in the case with metabolic activation system) are mixed with each 12 µL of the following solution: DMSO solution of the compound of the present invention (several stage dilution from maximum dose 50 mg/mL at 2 to 3-fold ratio); DMSO as negative control; 50 µg/mL of 4-nitroquinoline-1-oxide DMSO solution as positive control for TA98 without metabolic activation system; 0.25 µg/mL of 2-(2-furyl)-3-(5-nitro-2-furyl)acrylamide DMSO solution as positive control for TA100 without metabolic activation system; 40 µg/mL of 2-aminoanthracene DMSO solution as positive control for TA98 with metabolic activation system; or 20 µg/mL of 2-aminoanthracene DMSO solution as positive control for TA100 with metabolic activation system. A mixed solution is incubated at 37° C. under shaking for 90 minutes. 460 µL of the bacterial solution exposed to the compound of the present invention is mixed with 2300 µL of Indicator medium (Micro F buffer containing biotin: 8 µg/mL, histidine 0.2 µg/mL, glucose: 8 mg/mL, Bromo Cresol Purple: 37.5 µg/mL), each 50 µL is dispensed into 48 wells/dose in the microwell plates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose is counted, and evaluate the mutagenicity by comparing with the negative control group. (−) means that mutagenicity is negative and (+) means positive.

Test Example 7-1

Solubility Test

A 2-fold dilution series (12 points) of a 10 mM solution of a compound of the present invention in DMSO was added to a medium (JP-I, JP-II) (2%), and solubility was assessed by 3 stages (High; >40 µM, Medium; 3-40 Low; <3 µM) from a turbidity after 4 hours.

Compound I-1: High (JP-II)

Test Example 7-2

Solubility Test

The solubility of each compound is determined under 1% DMSO addition conditions. A 10 mmol/L solution of the compound is prepared with DMSO, and 6 μL of the compound of the present invention solution is added to 594 μL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1 (v/v), and the compound concentration in the filtrate is measured with HPLC or LC/MS/MS by the absolute calibration method.

Test Example 8

Metabolism Stability Test

Using a commercially available pooled human hepatic microsomes, a compound of the present invention is reacted for a constant time, a remaining rate is calculated by comparing a reacted sample and an unreacted sample, thereby, a degree of metabolism in liver of the compound of the present invention is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution is added to 100 μL of a methanol/acetonitrile=1/1 (v/v), mixed and centrifuged at 3000 rpm for 15 minutes. The compound of the present invention in the supernatant is quantified by LC/MS/MS, and a remaining amount of the compound of the present invention after the reaction is calculated, letting a compound amount at 0 minute reaction time to be 100%.

Test Example 9 hERG Test

For the purpose of assessing risk of an electrocardiogram QT interval prolongation, effects on delayed rectifier K+ current ($I_{Kr}$), which plays an important role in the ventricular repolarization process, of the compound of the present invention was studied using HEK293 cells expressing human ether-a-go-go related gene (hERG) channel.

A cell was retained at a membrane potential of −80 mV by whole cell patch clamp method using an automated patch clamp system (PatchXpress 7000A, Axon Instruments Inc.) and leakage potential at −50 mV was generated. $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the compound of the present invention have been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver.1, Molecular Devices Corporation). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.

Compound I-2: 12.3%

Test Example 10

Powder Solubility Test

Appropriate amounts of the compound of the present invention are put into appropriate containers. To the respective containers are added 200 μL of JP-1 fluid (sodium chloride 2.0 g, hydrochloric acid 7.0 mL and water to reach 1000 mL), 200 μL of JP-2 fluid (500 mL of water is added to 500 mL of phosphate buffer (pH 6.8)), and 200 μL of 20 mmol/L sodium taurocholate (TCA)/JP-2 fluid (TCA 1.08 g and water to reach 100 mL). In the case that the compound of the present invention is dissolved after the addition of the test fluid, the compound of the present invention is added as appropriate. The containers are sealed, and shaken for 1 hour at 37° C. The mixtures are filtered, and 100 μL of methanol is added to each of the filtrate (100 μL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

Test Example 11

BA Test

Materials and methods for studies on oral absorption
(1) Animal: mouse or SD rat
(2) Breeding conditions: mouse or SD rat is allowed to freely take solid feed and sterilized tap water.
(3) Dose and grouping: orally or intravenously administered at a predetermined dose; grouping is as follows (Dose depends on the compound)
Oral administration: 1 to 30 mg/kg (n=2 to 3)
Intravenous administration: 0.5 to 10 mg/kg (n=2 to 3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood is collected over time, and the plasma concentration of the compound of the present invention is measured by LC/MS/MS
(7) Statistical analysis: regarding the transition of the plasma concentration of the compound of the present invention, the area under the plasma concentration-time curve (AUC) is calculated by non-linear least squares program WinNonlin (Registered trademark), and the bioavailability (BA) of the compound of the present invention is calculated from the AUCs of the oral administration group and intravenous administration group Test Example 12

Brain Distribution Studies

Compound of the present invention is intravenously administered to a rat at 0.5 mg/mL/kg dosage. 30 Minutes later, all blood is drawn from vena cava inferior under isoflurane anesthesia for death from exsanguination.

The brain is enucleated and 20-25% of homogenate thereof is prepared with distilled water.

The obtained blood is used as plasma after centrifuging. To the brain sample is added the control plasma at 1:1. To the plasma samples is added the control brains at 1:1. Each sample is measured using LC/MS/MS. The obtained area ratio (a brain/plasma) is used for the brain Kp value.
Compound I-7: 1.7

Test Example 13

Ames Test

Ames test is performed by using Salmonellas (*Salmonella typhimurium*) TA 98, TA100, TA1535 and TA1537 and *Escherichia coli* WP2uvrA as test strains with or without metabolic activation in the pre-incubation method to check the presence or absence of gene mutagenicity of compounds of the present invention.

Test Example 14

P-gp Substrate Test

Compound of the present invention is added in one side of the trans well wherein human MDR1 expressing cells or parent cells are monolayer cultivated, and reacted for a pre-determined period of times. Efflux Ratio (ER; ratio of membrane permeability coefficients of the direction from Basolateral side to Apical side (B to A) and the direction from Apical side to Basolateral side (A to B)) of MDR1 expressing cells and parent cells is calculated from the membrane permeability coefficients of A to B and of B to A. The compound of the present invention is investigated whether a P-gp substrate or not by comparing ER values of MDR1 expressing cells and parent cells.

Formulation Examples

The following Formulation Examples are only exemplified and not intended to limit the scope of the present invention.

Formulation Example 1

Tablets

| Compound of the present invention | 15 mg |
|---|---|
| Lactose | 15 mg |
| Calcium stearate | 3 mg |

All of the above ingredients except for calcium stearate are uniformly mixed. Then the mixture is crushed, granulated and dried to obtain a suitable size of granules. Then, calcium stearate is added to the granules. Finally, tableting is performed under a compression force.

Formulation Example 2

Capsules

| Compound of the present invention | 10 mg |
|---|---|
| Magnesium stearate | 10 mg |
| Lactose | 80 mg |

The above ingredients are mixed uniformly to obtain powders or fine granules, and then the obtained mixture is filled in capsules.

Formulation Example 3

Granules

| Compound of the present invention | 30 g |
|---|---|
| Lactose | 265 g |
| Magnesium stearate | 5 g |

After the above ingredients are mixed uniformly, the mixture is compressed.

The compressed matters are crushed, granulated and sieved to obtain suitable size of granules.

[Industrial Applicability]

The compound of the present invention can be a useful medicament for diseases induced by production, secretion and/or deposition of amyloid β proteins.

The invention claimed is:
1. A compound of the formula (I):

[Chemical Formula 1]

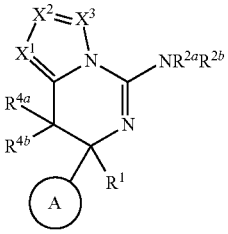

wherein ring A is a substituted or unsubstituted benzene or a substituted or unsubstituted thiophene,
$X^1$—$X^2$=$X^3$ is $CR^5$—$CR^6$=$CR^7$, N—$CR^6$=$CR^7$, $CR^5$—N=$CR^7$ or $CR^5$—$CR^6$=N,
$R^1$ is substituted or unsubstituted alkyl,
$R^{2a}$ and $R^{2b}$ are both hydrogen,
$R^{4a}$, $R^{4b}$, $R^5$, $R^6$ and $R^7$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, and $R^{4a}$ and $R^{4b}$ together with the carbon atom to which they are attached may form a substituted or unsubstituted carbocycle or a substituted or unsubstituted heterocycle, provided that when $X^1$—$X^2$=$X^3$ is N—$CR^6$=$CR^7$ or $CR^5$—$CR^6$=N, then ring A is

[Chemical Formula 2]

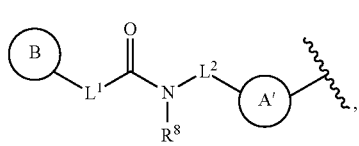

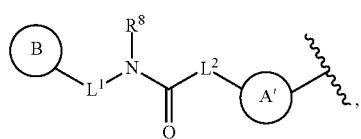

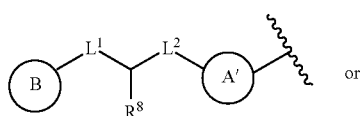 or

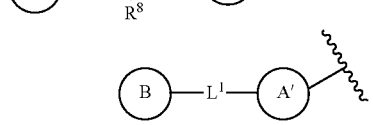

wherein $L^1$ and $L^2$ are each independently a bond, substituted or unsubstituted alkylene, substituted or unsubstituted alkenylene or substituted or unsubstituted alkynylene, ring A' is a substituted or unsubstituted benzene or a substituted or unsubstituted thiophene, and ring B and ring B' are each independently a substituted or unsubstituted carbocycle or a substituted or unsubstituted heterocycle, provided that when $L^1$ is a bond, then ring B' is substituted or unsubstituted pyridine, substituted or unsubstituted pyrimidine or substituted or unsubstituted pyrazine, and $R^8$ is each independently hydrogen, hydroxy, substituted or unsubstituted alkyl, substituted or unsubstituted alkenyl, substituted or unsubstituted alkynyl or substituted or unsubstituted acyl, its pharmaceutically acceptable salt or a solvate thereof.

2. The compound according to claim 1 wherein $X^1$—$X^2$=$X^3$ is $CR^5$—$CR^6$=$CR^7$ or $CR^5$—N=$CR^7$, its pharmaceutically acceptable salt or a solvate thereof.

3. The compound according to claim 1 wherein ring A is

[Chemical Formula 3]

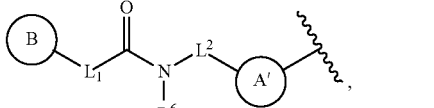

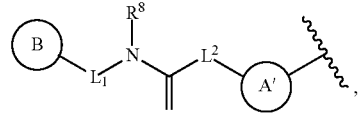

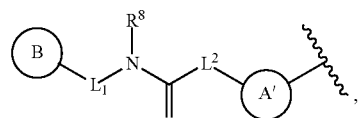

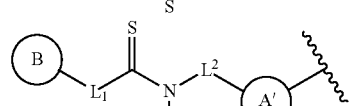

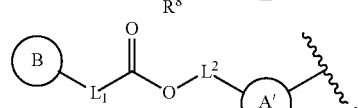

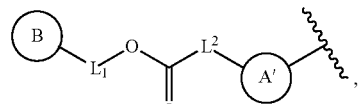

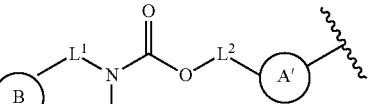

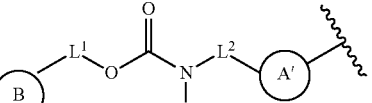

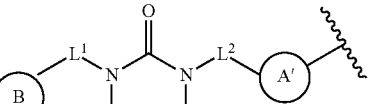

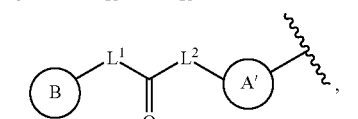

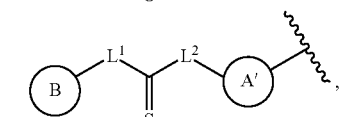

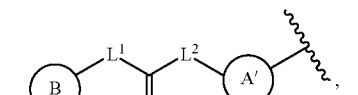

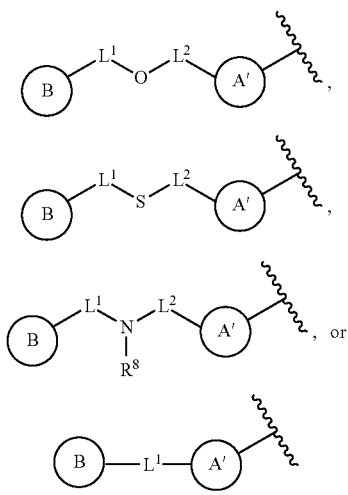

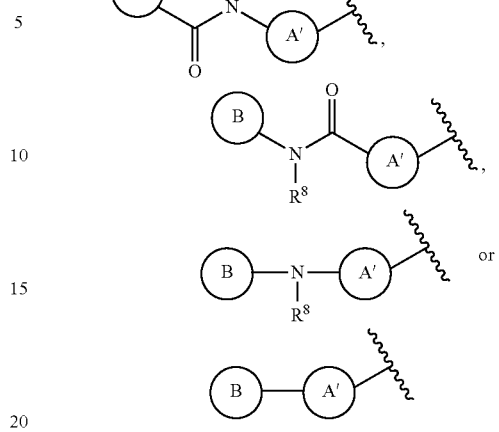

[Chemical Formula 5]

wherein ring A' is a substituted or unsubstituted benzene or a substituted or unsubstituted thiophene, and ring B is a substituted or unsubstituted carbocycle or a substituted or unsubstituted heterocycle, $L^1$ and $L^2$ are each independently a bond, substituted or unsubstituted alkylene, substituted or unsubstituted alkenylene or substituted or unsubstituted alkynylene, and $R^8$ and $R^9$ are each independently hydrogen, hydroxy, substituted or unsubstituted alkyl, substituted or unsubstituted alkenyl, substituted or unsubstituted alkynyl or substituted or unsubstituted acyl, its pharmaceutically acceptable salt or a solvate thereof.

4. The compound according to claim 1 wherein ring A is

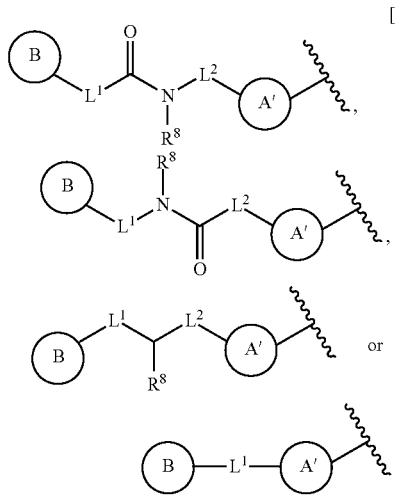

[Chemical Formula 4]

its pharmaceutically acceptable salt or a solvate thereof.

5. The compound according to claim 3 wherein each of $L^1$ and $L^2$ is a bond, its pharmaceutically acceptable salt or a solvate thereof.

6. The compound according to claim 1 wherein $X^1$—$X^2$=$X^3$ is N—$CR^6$=$CR^7$ or $CR^5$—$CR^6$=N, and ring A is its pharmaceutically acceptable salt or a solvate thereof.

7. The compound according to claim 4 wherein ring A' is substituted or unsubstituted benzene, and ring B or ring B' is substituted or unsubstituted pyridine, substituted or unsubstituted pyrimidine or substituted or unsubstituted pyrazine, its pharmaceutically acceptable salt or a solvate thereof.

8. The compound according to claim 1, wherein $R^{4a}$ and $R^{4b}$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy or substituted or unsubstituted alkynyloxy, its pharmaceutically acceptable salt or a solvate thereof.

9. The compound according to claim 1, wherein $R^{4a}$ and $R^{4b}$ are each independently hydrogen, halogen, hydroxy, substituted or unsubstituted alkyl, substituted or unsubstituted alkenyl or substituted or unsubstituted alkynyl, its pharmaceutically acceptable salt or a solvate thereof.

10. The compound according to claim 1, wherein $R^5$, $R^6$ and $R^7$ are each independently hydrogen, halogen, hydroxy, substituted or unsubstituted alkyl, substituted or unsubstituted alkenyl, substituted or unsubstituted alkoxy, substituted or unsubstituted alkenyloxy, substituted or unsubstituted alkylthio, substituted or unsubstituted alkenylthio, substituted or unsubstituted acyl, substituted or unsubstituted acyloxy, cyano, carboxy, substituted or unsubstituted alkoxycarbonyl, substituted or unsubstituted alkenyloxycarbonyl, substituted or unsubstituted amino, substituted or unsubstituted carbamoyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, or substituted or unsubstituted heterocyclyloxycarbonyl, its pharmaceutically acceptable salt or a solvate thereof.

11. The compound according to claim 1, wherein $R^5$, $R^6$ and $R^7$ are each independently hydrogen, halogen, hydroxy, substituted or unsubstituted alkyl, substituted or unsubstituted alkoxy, substituted or unsubstituted acyl, substituted or unsubstituted acyloxy, cyano, carboxy, substituted or unsubstituted alkoxycarbonyl or substituted or unsubstituted amino, its pharmaceutically acceptable salt or a solvate thereof.

12. The compound according to claim 1, wherein $R^{4a}$ and $R^{4b}$ are hydrogen, and $R^5$, $R^6$ and $R^7$ are hydrogen, its pharmaceutically acceptable salt or a solvate thereof.

13. The compound according to claim 1, wherein ring A is

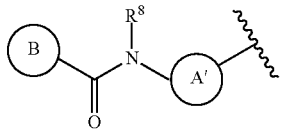

its pharmaceutically acceptable salt or a solvate thereof.

14. A pharmaceutical composition comprising the compound according to claim 1, its pharmaceutically acceptable salt or a solvate thereof.

15. A method for inhibiting BACE1 activity comprising administering the compound according to claim 1, its pharmaceutically acceptable salt or a solvate thereof.

16. A method for treating dementia of Alzheimer's disease, senile dementia of Alzheimer's disease, mild cognitive impairment (MCI), Alzheimer's disease with vascular type dementia, Alzheimer's disease with diffuse Lewy body disease, comprising administering the compound according to claim 1, its pharmaceutically acceptable salt or a solvate thereof.

* * * * *